United States Patent
Kyle et al.

(10) Patent No.: US 9,062,352 B2
(45) Date of Patent: Jun. 23, 2015

(54) LOCI ASSOCIATED CHARCOAL ROT DROUGHT COMPLEX TOLERANCE IN SOYBEAN

(71) Applicant: PIONEER HI BRED INTERNATIONAL INC, Johnston, IA (US)

(72) Inventors: Donald Kyle, Princeton, IL (US); Jeffrey A. Thompson, Edwardsville, IL (US); Julian M. Chaky, Urbandale, IA (US)

(73) Assignee: PIONEER HI-BRED INTERNATIONAL, INC., Johnston, IA (US)

(*) Notice: Subject to any disclaimer, the term of this patent is extended or adjusted under 35 U.S.C. 154(b) by 0 days.

(21) Appl. No.: 13/872,927

(22) Filed: Apr. 29, 2013

(65) Prior Publication Data

US 2013/0227725 A1   Aug. 29, 2013

Related U.S. Application Data

(62) Division of application No. 12/342,218, filed on Dec. 23, 2008, now Pat. No. 8,329,982.

(60) Provisional application No. 61/082,024, filed on Jul. 18, 2008, provisional application No. 61/009,643, filed on Dec. 31, 2007.

(51) Int. Cl.
  *C12Q 1/68* (2006.01)

(52) U.S. Cl.
  CPC .................................. *C12Q 1/6895* (2013.01)

(58) Field of Classification Search
  USPC .............................................. 800/265
  See application file for complete search history.

(56) References Cited

PUBLICATIONS

Cregan, et al., An Integrated Genetic Linkage Map of the Soybean Genome, Crop. Sci. (1999), 39:1464-1490.
Mengistu, et al., Charcoal Rot Disease Assessment of soybean Geneotypes Using a Colony-Forming Unit Index, Crop Sci., (2007), 47:2453-2461.
Smith, et al., Field Screening of Commercial and Experimental Soybean Cultivars for Their Reaction to Macrophomina phaseolina, Plant Disease (1997), 81(4): 363-368.
Paris, et al., Registration of Soybean Germplasm Line DT97-4290 with Moderate Resistance to Charcoal Rot, Crop Sci., (2006), 46:2324.
Diwan, et al., Automated sizing of fluorescent-labeled simple sequence repeat (SSR) markers to assay genetic variation in soybean, Theor. Appl. Genet (1997), 95:723-733.
Song, et al., A new integrated genetic linkage map of the soybean, Theor. Appl. Genet (2004), 109:122-128.
Jansen, et al., Complex plant traits: time for polygenic analysis, Trends in Plant Science (1996), 1(3): 89-94.

*Primary Examiner* — Medina A Ibrahim
(74) *Attorney, Agent, or Firm* — Pioneer Hi-Bred Int'l., Inc.

(57) ABSTRACT

The invention relates to methods and compositions for identifying soybean plants that are tolerant, have improved tolerance or are susceptible to Charcoal Rot Drought Complex. The methods use molecular genetic markers to identify, select and/or construct tolerant plants or identify and counter-select susceptible plants. Soybean plants that display tolerance or improved tolerance to Charcoal Rot Drought Complex that are generated by the methods of the invention are also a feature of the invention.

13 Claims, 29 Drawing Sheets

Figure 8:

| Marker | Marker Type | Chrom | Relative Map Position (cM) | Pioneer Map Position | Method of Identification | Gene Pool Analyzed/ Mapping Population | Adjusted Probability |
|---|---|---|---|---|---|---|---|
| S63880-CB | SSR | B1 | | 99.00 | Trait Allele Correlation | 167 Pioneer Experimental or Commercial Products with known CRDC reaction | 0.02 |
| S60211-TB | EST-SSR | B2 | 36.51 | 46.20 | 06 Intergroup Analysis | 38 CRDC Susceptible lines versus 29 CRDC Tolerant Lines | 0.039175 |
| S00415-1-A | SNP | C1 | 71.24 | 67.9 | Marker Regression and Interval Mapping | 368 F5-derived lines from a mating of A4715 (resistant parent) and 9362 (susceptible parent) | 0.00000 |
| Sct_028 | genomic SSR | C2 | 122.01 | 168.30 | 05 Intergroup Analysis | 39 CRDC Susceptible lines versus 30 CRDC Tolerant Lines | 0.056087 |
| Sct_028 | genomic SSR | C2 | 122.01 | 168.30 | Trait Allele Correlation | 167 Pioneer Experimental or Commercial Products with known CRDC reaction | 0.1 |
| S00705-1-A | SNP | D1b | 83.8 | 111.1 | Marker Regression and Interval Mapping | 368 F5-derived lines from a mating of A4715 (resistant parent) and 9362 (susceptible parent) | 0.00071 |
| Satt512 | genomic SSR | E | 16.73 | 66.00 | 05 & 06 Intergroup Analysis | 38 CRDC Susceptible lines versus 29 CRDC Tolerant Lines | 0.029309 |
| Satt512 | genomic SSR | E | 16.73 | 66.00 | Trait Allele Correlation | 167 Pioneer Experimental or Commercial Products with known CRDC reaction | 0 |
| Sat_117 | SSR | G | 100.00 | 138.40 | 06 Intergroup Analysis | 38 CRDC Susceptible lines versus 29 CRDC Tolerant Lines | 0.109438 |
| Sat_117 | SSR | G | 100.00 | 138.40 | Trait Allele Correlation | 167 Pioneer Experimental or Commercial Products with known CRDC reaction | 0.04 |
| S01954-1-A | SNP | G | 96.56 | 128.47 | Marker Regression and Interval Mapping | 368 F5-derived lines from a mating of A4715 (resistant parent) and 9362 (susceptible parent) | 0.00000 |
| P13158A | SNP | H | 111.93 | 130.00 | Trait Allele Correlation | 167 Pioneer Experimental or Commercial Products with known CRDC reaction | 0.03 |
| S02118-1-A | SNP | N | 105.63 | 106.0 | Marker Regression and Interval Mapping | 368 F5-derived lines from a mating of A4715 (resistant parent) and 9362 (susceptible parent) | 0.00213 |

Figure 1

| Marker Name | LG | Left Primer Sequence | SEQ ID | Right Primer Sequence | SEQ ID |
|---|---|---|---|---|---|
| Sct_028 | C2 | TCGCCGGTACAAAAG | 1 | CGAATGAACAAACAAACA | 2 |
| Satt512 | E | AACGTCTTCAAGTCAAGTGCCTACA | 3 | GCCCACATAGTTTTCATTTTCTCCA | 4 |
| S60211-TB | B2 | GAAGATCCTAACACGATGGCCG | 5 | TTCGTTGTTTCCTTCATTGCCG | 6 |
| Sat_117 | G | TTTGGCAGTTTCTTGTAG | 7 | GCTGGATCGGCAGTTA | 8 |
| S63880-CB | B1 | AGTCCTCCTCGCCAACAACAAC | 9 | TTCATTTCATTTCCAAGCGGGT | 10 |

Figure 2

| SNP Marker | LG | Left Primer Sequence | SEQ ID | Right Primer Sequence | SEQ ID | Probe 1 Sequence | SEQ ID | Probe 2 Sequence | SEQ ID |
|---|---|---|---|---|---|---|---|---|---|
| P13158A | H | ACTGGAAGAGGGTGCTTAGGGAATCTG | 11 | GAGAATCTAGTCTACCACCATACCACGAAC | 12 | ACACTGCTTAC | 13 | TTTTTGCTAGAG | 14 |
| S00415-1-A | C1 | ACAAAAGCGGTGCTGTTTGCTC | 15 | TATGACCATGGAGTGCAAGGTGG | 16 | CAACCTCCTTCTTC | 17 | CAACCTCGTTCTTC | 18 |
| S00705-1-A | D1b | TGTGAGATGATGCCTCCAGGTTT | 19 | AATGCGAGCCAAGCAAAATGAT | 20 | TTTGTCATCCAACTCA | 21 | TTTGTCCTCCAACTCA | 22 |
| S02118-1-A | N | GGTCCATATTACTTGAAATACAAAGTTTACAGTATG | 23 | CCCAGAACAGGTAATAGTAGGTATATGCTTATTAA | 24 | TCCAATTGCTTCTTT | 25 | TCCAATTGCGTCTTT | 26 |
| S01954-1-A | G | CGATTATATAGGCGCCTAGGTAAACTTTG | 27 | GACGAGAGAATCCTTGCCAAATTTATAG | 28 | TACGATAATGCCCTCG | 29 | TTACGATAACGCCCTC | 30 |

Figure 3

| Marker | Allele | Size Range (bp) | |
|---|---|---|---|
| | | RANGE_LO | RANGE_HI |
| Sct_028 | 1 | 236.1 | 237.4 |
| | 2 | 242.1 | 243.2 |
| | 3 | 244.1 | 245.2 |
| | 4 | 248.1 | 249.2 |
| | | | |
| Satt512 | 1 | 310.1 | 311.0 |
| | 2 | 313.0 | 314.1 |
| | 3 | 316.2 | 317.7 |
| | 4 | 319.4 | 320.9 |
| | 5 | 325.5 | 327.0 |
| | 6 | 328.7 | 330.1 |
| | 7 | 331.8 | 333.1 |
| | | | |
| S60211-TB | 1 | 219.0 | 220.0 |
| | 2 | 224.5 | 225.5 |
| | | | |
| Sat_117 | 1 | 203.2 | 203.4 |
| | 2 | 208.9 | 209.1 |
| | 3 | 210.3 | 211.5 |
| | 4 | 212.8 | 213.2 |
| | 5 | 216.9 | 217.3 |
| | 6 | 218.2 | 219.4 |
| | 7 | 220.1 | 221.2 |
| | 8 | 222.6 | 223.3 |
| | 9 | 224.8 | 224.9 |
| | 10 | 226.2 | 227.0 |
| | 11 | 232.6 | 233.0 |
| | 12 | 234.7 | 234.9 |
| | 13 | 242.8 | 242.9 |
| | 14 | 252.0 | 252.2 |
| | 15 | 256.0 | 256.2 |
| | | | |
| S63880-CB | 1 | 212.0 | 213.0 |
| | 2 | 215.0 | 216.6 |
| | 3 | 219.0 | 219.5 |
| | 4 | 228.5 | 229.5 |
| | | | |

Figure 4

| Marker | Linked Markers | Closely Linked Markers |
|---|---|---|
| Sct_028 LG-C2 | L148_1, Satt376, Satt363, Sat_076, Satt286, A063_2, Sat_402, BLT032_1, BLT053_9, Sle28_1, Satt277, K011_3, Bng164_1, pcr2_150, Satt365, Satt205, Satt557, Satt289, Satt134, Sat_312, Satt489, Satt319, Satt658, AG36, Satt100, Sat_251, L050_2, A109_2, Sat_142, B131_1, Satt708, Satt708, A397_1, Sat_238, Satt460, Satt079, Sat_263, BLT029_1, Staga001, K365_1, Satt307, A538_1, P029_1, K474_1, K474_2, RGA_1e, Satt202, Staga001, K365_1, Sat_202, Sat_252, Satt316, Satt433, C056_1, A748_1, Satt371, RGA_1e, Satt202, Sat_252, Satt316, Satt433, C056_1, A748_1 | Satt205, Satt557, Satt289, Satt134, Sat_312, Satt489, Satt319, Satt658, AG36, Satt100, Sat_251, L050_2, A109_2, Sat_142, B131_1, Satt708, A397_1, Sat_238, Satt460, Satt079, Sat_263, BLT029_1, Staga001, K365_1, Satt307, A538_1, P029_1, K474_1, K474_2, RGA_1e, Satt202, Sat_252, Satt316, Satt433, C056_1, A748_1 |
| Satt512 LG-E | T183_1, A135_3, Satt575, Satt213, SAC7_1, Sat_112, A242_2, Satt411, Pb, T153_2, Bng027_1, Sat_124, A963_1, G214_10, pcr2_188, Satt384, Satt691, L194_2, T092_2, Satt720, A053_1, A086_1, OP_M12b, A636_1, A517_1, R051_1, A458_1, A455_1, Bng193_1, A646_1, K229_1, B174_1, A454_1, Satt651, Satt212, Satt598, A203_1, Satt573, OP_M02b, A374_1, A656_1, Sat_136, Satt606, A386_1, Satt699, Satt602 | SAC7_1, Sat_112, A242_2, Satt411, Pb, T153_2, Bng027_1, Sat_124, A963_1, G214_10, pcr2_188, Satt384, Satt691, L194_2, T092_2, Satt720, A053_1, A086_1, OP_M12b, A636_1, A517_1 |
| S60211-TB LG-B2 | Sat_264, A135_1, L191_1, A685_1, Bng069_2, Satt467, T270_2, Sat_342, Satt126, G214_23, A352_1, Sat_287, A242_1, RGA_8, A343_1, OP_T02, B142_1, Sct_034, Satt083, A018_1, Satt168, OP_E02a, Satt416, BLT049_2 | Satt126, G214_23, A352_1, Sat_287, A242_1, RGA_8, A343_1, OP_T02, B142_1 |
| Sat_117 LG-G | Satt288, A121_2, A885_1, Satt612, K493_1, T005_2, bac1F11Rhnd, OP_M02a, p28_13_2, AF162283, A245_2, OPAD08, Sct_199, Satt472, S01954-1-A, Satt191, A235_1, L002_2, OP_H04, H3_54HE_1, L154_1, Sat_117, A690_2, Bng069_1, Sat_117, A690_2, Bng069_1, Sct_187, Sat_372, Sat_064, A378_1, L183_1, L120_1, A586_2, Mpi, L050_11, A681_1 | A245_2, OPAD08, Sct_199, Satt472, S01954-1-A, Satt191, A235_1, L002_2, OP_H04, H3_54HE_1, L154_1, Sat_117, A690_2, Bng069_1, Sct_187, Sat_372, Sat_064, A378_1 |
| P13158A LG-H | Bng202_1, Bng104_1, Satt629, BLT019_1, Sat_158, K327_1, Ps, Satt302, Sat_175, B069_1, Sat_216, Satt637, Satt142, Satt293, Satt317, A748_2, Satt181, A810_1, Sat_218, Sat_180, Satt434, RGA_6c, K007_1, A162_1, A570_1, L195_1 | Satt142, Satt293, Satt317, A748_2, Satt181, A810_1, Sat_218, Sat_180, Satt434 |
| S63880-CB LG-B1 | Satt415, Satt583, Sat_364, Satt444, Satt665, Sat_123, Satt359, R244_1, Satt484, H3_c6_1, Satt453, Sat_331, A567_1, BE801538, AQ851479, A598_1, L050_1 | Satt665, Sat_123, Satt359, R244_1 |

Figure 5

| Marker | Linked Markers | Closely Linked Markers |
|---|---|---|
| S00415-1-A LG-C1 | Bng019_1, K472_1, V38a, Satt578, Satt607, A519_3, Bng140_1, Satt646, Bng161_1, Dia, L192_1, Satt190, Satt718, Sat_404, Satt661, Satt139, AW277661, Satt136, Sat_416, Sat_357, G214_25, Sat_085, G214_24, Satt294, Sat_322, Satt476, Sat_042, Satt195, Bng143_1, Satt670, Sat_207, Satt713, Sat_311, A063_1, Sct_191 | Satt607, A519_3, Bng140_1, Satt646, Bng161_1, Dia, L192_1, Satt190, Satt161, Satt718, Sat_404, Satt661, Satt139, AW277661, Satt136, Satt361, Sat_077, Satt399, Sat_416, Sat_357, G214_25, Sat_085, G214_24 |
| S00705-1-A LG-D1b | A605_1, Sat_423, A747_1, Sat_135, Satt412, Satt141, Satt290, Satt611, Satt604, K011_4, Satt506, Satt005, Satt600, L050_3, Satt537, Satt579, Satt282, Sat_089, Satt189, Satt350, Satt428, Mng137_1, Bng047_1, Sat_169, Satt644, Satt041, RGA_1f, Satt546, M7E8mr2, B194_2, Sat_139, Satt703, Satt172, Sat_069, Idh1, A519_2 | Satt428, Mng137_1, Bng047_1, Sat_169, Satt644, Satt041, RGA_1f, Satt546, M7E8mr2, B194_2 |
| S-2118-1-A LG-N | Sat_306, Sat_295, Satt022, Sat_125, A455_2, A363_3 | Satt022, Sat_125, A455_2, A363_3 |

Figure 5
(continued)

Figure 6

| Chromosome A1 | | Chromosome A1 | |
|---|---|---|---|
| Marker | Position (cM) | Marker | Position (cM) |
| Sat_137 | 0.00 | R183_1 | 42.41 |
| Satt684 | 3.54 | Sat_356 | 42.79 |
| A487_1 | 8.82 | A510_1 | 43.70 |
| A065_2 | 12.50 | Satt050 | 46.45 |
| Sat_368 | 14.37 | B030_2 | 49.29 |
| Satt572 | 14.65 | A096_1 | 51.79 |
| Satt276 | 17.16 | Satt717 | 51.95 |
| A083_2 | 17.82 | Sat_407 | 52.32 |
| Sat_344 | 19.37 | K400_1 | 53.36 |
| Satt165 | 23.00 | A262_1 | 53.38 |
| Bng074_2 | 23.95 | T153_3 | 56.18 |
| Mng241_1 | 24.63 | Sat_171 | 57.79 |
| K647_2 | 24.90 | Satt648 | 59.18 |
| Satt593 | 25.55 | B172_1 | 60.09 |
| Satt625 | 26.16 | BLT053_5 | 62.16 |
| Satt382 | 26.42 | Satt385 | 64.73 |
| Sat_371 | 26.87 | SYNOD26A | 66.80 |
| Sat_369 | 27.18 | BLT053_2 | 67.95 |
| K478_2 | 27.35 | Satt619 | 69.20 |
| Satt042 | 27.66 | Satt545 | 71.38 |
| Satt449 | 27.78 | A975_1 | 75.41 |
| Satt471 | 27.95 | Sat_267 | 78.44 |
| Satt526 | 27.98 | A256_2 | 80.54 |
| Satt454 | 28.08 | K636_2 | 81.51 |
| Satt248 | 28.29 | Satt599 | 85.58 |
| Satt364 | 28.95 | Satt174 | 88.58 |
| Sat_410 | 29.62 | Bng077_1 | 91.23 |
| A329_2 | 30.28 | A104_1 | 92.30 |
| Satt300 | 30.93 | A170_1 | 92.55 |
| Sat_385 | 31.07 | Satt200 | 92.88 |
| Sat_384 | 31.08 | Satt236 | 93.23 |
| Satt591 | 31.13 | T155_1 | 93.58 |
| AZ536570 | 31.38 | Satt511 | 94.19 |
| K258_1 | 31.95 | B170_1 | 94.91 |
| Satt155 | 32.68 | Satt225 | 95.16 |
| A407_2 | 33.04 | Satt258 | 95.54 |
| Sat_265 | 33.27 | Sat_374 | 95.68 |
| Satt073 | 33.97 | Satt211 | 95.95 |
| A110_2 | 34.23 | Sat_271 | 97.76 |
| A053_2 | 34.54 | Bng017_1 | 100.58 |
| L194_1 | 34.63 | Sat_217 | 101.57 |
| Bng116_1 | 34.90 | A082_1 | 102.30 |
| G214_1 | 35.59 | | |
| Bng132_1 | 38.13 | | |
| A064_3 | 42.08 | | |

Figure 6 (continued)

| Chromosome A2 | | Chromosome A2 | | Chromosome A2 | |
|---|---|---|---|---|---|
| Marker | Position (cM) | Marker | Position (cM) | Marker | Position (cM) |
| Sat_383 | 0.00 | Sat_115 | 81.01 | Lf1 | 126.72 |
| Satt390 | 9.14 | OP_M12a | 83.12 | Satt209 | 128.44 |
| A170_2 | 10.75 | Sat_129 | 84.08 | Satt455 | 129.86 |
| K636_1 | 14.40 | Sat_199 | 84.08 | BLT053_1 | 131.19 |
| Bng181_1 | 14.40 | A638_1 | 85.80 | mQ039_1 | 131.60 |
| Sct_067 | 14.99 | Sat_233 | 86.41 | Sat_294 | 131.97 |
| A256_1 | 15.05 | Satt089 | 87.57 | A505_1 | 132.30 |
| Bng077_2 | 18.54 | Satt377 | 90.83 | A065_1 | 133.05 |
| Sat_406 | 25.90 | Satt119 | 92.43 | OPAV06a | 135.22 |
| Satt207 | 26.50 | VSP27 | 92.52 | T036_1 | 141.08 |
| Sat_319 | 27.90 | Bng121_1 | 94.30 | BLT036_1 | 143.97 |
| Satt480 | 28.44 | Satt525 | 96.97 | Bng225_1 | 144.00 |
| A085_1 | 32.22 | Satt233 | 100.08 | Satt409 | 145.57 |
| Satt589 | 33.95 | G214_2 | 103.47 | K644_3 | 148.13 |
| Satt493 | 35.02 | A117_1 | 104.30 | A572_1 | 148.55 |
| Sat_409 | 35.68 | Sat_250 | 105.18 | Bng205_1 | 149.10 |
| BE820148 | 35.93 | Sat_392 | 106.29 | Bng029_1 | 151.14 |
| Satt177 | 36.77 | Satt437 | 107.05 | Satt228 | 154.11 |
| Sat_181 | 38.06 | A096_2 | 107.36 | L144_1 | 155.32 |
| A110_1 | 38.41 | Satt508 | 108.77 | Ap | 157.27 |
| Satt315 | 45.29 | Satt327 | 109.83 | Sat_347 | 158.38 |
| I | 48.84 | Satt329 | 110.94 | Satt538 | 159.63 |
| Sat_400 | 49.38 | Sat_310 | 111.45 | Satt429 | 162.02 |
| L199_1 | 49.93 | R028_1 | 111.94 | Satt378 | 165.72 |
| A262_2 | 50.08 | B132_1 | 112.30 | | |
| T153_1 | 50.41 | Sat_232 | 112.87 | | |
| B172_2 | 51.08 | A690_1 | 113.44 | | |
| Satt632 | 51.50 | Sct_194 | 113.57 | | |
| Sat_157 | 51.57 | K417_1 | 114.25 | | |
| Sat_162 | 51.86 | Satt158 | 115.25 | | |
| BLT024_1 | 52.49 | Satt421 | 115.93 | | |
| A486_1 | 53.16 | Sat_382 | 116.41 | | |
| Sat_215 | 53.75 | Satt707 | 116.62 | | |
| Satt187 | 54.91 | Sat_378 | 116.62 | | |
| Sat_212 | 56.32 | Sat_377 | 116.63 | | |
| A510_4 | 56.52 | Satt470 | 116.73 | | |
| GMENOD2B_SSR | 58.43 | mO103_1 | 118.48 | | |
| Satt424 | 60.59 | Sat_040 | 118.63 | | |
| A975_2 | 61.29 | K443_2 | 119.08 | | |
| SAC7_2 | 64.88 | Satt333 | 119.58 | | |
| SAC3_1 | 65.73 | p28_9 | 121.00 | | |
| A111_1 | 67.33 | p28_10 | 121.00 | | |
| AW132402 | 67.86 | p28_8 | 121.00 | | |
| A136_1 | 71.37 | Sat_097 | 122.05 | | |
| P003_1 | 75.88 | Sat_138 | 123.26 | | |
| Satt341 | 77.69 | Satt133 | 125.37 | | |

Figure 6 (continued)

| Chromosome B1 | |
|---|---|
| Marker | Position (cM) |
| BE806308 | 0.00 |
| B219_1 | 0.59 |
| A333_1 | 4.88 |
| T028_1 | 5.07 |
| K011_2 | 11.85 |
| Sat_272 | 14.32 |
| Bng061_1 | 16.10 |
| A588_1 | 16.70 |
| Sat_270 | 21.99 |
| OP_Q17 | 22.58 |
| A702_1 | 25.17 |
| Satt426 | 28.33 |
| A109_1 | 29.17 |
| Aco4 | 29.87 |
| Sat_411 | 30.87 |
| Mng415_1 | 31.78 |
| Satt509 | 32.50 |
| Sat_261 | 32.95 |
| Sat_156 | 35.00 |
| Satt251 | 36.48 |
| pcr2_168 | 37.25 |
| A381_2 | 37.75 |
| Satt638 | 37.79 |
| A129_1 | 38.63 |
| A632_1 | 38.68 |
| Bng158_1 | 39.63 |
| B031_1 | 39.63 |
| Bng182_1 | 39.95 |
| A847_1 | 40.08 |
| Satt197 | 46.38 |
| Sat_247 | 49.73 |
| H3_28 | 52.55 |
| Sat_128 | 53.41 |
| Sat_149 | 54.00 |
| A262_3 | 54.75 |
| T092_3 | 57.83 |
| Satt519 | 57.91 |
| A118_1 | 58.91 |
| A520_1 | 59.09 |
| A089_2 | 59.66 |
| A006_1 | 64.76 |
| Satt298 | 64.91 |
| BLT043_1 | 66.76 |
| mO011_1 | 71.23 |
| Sat_348 | 71.97 |

| Chromosome B1 | |
|---|---|
| Marker | Position (cM) |
| Satt597 | 73.76 |
| BLT019_2 | 74.57 |
| Sct_026 | 78.12 |
| G214_3 | 78.91 |
| Sat_360 | 80.19 |
| Satt332 | 80.88 |
| Sat_095 | 81.30 |
| L204_1 | 81.55 |
| Satt430 | 81.91 |
| Satt415 | 82.88 |
| Satt583 | 84.19 |
| Sat_364 | 84.25 |
| Satt444 | 85.91 |
| Satt665 | 96.36 |
| Sat_123 | 100.87 |
| Satt359 | 102.55 |
| S63860-CB | ~107 |
| R244_1 | 115.75 |
| Satt484 | 118.52 |
| H3_c6_1 | 121.13 |
| Satt453 | 123.95 |
| Sat_331 | 125.73 |
| A567_1 | 125.98 |
| BE801538 | 126.51 |
| AQ851479 | 128.66 |
| A598_1 | 131.38 |
| L050_1 | 131.80 |

Figure 6 (continued)

| Chromosome B2 | | Chromosome B2 | |
|---|---|---|---|
| Marker | Position (cM) | Marker | Position (cM) |
| BLT013_2 | 0.00 | Satt272 | 71.68 |
| Satt577 | 6.05 | Sat_230 | 72.08 |
| Sat_177 | 7.84 | Satt020 | 72.12 |
| A523_1 | 8.57 | Satt122 | 72.45 |
| V55b | 10.03 | BLT057_2 | 72.51 |
| A043_1 | 11.35 | Satt070 | 72.80 |
| Sat_264 | 12.56 | Sat_189 | 72.91 |
| A135_1 | 13.59 | Satt556 | 73.20 |
| L191_1 | 13.83 | DOP_F04 | 73.54 |
| A685_1 | 14.82 | L201_1 | 74.47 |
| Bng069_2 | 15.40 | Mng003_1 | 74.69 |
| Satt467 | 17.77 | B153_1 | 74.77 |
| T270_2 | 18.79 | Satt474 | 75.34 |
| Sat_342 | 20.30 | G214_5 | 75.80 |
| Satt126 | 27.62 | Sat_009 | 78.66 |
| G214_23 | 28.45 | Satt066 | 78.83 |
| A352_1 | 29.19 | B124_1 | 83.58 |
| Sat_287 | 31.87 | Mng474_1 | 83.91 |
| A242_1 | 33.13 | Satt534 | 87.58 |
| RGA_8 | 33.95 | Sct_064 | 89.30 |
| S60211-TB | 36.51 | AW620774 | 90.30 |
| A343_1 | 37.99 | A741_1 | 90.98 |
| OP_T02 | 38.00 | B194_1 | 91.69 |
| B142_1 | 43.58 | Satt063 | 93.48 |
| Sct_034 | 51.45 | Satt560 | 97.91 |
| Satt083 | 51.49 | mR048_1 | 98.08 |
| A018_1 | 53.54 | A593_1 | 98.54 |
| Satt168 | 55.20 | A516_1 | 99.02 |
| OP_E02a | 56.13 | Sat_424 | 100.09 |
| Satt416 | 56.95 | Satt726 | 100.55 |
| BLT049_2 | 59.82 | A234_1 | 102.37 |
| A329_1 | 62.74 | Mng247_1 | 104.12 |
| A509_1 | 63.68 | A519_1 | 104.73 |
| OPAF15a | 64.23 | M9E1mr3 | 110.44 |
| Satt304 | 65.55 | A404_2 | 110.69 |
| Sat_355 | 66.23 | A183_1 | 110.80 |
| M9E1mr1 | 66.80 | A427_1 | 110.95 |
| Satt601 | 67.73 | Satt687 | 113.61 |
| OP_C09 | 67.98 | B221_1 | 116.23 |
| Sat_182 | 68.63 | A230_1 | 116.32 |
| Sat_083 | 68.98 | H3_60 | 116.32 |
| Satt318 | 70.12 | G214_6 | 116.77 |
| Sct_094 | 70.55 | T005_1 | 118.69 |
| OP_D01c | 70.83 | Tel450 | 120.98 |
| G214_4 | 70.87 | | |

Figure 6 (continued)

| Chromosome C1 | | Chromosome C1 | |
|---|---|---|---|
| Marker | Position (cM) | Marker | Position (cM) |
| Satt565 | 0.00 | Satt294 | 78.65 |
| Satt690 | 5.36 | Sat_322 | 79.26 |
| Sct_186 | 9.02 | Satt476 | 80.62 |
| SOYGPATR | 10.34 | Sat_042 | 82.51 |
| A351_2 | 15.67 | Satt195 | 84.80 |
| K300_1 | 17.27 | Bng143_1 | 85.08 |
| A059_1 | 18.62 | Satt670 | 85.37 |
| A078_1 | 19.83 | Sat_207 | 87.30 |
| A463_1 | 21.04 | Satt713 | 88.94 |
| Satt396 | 24.11 | Sat_311 | 90.11 |
| Satt194 | 26.35 | A063_1 | 90.72 |
| Sat_367 | 28.04 | Sct_191 | 92.98 |
| Sat_337 | 32.09 | Sat_235 | 94.62 |
| K001_1 | 33.29 | Bng064_1 | 95.41 |
| V38b | 39.72 | Bng044_2 | 107.61 |
| Sat_140 | 41.43 | Bng012_1 | 108.08 |
| A946_1 | 41.97 | Satt524 | 120.12 |
| Bng019_1 | 53.86 | AI794821 | 122.62 |
| K472_1 | 53.91 | Satt338 | 123.79 |
| V38a | 54.18 | Satt682 | 127.05 |
| Satt578 | 65.08 | L014_1 | 127.38 |
| Satt607 | 67.02 | Satt180 | 127.76 |
| A519_3 | 69.30 | Satt164 | 132.46 |
| Bng140_1 | 69.68 | A074_1 | 133.97 |
| Satt646 | 70.51 | L175_1 | 135.61 |
| Bng161_1 | 70.57 | | |
| Dia | 71.08 | | |
| S00415-1-A | 71.24 | | |
| L192_1 | 73.16 | | |
| Satt190 | 73.32 | | |
| Satt161 | 73.38 | | |
| Satt718 | 73.79 | | |
| Sat_404 | 73.84 | | |
| Satt661 | 74.36 | | |
| Satt139 | 74.45 | | |
| AW277661 | 74.79 | | |
| Satt136 | 75.11 | | |
| Satt361 | 75.51 | | |
| Sat_077 | 76.00 | | |
| Satt399 | 76.23 | | |
| Sat_416 | 76.41 | | |
| Sat_357 | 76.43 | | |
| G214_25 | 76.43 | | |
| Sat_085 | 76.91 | | |
| G214_24 | 77.26 | | |

Figure 6 (continued)

| Chromosome C2 | |
|---|---|
| Marker | Position (cM) |
| A121_1 | 0.00 |
| Satt681 | 3.15 |
| AW734043 | 4.22 |
| Sat_130 | 11.39 |
| Bng035_1 | 15.36 |
| A122_1 | 17.10 |
| A059_2 | 21.71 |
| L199_2 | 23.34 |
| Bng132_2 | 23.99 |
| A262_4 | 25.07 |
| Satt227 | 26.65 |
| OP_E08 | 27.02 |
| Satt640 | 30.46 |
| Sat_062 | 30.79 |
| mQ086_1 | 34.16 |
| mO008_1 | 34.63 |
| Satt432 | 38.04 |
| Satt281 | 40.29 |
| Satt520 | 42.36 |
| Satt422 | 44.66 |
| Satt291 | 45.75 |
| A109_7 | 47.31 |
| Sat_336 | 51.84 |
| A655_1 | 52.20 |
| Satt457 | 56.50 |
| A338_1 | 56.59 |
| Sat_153 | 61.98 |
| A109_3 | 68.87 |
| Satt305 | 69.66 |
| Satt170 | 70.55 |
| X17120 | 75.20 |
| Bng228_1 | 74.18 |
| GMAC7L_SSR | 75.43 |
| K262_1 | 76.51 |
| K255_1 | 77.88 |
| Bng014_1 | 77.93 |
| A426_1 | 79.09 |
| Satt322 | 82.23 |
| L059_1 | 85.93 |
| Satt450 | 89.30 |
| Sat_213 | 90.93 |
| Sat_246 | 91.80 |
| B160_1 | 93.70 |
| Satt643 | 94.65 |
| A635_1 | 95.61 |

| Chromosome C2 | |
|---|---|
| Marker | Position (cM) |
| R092_3 | 96.12 |
| L148_1 | 97.19 |
| Satt376 | 97.83 |
| Satt363 | 98.07 |
| Sat_076 | 99.18 |
| Satt286 | 101.75 |
| A063_2 | 102.90 |
| Sat_402 | 103.33 |
| BLT032_1 | 103.77 |
| BLT053_9 | 106.17 |
| Sle28_1 | 106.76 |
| Satt277 | 107.58 |
| K011_3 | 109.26 |
| Bng164_1 | 110.13 |
| pcr2_150 | 110.73 |
| Satt365 | 111.68 |
| Satt205 | 112.18 |
| Satt557 | 112.19 |
| Satt289 | 112.34 |
| Satt134 | 112.83 |
| Sat_312 | 112.84 |
| Satt489 | 113.38 |
| Satt319 | 113.41 |
| Satt658 | 113.62 |
| AG36 | 113.69 |
| Satt100 | 113.95 |
| Sat_251 | 114.19 |
| L050_2 | 114.41 |
| A109_2 | 114.77 |
| Sat_142 | 115.09 |
| B131_1 | 115.19 |
| Satt708 | 115.48 |
| A397_1 | 116.72 |
| Sat_238 | 117.45 |
| Satt460 | 117.76 |
| Satt079 | 117.87 |
| Sat_263 | 118.77 |
| BLT029_1 | 119.47 |
| Staga001 | 119.84 |
| K365_1 | 120.41 |
| Satt307 | 121.26 |
| Sct_028 | 123.01 |
| A538_1 | 123.37 |
| P029_1 | 123.62 |
| K474_1 | 123.76 |

| Chromosome C2 | |
|---|---|
| Marker | Position (cM) |
| K474_2 | 124.02 |
| RGA_1e | 124.69 |
| Satt202 | 126.23 |
| Sat_252 | 127.00 |
| Satt316 | 127.66 |
| Satt433 | 128.22 |
| C056_1 | 129.53 |
| A748_1 | 131.75 |
| Satt371 | 145.47 |
| A676_1 | 148.61 |
| Satt357 | 151.91 |
| R183_2 | 157.88 |

Figure 6 (continued)

| Chromosome D1a | | Chromosome D1a | | Chromosome D1a | |
|---|---|---|---|---|---|
| Marker | Position (cM) | Marker | Position (cM) | Marker | Position (cM) |
| Tel1075a | 0.00 | pcr2_124 | 54.40 | K417_2 | 102.26 |
| Tel750 | 2.97 | Satt603 | 54.50 | Bng057_1 | 103.04 |
| Sat_332 | 5.25 | A109_5 | 54.79 | D1 | 103.44 |
| Sat_413 | 5.93 | Satt295 | 55.22 | Sat_160 | 104.27 |
| A398_1 | 6.43 | A235_2 | 55.45 | Satt408 | 106.69 |
| R153_1 | 9.32 | Satt515 | 55.68 | Satt147 | 108.88 |
| L031_1 | 9.35 | Sat_201 | 56.08 | Satt129 | 109.66 |
| Me | 9.40 | Satt179 | 56.20 | L058_1 | 111.12 |
| Mng307_1 | 14.66 | Satt254 | 56.43 | Bng098_1 | 113.01 |
| Satt184 | 17.52 | Satt383 | 56.57 | B219_2 | 114.37 |
| M373_1 | 20.24 | Sle3_14 | 57.02 | C063_1 | 114.87 |
| Bng090_1 | 23.37 | Satt267 | 57.34 | Pd1 | 120.88 |
| Bng097_1 | 25.51 | NP008_1 | 57.75 | | |
| K019_1 | 30.29 | Satt402 | 57.75 | | |
| OP_I10 | 32.82 | AZ302047 | 57.75 | | |
| pcr2_153 | 34.06 | Satt203 | 59.00 | | |
| A947_1 | 34.50 | Sle_002 | 59.59 | | |
| K478_1 | 34.91 | K395_1 | 59.99 | | |
| Sat_353 | 36.23 | Satt283 | 60.97 | | |
| R013_2 | 38.09 | Satt370 | 60.99 | | |
| A691_1 | 40.83 | DUBC204 | 61.32 | | |
| Satt531 | 40.86 | Satt580 | 62.36 | | |
| B214_1 | 41.47 | Sat_110 | 62.52 | | |
| B186_1 | 42.11 | Sat_343 | 62.56 | | |
| R249_1 | 43.66 | Satt507 | 64.51 | | |
| Satt368 | 43.84 | Sat_345 | 65.62 | | |
| Satt482 | 45.75 | Sle3_4 | 66.13 | | |
| OP_S16 | 46.16 | Sat_106 | 66.38 | | |
| Satt320 | 46.79 | AW781285 | 67.77 | | |
| Satt221 | 47.04 | Satt198 | 68.62 | | |
| Satt360 | 47.59 | Satt468 | 69.91 | | |
| Satt605 | 47.73 | Satt436 | 70.69 | | |
| Satt342 | 48.13 | Satt439 | 72.26 | | |
| Satt032 | 48.63 | Sat_036 | 75.25 | | |
| Satt532 | 49.07 | Satt077 | 77.48 | | |
| Satt502 | 49.84 | Sat_414 | 85.48 | | |
| Sat_159 | 50.08 | Mng287_1 | 87.47 | | |
| Satt321 | 50.16 | A295_1 | 87.80 | | |
| Satt169 | 50.54 | Sat_305 | 91.26 | | |
| Satt548 | 51.07 | Bng074_1 | 93.88 | | |
| K227_2 | 51.08 | K647_1 | 94.87 | | |
| kT_1 | 52.08 | Bng119_1 | 95.63 | | |
| Mng474_2 | 52.23 | Satt407 | 99.58 | | |
| A109_8 | 52.91 | Satt071 | 100.38 | | |
| Sat_346 | 53.66 | G | 100.80 | | |

Figure 6 (continued)

| Chromosome D1b | |
|---|---|
| Marker | Position (cM) |
| Sat_096 | 0.00 |
| Sat_279 | 3.79 |
| A725_1 | 8.63 |
| Satt216 | 9.80 |
| Sat_227 | 11.14 |
| L216_1 | 15.46 |
| Sat_351 | 20.61 |
| Satt095 | 25.60 |
| Wc | 27.13 |
| BE021153 | 30.23 |
| BE475343 | 30.74 |
| Sat_373 | 35.75 |
| Satt157 | 37.07 |
| Sat_211 | 38.04 |
| Satt698 | 38.04 |
| Sat_173 | 38.63 |
| Satt701 | 40.04 |
| Satt558 | 43.91 |
| Satt634 | 46.61 |
| Sat_254 | 46.91 |
| BF070293 | 47.27 |
| AI856415 | 50.11 |
| Satt296 | 52.61 |
| Satt542 | 53.02 |
| Satt266 | 59.61 |
| A605_1 | 64.91 |
| Sat_423 | 67.62 |
| A747_1 | 69.18 |
| Sat_135 | 70.65 |
| Satt412 | 72.57 |
| Satt141 | 72.88 |
| Satt290 | 73.34 |
| Satt611 | 74.01 |
| Satt604 | 74.20 |
| K011_4 | 74.55 |
| Satt506 | 74.79 |
| Satt005 | 75.29 |
| Satt600 | 75.41 |
| L050_3 | 75.44 |
| Satt537 | 75.66 |
| Satt579 | 75.94 |
| Satt282 | 76.09 |
| Sat_089 | 76.27 |
| Satt189 | 76.32 |
| Satt350 | 76.59 |

| Chromosome D1b | |
|---|---|
| Marker | Position (cM) |
| Satt428 | 77.34 |
| Mng137_1 | 77.55 |
| Bng047_1 | 77.87 |
| Sat_169 | 78.44 |
| Satt644 | 79.41 |
| S00705-1-A | 83.80 |
| Satt041 | 84.04 |
| RGA_1f | 85.14 |
| Satt546 | 87.19 |
| M7E8mr2 | 87.80 |
| B194_2 | 88.36 |
| Sat_139 | 93.34 |
| Satt703 | 98.75 |
| Satt172 | 100.88 |
| Sat_069 | 102.59 |
| Idh1 | 105.41 |
| A519_2 | 107.61 |
| Sat_183 | 112.62 |
| OPAM15c | 113.68 |
| Satt274 | 116.34 |
| G214_7 | 117.02 |
| L161_1 | 117.44 |
| Satt459 | 118.62 |
| Sat_202 | 118.86 |
| Sat_198 | 118.94 |
| K411_1 | 119.33 |
| A343_2 | 120.97 |
| T270_1 | 123.33 |
| Staga002 | 126.44 |
| B139_1 | 128.39 |
| Sat_415 | 130.47 |
| Sat_289 | 131.91 |
| A135_2 | 132.44 |
| BLT013_2 | 133.61 |
| Sat_192 | 135.25 |
| Sat_283 | 136.66 |
| Satt271 | 137.05 |
| Satg001 | 137.97 |

Figure 6 (continued)

| Chromosome D2 | | Chromosome D2 | |
|---|---|---|---|
| Marker | Position (cM) | Marker | Position (cM) |
| A095_1 | 0.00 | Satt514 | 85.69 |
| Sctt008 | 3.16 | Fr2 | 86.19 |
| Sat_333 | 5.83 | Satt528 | 86.33 |
| Sat_296 | 6.42 | K286_1 | 86.58 |
| L072_1 | 7.80 | Sat_362 | 86.69 |
| BLT032_2 | 9.21 | Sat_194 | 86.69 |
| A064_2 | 9.95 | Sat_338 | 87.16 |
| A257_1 | 10.35 | Satt082 | 87.25 |
| Sct_192 | 11.77 | Sat_365 | 87.38 |
| Satt328 | 16.76 | Sat_300 | 87.55 |
| A401_2 | 17.18 | Satt574 | 87.66 |
| G214_8 | 18.42 | Satt662 | 87.87 |
| A124_1 | 22.45 | Satt543 | 88.01 |
| B146_1 | 22.96 | Satt488 | 89.19 |
| Satt458 | 24.52 | Satt464 | 89.75 |
| Satt135 | 26.04 | L026_1 | 90.66 |
| Sat_277 | 28.79 | Satt615 | 91.20 |
| Satt014 | 29.55 | Sat_001 | 92.12 |
| Sat_284 | 30.79 | G214_9 | 92.66 |
| Satt498 | 32.13 | Sat_354 | 93.70 |
| Satt486 | 34.09 | Satt301 | 93.70 |
| Satt372 | 39.34 | i6_2 | 93.91 |
| Mdh | 43.18 | K011_5 | 95.41 |
| Satt002 | 47.73 | OPAD11c | 95.55 |
| Satt443 | 51.41 | BLT049_3 | 97.51 |
| Satt582 | 53.84 | GMHSP179_SSR | 99.04 |
| OP_M15 | 55.59 | L204_2 | 100.12 |
| Satt154 | 57.07 | Satt186 | 105.44 |
| Sat_092 | 57.50 | Satt310 | 107.48 |
| A083_1 | 62.54 | OP_F14 | 109.48 |
| M9E1mr2 | 64.57 | Sat_326 | 112.84 |
| Satt447 | 66.26 | Satt413 | 113.61 |
| Satt669 | 67.70 | Satt672 | 114.97 |
| Satt208 | 67.91 | Satt031 | 115.69 |
| Satt397 | 69.30 | A141_1 | 117.11 |
| K258_2 | 73.51 | Sat_086 | 118.66 |
| Sat_292 | 75.29 | Sat_022 | 120.30 |
| pcr2_182 | 75.41 | Satt256 | 124.30 |
| Sat_222 | 76.69 | Satt386 | 125.00 |
| Satt389 | 79.23 | Sat_220 | 128.72 |
| Satt461 | 80.19 | Sct_137 | 128.94 |
| Sat_114 | 84.18 | Tel3ABCa | 133.85 |
| Satt311 | 84.62 | | |
| Satt226 | 85.15 | | |
| Sat_209 | 85.63 | | |

Figure 6 (continued)

| Chromosome E | |
|---|---|
| Marker | Position (cM) |
| T183_1 | 0.00 |
| A135_3 | 0.06 |
| Satt575 | 3.30 |
| Satt213 | 3.72 |
| SAC7_1 | 6.30 |
| Sat_112 | 8.67 |
| A242_2 | 11.02 |
| Satt411 | 12.92 |
| Pb | 13.60 |
| T153_2 | 14.96 |
| Bng027_1 | 15.41 |
| Sat_124 | 15.86 |
| A963_1 | 17.12 |
| G214_10 | 17.45 |
| pcr2_188 | 18.19 |
| Satt512 | 18.73 |
| Satt384 | 19.29 |
| Satt691 | 19.70 |
| L194_2 | 20.00 |
| T092_2 | 20.05 |
| Satt720 | 20.79 |
| A053_1 | 21.04 |
| A086_1 | 21.90 |
| OP_M12b | 22.84 |
| A636_1 | 25.95 |
| A517_1 | 26.02 |
| R051_1 | 27.00 |
| A458_1 | 27.00 |
| A455_1 | 27.02 |
| Bng193_1 | 28.15 |
| A646_1 | 28.15 |
| K229_1 | 28.27 |
| B174_1 | 30.87 |
| A454_1 | 30.88 |
| Satt651 | 32.09 |
| Satt212 | 32.27 |
| Satt598 | 34.20 |
| A203_1 | 34.61 |
| Satt573 | 35.79 |
| OP_M02b | 36.79 |
| A374_1 | 37.29 |
| A656_1 | 37.33 |
| Sat_136 | 39.16 |
| Satt606 | 39.77 |
| A386_1 | 39.98 |

| Chromosome E | |
|---|---|
| Marker | Position (cM) |
| Satt699 | 41.24 |
| Satt602 | 41.68 |
| K274_1 | 42.27 |
| Sat_172 | 42.74 |
| Sat_107 | 43.04 |
| Satt204 | 43.13 |
| Sat_380 | 43.29 |
| Satt706 | 43.36 |
| Satt491 | 43.63 |
| OPAG19 | 44.02 |
| Satt268 | 44.27 |
| A510_5 | 44.36 |
| G214_11 | 44.52 |
| OPAN07 | 44.54 |
| pcr2_1101 | 44.68 |
| Satt185 | 44.75 |
| Satt151 | 44.93 |
| Satt403 | 44.93 |
| Satt483 | 44.98 |
| Satt452 | 45.09 |
| Satt355 | 45.15 |
| Satt263 | 45.40 |
| Satt716 | 45.63 |
| Satt117 | 45.77 |
| Satt724 | 45.88 |
| R028_2 | 46.09 |
| BLT049_5 | 46.27 |
| Satt045 | 46.65 |
| A598_2 | 47.09 |
| Sat_273 | 47.50 |
| B124_3 | 47.54 |
| G214_26 | 47.57 |
| DOP_G06 | 48.43 |
| S123-126 | 48.61 |
| A427_3 | 48.75 |
| Bng107_1 | 49.22 |
| G214_12 | 49.91 |
| R013_1 | 50.09 |
| K477_1 | 50.41 |
| L163_1 | 50.77 |
| OPAG03 | 51.43 |
| B2 | 51.95 |
| OP_K16 | 52.07 |
| A597_1 | 52.61 |
| A226H_2 | 54.85 |

| Chromosome E | |
|---|---|
| Marker | Position (cM) |
| Satt369 | 56.27 |
| Satt685 | 56.70 |
| OP_D01 | 59.11 |
| OP_N14 | 60.09 |
| A111_2 | 62.84 |
| A711_1 | 63.18 |
| A136_2 | 63.91 |
| Sat_381 | 64.18 |
| C009_1 | 65.08 |
| BE347343 | 65.66 |
| Satt553 | 67.91 |
| Sat_376 | 69.23 |
| Satt231 | 70.23 |
| Satt230 | 71.30 |

Figure 6 (continued)

| Chromosome F | | Chromosome F | | Chromosome F | |
|---|---|---|---|---|---|
| Marker | Position (cM) | Marker | Position (cM) | Marker | Position (cM) |
| GMRUBP_SSR | 0.00 | Bng075_1 | 46.61 | E049_2 | 93.38 |
| M8E6mr1 | 1.09 | Mng228_1 | 46.91 | Satt490 | 97.97 |
| Sat_390 | 1.79 | K002_1 | 47.63 | Satt144 | 102.08 |
| Satt146 | 1.92 | Satt595 | 50.24 | L195_2 | 102.76 |
| Satt325 | 2.23 | Sat_133 | 50.77 | Sat_197 | 103.51 |
| DOP_A04 | 2.77 | B202_1 | 51.25 | B148_1 | 105.83 |
| Satt343 | 3.04 | K265_1 | 51.50 | K014_2 | 106.36 |
| Sat_387 | 3.11 | Bng004_1 | 52.97 | Satt554 | 111.88 |
| Satt569 | 3.35 | K314_1 | 53.54 | A566_1 | 114.09 |
| Satt193 | 3.42 | Satt663 | 56.16 | Satt657 | 116.91 |
| Satt586 | 3.63 | Bng118_1 | 56.75 | Satt218 | 117.65 |
| Satt030 | 3.95 | Sat_103 | 57.77 | Satt522 | 119.19 |
| G214_13 | 4.67 | Sat_297 | 59.59 | AW756935 | 124.87 |
| Satt649 | 5.36 | BLT025_1 | 59.77 | T092_1 | 126.44 |
| K250_1 | 6.69 | Mng157_1 | 61.81 | Sat_090 | 130.63 |
| j11_1 | 7.31 | Sat_229 | 62.79 | Bng172_1 | 132.61 |
| BLT030_1 | 8.67 | A757_1 | 63.11 | Satt656 | 135.11 |
| Sat_262 | 9.69 | Satt114 | 63.68 | Sat_417 | 135.94 |
| OPAN06 | 10.09 | A186_1 | 64.84 | K102_2 | 138.28 |
| Satt145 | 10.65 | L063_1 | 65.55 | Sat_074 | 142.35 |
| Satt269 | 11.37 | Sat_234 | 66.55 | Satt395 | 146.41 |
| Satt348 | 15.29 | Rpg1 | 66.98 | OPAV06b | 150.97 |
| Satt252 | 16.08 | K644_1 | 67.18 | | |
| Satt149 | 18.12 | L28831 | 67.52 | | |
| BLT010_1 | 19.27 | SOYHSP176 | 68.44 | | |
| Satt423 | 20.55 | Sat_154 | 68.91 | | |
| AW186493 | 21.04 | BLT053_7 | 69.00 | | |
| BE806387 | 22.96 | B212_1 | 69.83 | | |
| Sat_240 | 25.58 | R045_1 | 70.12 | | |
| Satt659 | 26.70 | Satt510 | 71.41 | | |
| Satt206 | 26.98 | L050_14 | 71.41 | | |
| Sat_039 | 27.87 | K007_2 | 72.73 | | |
| W1 | 28.86 | Sat_317 | 72.97 | | |
| BLT057_1 | 30.84 | Sct_033 | 74.12 | | |
| DUBC767 | 31.55 | Sat_120 | 75.97 | | |
| Sat_298 | 32.32 | Satt335 | 77.69 | | |
| Satt160 | 33.18 | Satt334 | 78.05 | | |
| A401_1 | 39.08 | A708_1 | 84.16 | | |
| K390_1 | 40.36 | Satt362 | 82.83 | | |
| A806_1 | 40.38 | Sct_188 | 85.33 | | |
| Sat_309 | 41.47 | Satt072 | 87.01 | | |
| Satt374 | 43.00 | Sat_375 | 88.08 | | |
| Satt425 | 43.43 | B1 | 89.88 | | |
| Satt516 | 44.41 | Bng190_1 | 91.68 | | |
| G248_2 | 46.16 | Sat_313 | 91.87 | | |

Figure 6 (continued)

| Chromosome G | | Chromosome G | | Chromosome G | |
|---|---|---|---|---|---|
| Marker | Position (cM) | Marker | Position (cM) | Marker | Position (cM) |
| Satt163 | 0.00 | Satt131 | 48.91 | A890_1 | 67.69 |
| Satt214 | 0.50 | Satt566 | 49.91 | Sat_164 | 68.66 |
| Satt038 | 1.84 | L002_1 | 50.34 | Satt503 | 68.76 |
| Satt275 | 2.20 | Satt352 | 50.52 | Satt517 | 69.87 |
| H3_c6_2 | 2.77 | Satt427 | 51.68 | Sat_143 | 73.41 |
| Sat_210 | 3.70 | DUBC423 | 52.32 | Mng273_2 | 74.00 |
| Sat_168 | 3.90 | Satt594 | 52.93 | Satt288 | 76.76 |
| Satt309 | 4.53 | Satt303 | 53.41 | A121_2 | 78.05 |
| B053_1 | 5.77 | OP_F07 | 54.00 | A885_1 | 79.23 |
| AZ254740 | 8.23 | A148_1 | 54.43 | Satt612 | 80.37 |
| Bng122_1 | 8.56 | K443_1 | 54.47 | K493_1 | 80.58 |
| Sat_141 | 9.18 | mP238_1 | 55.47 | T005_2 | 81.47 |
| Sat_163 | 10.06 | A020_1 | 55.66 | bacF11Rhnd | 84.87 |
| Satt356 | 12.18 | Satt138 | 55.99 | OP_M02a | 86.13 |
| Satt688 | 12.54 | Sat_094 | 56.18 | p28_13_2 | 86.98 |
| Satt570 | 12.74 | Satt533 | 56.52 | AF162283 | 87.94 |
| AW734137 | 15.63 | A426_3 | 56.74 | A245_2 | 89.97 |
| Satt217 | 18.25 | R092_1 | 56.81 | OPAD08 | 93.00 |
| Satt235 | 21.88 | Satt564 | 57.32 | Sct_199 | 94.40 |
| Satt130 | 23.10 | Sat_088 | 58.00 | Satt472 | 94.83 |
| K069_1 | 24.09 | A427_2 | 58.70 | Satt191 | 96.57 |
| Sat_315 | 27.48 | Satt504 | 59.83 | A235_1 | 97.23 |
| Sat_290 | 29.03 | OP_M09 | 60.04 | L002_2 | 97.69 |
| Bng225_2 | 29.27 | Sat_185 | 60.36 | OP_H04 | 97.88 |
| Sat_131 | 31.33 | B151_1 | 60.52 | H3_54HE_1 | 98.50 |
| Satt324 | 33.25 | G214_14 | 61.20 | L154_1 | 99.33 |
| Sat_403 | 34.86 | Sat_260 | 61.41 | Sat_117 | 100.00 |
| A112_1 | 35.50 | Sat_223 | 61.63 | A690_2 | 105.87 |
| OP_E02b | 37.98 | OPAJ11a | 62.02 | Bng069_1 | 105.88 |
| OPAE12 | 39.79 | Sat_203 | 62.08 | Sct_187 | 107.11 |
| BLT036_2 | 40.73 | Satt199 | 62.16 | Sat_372 | 107.75 |
| OP_S09 | 40.93 | Satt505 | 63.00 | Sat_064 | 108.69 |
| L156_1 | 42.06 | Satt400 | 63.27 | A378_1 | 109.48 |
| Sat_308 | 43.09 | Stel_1 | 64.10 | L183_1 | 110.23 |
| Satt394 | 43.38 | B151_2 | 64.62 | L120_1 | 110.44 |
| Satt115 | 43.77 | i8_3 | 64.68 | A586_2 | 111.19 |
| OPAM15a | 43.88 | Mng217_1 | 65.01 | Mpi | 113.02 |
| A510_6 | 45.06 | Sle_001 | 65.01 | L050_11 | 113.12 |
| Sat_358 | 45.49 | p40_5_1 | 65.01 | A681_1 | 116.76 |
| Sctt010 | 45.86 | Mng078_1 | 65.01 | | |
| R017_1 | 46.34 | Mng177_1 | 65.01 | | |
| Satt501 | 47.27 | A584_1 | 65.55 | | |
| Satt340 | 48.54 | A073_1 | 65.55 | | |
| L050_4 | 48.88 | Satt012 | 66.55 | | |
| OP_U09a | 48.91 | A816_1 | 67.52 | | |

Figure 6 (continued)

| Chromosome H | |
|---|---|
| Marker | Position (cM) |
| Bng154_1 | 0.00 |
| Satt666 | 0.59 |
| L185_3 | 1.80 |
| Sat_214 | 2.85 |
| Sat_200 | 3.02 |
| Bng067_1 | 3.04 |
| Satt635 | 4.88 |
| A141_2 | 5.30 |
| U08405 | 7.26 |
| Pv7 | 7.83 |
| Satt353 | 8.48 |
| A381_1 | 11.25 |
| R249_2 | 15.93 |
| A132_1 | 19.83 |
| A262_5 | 23.46 |
| H3_28_2 | 24.75 |
| Satt568 | 27.63 |
| Sat_127 | 28.79 |
| K009_1 | 33.02 |
| A069_1 | 33.16 |
| A089_1 | 33.63 |
| A036_1 | 34.29 |
| Sctt009 | 38.88 |
| Bng145_1 | 40.82 |
| Satt192 | 44.04 |
| Satt442 | 46.95 |
| pcr2_175 | 48.43 |
| BLT053_3 | 48.74 |
| A703_1 | 50.86 |
| BLT046_1 | 51.00 |
| Satt541 | 53.34 |
| A404T_3 | 55.40 |
| A130_1 | 56.18 |
| Satt469 | 58.91 |
| Sat_334 | 59.00 |
| A404_1 | 60.18 |
| Sat_122 | 61.33 |
| Sat_118 | 61.86 |
| A131_2 | 62.36 |
| RGA_9 | 62.73 |
| RGA_4 | 63.44 |
| bac50e | 63.59 |
| DUBC413 | 63.77 |
| Satt052 | 64.09 |
| JOP_C07 | 65.43 |

| Chromosome H | |
|---|---|
| Marker | Position (cM) |
| Sat_401 | 66.20 |
| Satt253 | 67.16 |
| Sat_206 | 67.79 |
| Satt222 | 68.08 |
| Sat_205 | 68.18 |
| Satt279 | 68.50 |
| Satt676 | 68.86 |
| Satt314 | 69.12 |
| Mng374_1 | 70.87 |
| Bng202_1 | 71.32 |
| Bng104_1 | 71.73 |
| Satt629 | 72.18 |
| BLT019_1 | 72.77 |
| Sat_158 | 73.45 |
| K327_1 | 77.52 |
| Ps | 78.44 |
| Satt302 | 81.04 |
| Sat_175 | 83.19 |
| B069_1 | 84.13 |
| Sat_216 | 85.26 |
| Satt637 | 85.79 |
| Satt142 | 86.48 |
| Satt293 | 89.08 |
| Satt317 | 89.51 |
| A748_2 | 90.25 |
| Satt181 | 91.12 |
| P13158A | 96.00 |
| A810_1 | 97.52 |
| Sat_218 | 99.50 |
| Sat_180 | 104.37 |
| Satt434 | 105.73 |
| RGA_6c | 110.43 |
| K007_1 | 113.23 |
| A162_1 | 115.33 |
| A570_1 | 117.09 |
| L195_1 | 119.41 |
| K014_1 | 121.29 |
| A858_1 | 124.00 |
| B072_1 | 124.05 |

Figure 6 (continued)

| Chromosome I | |
|---|---|
| Marker | Position (cM) |
| T098_1 | 0.00 |
| Satt571 | 18.50 |
| Satt451 | 20.34 |
| Satt419 | 21.90 |
| Satt562 | 22.84 |
| Enp | 23.92 |
| Satt367 | 27.98 |
| Satt587 | 31.49 |
| Satt614 | 31.94 |
| A688_1 | 32.40 |
| A144_1 | 32.41 |
| Sctt012 | 33.98 |
| A352_2 | 34.66 |
| Satt700 | 35.02 |
| AB002807 | 35.16 |
| Satt127 | 35.34 |
| Sat_219 | 36.02 |
| Satt496 | 36.40 |
| Sat_174 | 36.59 |
| Satt239 | 36.93 |
| L204_3 | 37.29 |
| L185_1 | 37.49 |
| K011_1 | 38.06 |
| Mng371_1 | 38.27 |
| A407_1 | 39.41 |
| i6_1 | 39.93 |
| A109_4 | 40.09 |
| A109_6 | 40.43 |
| A515_1 | 44.04 |
| Satt354 | 46.22 |
| Sat_105 | 49.34 |
| Satt270 | 50.11 |
| Ln | 50.36 |
| A955_1 | 51.99 |
| L048_1 | 54.79 |
| Sat_268 | 55.09 |
| Satt049 | 58.82 |
| Satt650 | 63.33 |
| K644_2 | 64.87 |
| Sat_104 | 65.62 |
| OPAF15b | 65.83 |
| T010_2 | 67.29 |
| Satt671 | 72.08 |
| Sat_418 | 74.26 |
| Sat_170 | 75.00 |

| Chromosome I | |
|---|---|
| Marker | Position (cM) |
| Satt330 | 77.83 |
| A102_1 | 79.50 |
| Sat_421 | 81.40 |
| Satt292 | 82.77 |
| Sat_324 | 84.48 |
| Satt162 | 86.73 |
| Satt623 | 92.51 |
| A007_1 | 95.13 |
| GMGLPSI2_SSR | 97.04 |
| Sat_155 | 98.05 |
| Sat_419 | 98.11 |
| Sat_420 | 98.38 |
| Sat_299 | 99.83 |
| Satt148 | 100.77 |
| OP_Y10 | 102.23 |
| K287_1 | 103.05 |
| B039_1 | 104.44 |
| AQ851518 | 106.80 |
| Chi | 111.98 |
| Satt440 | 112.69 |
| Sct_189 | 113.76 |
| K011_6 | 115.69 |
| Bng155_1 | 115.79 |
| A644_1 | 116.25 |
| Bng168_1 | 116.58 |
| L050_5 | 118.02 |
| A664_2 | 118.16 |
| L026_2 | 119.08 |
| A510_3 | 125.18 |

Figure 6 (continued)

| Chromosome J | | Chromosome J | | Chromosome J | |
|---|---|---|---|---|---|
| Marker | Position (cM) | Marker | Position (cM) | Marker | Position (cM) |
| Bng179_1 | 0.00 | Sct_193 | 41.50 | Sat_395 | 89.48 |
| B101_1 | 2.24 | L216_2 | 41.72 | Satt712 | 89.61 |
| Bng202_2 | 4.05 | Satt529 | 41.90 | Sat_393 | 90.33 |
| AW310961 | 5.19 | Sat_165 | 42.20 | A199_2 | 91.16 |
| i1_2 | 6.36 | Satt622 | 42.25 | | |
| A363_2 | 7.87 | Satt183 | 42.50 | | |
| Satt249 | 11.74 | G173_2 | 42.65 | | |
| Satt405 | 12.41 | Satt380 | 43.00 | | |
| B046_2 | 13.95 | Sat_255 | 43.84 | | |
| Satt287 | 15.69 | Satt215 | 44.08 | | |
| Satt674 | 15.95 | Sat_361 | 44.49 | | |
| B074_1 | 17.35 | Sct_001 | 44.68 | | |
| A204_1 | 18.48 | Sat_093 | 46.09 | | |
| pcr2_1901 | 20.41 | A109_9 | 46.66 | | |
| A060_1 | 20.79 | Sat_366 | 52.84 | | |
| mO109_1 | 22.78 | Sat_350 | 55.73 | | |
| E107_1 | 22.87 | RGA_3 | 55.81 | | |
| Sat_228 | 23.91 | B122_1 | 57.20 | | |
| Sct_046 | 24.09 | Bng063_1 | 57.40 | | |
| Satt285 | 25.51 | bac27T | 61.33 | | |
| B166_1 | 27.62 | Sctt011 | 62.88 | | |
| Sat_339 | 27.96 | RGA_2a | 63.00 | | |
| K384_1 | 28.12 | Satt244 | 65.04 | | |
| A450_1 | 29.37 | pcr2_135 | 66.50 | | |
| Sct_065 | 32.09 | Satt547 | 67.79 | | |
| Satt693 | 33.88 | K375_1 | 68.12 | | |
| p40_2_2 | 33.93 | Sat_396 | 69.30 | | |
| BLT049_4 | 34.61 | R189_1 | 69.75 | | |
| Bng044_1 | 34.66 | JOP_E01 | 69.83 | | |
| K011_9 | 35.59 | L050_10 | 71.51 | | |
| Satt414 | 37.04 | G815_1 | 73.73 | | |
| Sat_370 | 37.40 | B032_1 | 74.04 | | |
| Satt654 | 38.09 | Sat_224 | 75.12 | | |
| Satt406 | 38.18 | Satt431 | 78.57 | | |
| Satt280 | 38.70 | JOP_F10 | 80.55 | | |
| Satt132 | 39.18 | RGA_1a | 81.56 | | |
| Satt596 | 39.63 | A233_1 | 83.15 | | |
| Scaa003 | 39.95 | A724_1 | 84.88 | | |
| Sat_259 | 40.34 | RGA_1b | 86.31 | | |
| Satt686 | 40.50 | bac91f11U2 | 86.48 | | |
| Satt456 | 40.83 | A132_3 | 87.09 | | |
| Sat_412 | 41.11 | pcr2_176 | 87.91 | | |
| L050_6 | 41.13 | bac91f11U1 | 88.52 | | |
| BLT049_6 | 41.20 | RGA_1c | 89.23 | | |
| Sat_151 | 41.34 | Sat_394 | 89.43 | | |

Figure 6 (continued)

| Chromosome K | | Chromosome K | | Chromosome K | |
|---|---|---|---|---|---|
| Marker | Position (cM) | Marker | Position (cM) | Marker | Position (cM) |
| K401_1 | 0.00 | Sat_363 | 50.58 | M7E8mr3 | 106.51 |
| Satt715 | 0.91 | Satt673 | 50.79 | Sat_126 | 108.19 |
| Satt539 | 1.80 | Satt617 | 50.93 | E014_2 | 110.19 |
| Sat_087 | 4.85 | Satt710 | 51.00 | P1 | 111.29 |
| Ep | 10.17 | Satg002 | 51.45 | Bng007_1 | 112.93 |
| Satt242 | 14.35 | Sat_116 | 52.27 | Satt588 | 117.01 |
| Sat_119 | 17.11 | Satt240 | 52.88 | | |
| MS_B13_1 | 19.75 | A510_2 | 53.99 | | |
| P049_1 | 26.91 | Sat_325 | 54.00 | | |
| A315_1 | 28.71 | K418_2 | 54.70 | | |
| Satt102 | 30.28 | Satt559 | 54.97 | | |
| R051_2 | 31.75 | Sat_111 | 55.70 | | |
| Satt055 | 32.95 | Satt273 | 56.61 | | |
| Satt137 | 36.99 | Satt725 | 56.84 | | |
| Satt178 | 40.86 | Sat_044 | 58.00 | | |
| Satt349 | 42.38 | B032_2 | 59.32 | | |
| Satt555 | 42.70 | JOP_A20 | 60.16 | | |
| Sct_196 | 43.04 | OPAT12 | 60.32 | | |
| Satt544 | 43.34 | Sat_043 | 61.66 | | |
| Satt247 | 43.95 | A199_1 | 67.73 | | |
| Sat_399 | 44.66 | Satt499 | 71.01 | | |
| G214_22 | 44.75 | DUBC300 | 71.59 | | |
| Satt381 | 44.99 | Bng224_1 | 75.23 | | |
| Sat_281 | 45.13 | Sct_190 | 77.37 | | |
| Satt046 | 45.59 | Satt475 | 78.68 | | |
| Satt167 | 45.74 | Satt260 | 80.12 | | |
| Satt375 | 45.81 | mP238_2 | 83.05 | | |
| Satt124 | 46.18 | K003_1 | 84.54 | | |
| Satt417 | 46.20 | Sat_167 | 85.19 | | |
| Satt441 | 46.20 | A670_1 | 85.95 | | |
| Satt264 | 46.25 | OPAD11 | 86.48 | | |
| Satt552 | 46.43 | Sat_243 | 86.77 | | |
| G214_15 | 46.47 | A841_1 | 87.04 | | |
| Satt518 | 46.63 | BLT053_6 | 89.20 | | |
| Satt727 | 46.79 | Sat_352 | 93.63 | | |
| SOYPRP1 | 46.93 | A668_1 | 95.88 | | |
| C009_2 | 47.16 | R | 97.12 | | |
| Satt337 | 47.38 | K387_1 | 98.87 | | |
| Satt326 | 49.52 | Sat_293 | 99.09 | | |
| Satt628 | 49.59 | K266_1 | 100.48 | | |
| Fr1 | 49.93 | A661_1 | 102.44 | | |
| Sat_349 | 50.31 | Sat_020 | 103.59 | | |
| Satt001 | 50.56 | Satt196 | 104.79 | | |

Figure 6 (continued)

| Chromosome L | | Chromosome L | | Chromosome L | |
|---|---|---|---|---|---|
| Marker | Position (cM) | Marker | Position (cM) | Marker | Position (cM) |
| Satt495 | 0.00 | B164_1 | 35.29 | A537_1 | 103.72 |
| Satt723 | 1.07 | G214_16 | 35.34 | Satt513 | 106.37 |
| Sat_408 | 1.31 | Satt613 | 36.04 | Satt373 | 107.23 |
| A169_1 | 3.64 | A023_1 | 36.70 | Bng088_1 | 109.33 |
| Sle3_4s | 6.19 | Satt284 | 38.16 | A802_2 | 111.07 |
| BLT010_2 | 7.85 | AW508247 | 38.83 | B174_2 | 111.47 |
| BLT007_1 | 9.44 | Satt462 | 41.00 | G214_21 | 112.16 |
| Satt232 | 10.35 | L050_7 | 42.75 | A363_1 | 112.51 |
| Sat_301 | 11.12 | E014_1 | 45.34 | Sat_245 | 115.07 |
| Satt446 | 11.47 | A071_5 | 46.04 | | |
| Satt182 | 14.03 | B046_1 | 46.40 | | |
| R176_1 | 14.90 | L1 | 48.27 | | |
| JUBC090 | 15.62 | B162_2 | 49.40 | | |
| Satt238 | 19.93 | A071_1 | 52.38 | | |
| Sat_071 | 20.78 | peG488_1 | 53.25 | | |
| BLT039_1 | 21.63 | p28_10_2 | 53.50 | | |
| Bng071_1 | 22.07 | Sat_150 | 53.66 | | |
| Satt388 | 23.54 | Satt481 | 54.57 | | |
| A264_1 | 27.04 | Sat_340 | 55.50 | | |
| RGA_7 | 27.07 | Satt156 | 56.13 | | |
| Satt523 | 27.92 | Sct_010 | 59.52 | | |
| Sat_134 | 28.27 | Satt076 | 61.34 | | |
| i8_2 | 28.90 | Satt448 | 64.66 | | |
| A450_2 | 29.42 | gy3E_1 | 65.51 | | |
| A106_1 | 29.59 | Satt166 | 66.51 | | |
| Sat_405 | 29.62 | Sat_113 | 68.26 | | |
| Satt143 | 30.19 | Satt678 | 70.19 | | |
| B124_2 | 30.20 | Satt527 | 70.36 | | |
| A459_1 | 30.37 | Satt561 | 71.44 | | |
| Satt398 | 30.58 | L050_8 | 72.73 | | |
| Satt694 | 30.79 | A132_2 | 73.41 | | |
| Sat_195 | 30.83 | Sat_099 | 78.23 | | |
| Sat_388 | 30.86 | G173_1 | 86.57 | | |
| Satt652 | 30.87 | Sat_286 | 87.41 | | |
| Satt771 | 30.87 | A461_1 | 87.87 | | |
| Sat_187 | 30.88 | Dt1 | 89.12 | | |
| Satt418 | 30.93 | DUBC015 | 90.33 | | |
| Satt278 | 31.21 | Satt006 | 92.00 | | |
| Sat_397 | 31.25 | Satt664 | 92.66 | | |
| Sat_191 | 32.00 | Satt229 | 93.88 | | |
| Sat_320 | 32.36 | A489_1 | 95.37 | | |
| A204_2 | 33.36 | Bng095_1 | 100.40 | | |
| Satt497 | 33.70 | L103_2 | 100.70 | | |
| G214_17 | 34.13 | K385_1 | 101.26 | | |
| Satt313 | 34.54 | R201_1 | 102.01 | | |

Figure 6 (continued)

| Chromosome M | |
|---|---|
| Marker | Position (cM) |
| Sat_389 | 0.00 |
| Satt404 | 0.84 |
| Sat_391 | 1.02 |
| GMSC514_SSR | 3.05 |
| Satt636 | 5.00 |
| Satt590 | 7.84 |
| Satt201 | 13.56 |
| Satt150 | 18.58 |
| Sat_316 | 21.00 |
| A351_1 | 22.38 |
| Mng339_1 | 27.33 |
| Ts | 30.25 |
| Satt567 | 33.47 |
| Satt540 | 35.84 |
| Bng222_1 | 38.50 |
| RGA_2b | 38.67 |
| Satt435 | 38.93 |
| R079_1 | 38.98 |
| A060_2 | 40.34 |
| DOP_H14 | 41.84 |
| A131_1 | 47.11 |
| Sat_244 | 48.86 |
| Satt463 | 50.09 |
| Sat_253 | 51.59 |
| Satt245 | 53.54 |
| A946_2 | 55.49 |
| Satt220 | 56.29 |
| A584_3 | 58.50 |
| Satt626 | 58.59 |
| OP_N04 | 59.11 |
| Satt323 | 60.04 |
| Sat_258 | 60.47 |
| Satt702 | 61.04 |
| L204_4 | 61.25 |
| Satt536 | 62.13 |
| Sat_003 | 62.31 |
| Sat_148 | 63.93 |
| Bng179_2 | 65.20 |
| K417_3 | 65.69 |
| Sat_226 | 65.79 |
| Satt175 | 66.98 |
| K024_1 | 71.05 |
| A226_1 | 71.08 |
| Satt494 | 71.70 |
| A715_1 | 73.37 |

| Chromosome M | |
|---|---|
| Marker | Position (cM) |
| Sct_147 | 73.87 |
| Sat_256 | 74.52 |
| Satt677 | 75.57 |
| Sat_288 | 76.41 |
| Satt655 | 76.41 |
| Satt680 | 77.19 |
| AF186183 | 77.23 |
| BE823543 | 78.37 |
| Satt306 | 80.01 |
| Satt728 | 80.90 |
| Sat_422 | 80.97 |
| E043_1 | 82.65 |
| Satt697 | 85.34 |
| Mng186_1 | 85.43 |
| K070_1 | 90.91 |
| BLT025_2 | 93.94 |
| Satt551 | 95.44 |
| M121_1 | 96.22 |
| Sat_121 | 103.98 |
| Satt250 | 107.69 |
| Satt618 | 111.05 |
| Satt210 | 112.08 |
| Satt346 | 112.79 |
| K227_1 | 120.37 |
| Sat_147 | 122.37 |
| A064_1 | 124.20 |
| Sat_276 | 128.47 |
| Satt308 | 130.75 |
| Satt336 | 133.83 |
| Mng381_1 | 139.46 |
| Sat_359 | 139.80 |
| Sat_330 | 140.69 |
| A504_1 | 142.17 |

Figure 6 (continued)

| Chromosome N | |
|---|---|
| Marker | Position (cM) |
| L2 | 0.00 |
| Sct_195 | 2.44 |
| Sat_379 | 4.33 |
| A071_10 | 9.66 |
| A071_3 | 10.16 |
| A071_4 | 10.26 |
| A071_6 | 10.40 |
| AC_telo | 10.88 |
| Rps7 | 16.01 |
| R022_1 | 16.66 |
| L050_12 | 20.71 |
| Satt152 | 22.67 |
| OP_N03 | 24.79 |
| BLT004_1 | 25.49 |
| Satt631 | 26.13 |
| Satt159 | 27.12 |
| Satt009 | 28.52 |
| Satt641 | 29.28 |
| RGA_6a | 29.46 |
| Sat_186 | 30.11 |
| A071_2 | 30.35 |
| K418_1 | 30.35 |
| K395_2 | 31.67 |
| OPAC12b | 31.85 |
| Satt530 | 32.84 |
| Satt683 | 34.52 |
| Satt675 | 34.65 |
| A280_1 | 34.91 |
| Satt624 | 35.32 |
| A426_2 | 35.56 |
| Sle_003 | 35.82 |
| i4_2 | 35.97 |
| Sat_084 | 36.86 |
| Satt393 | 37.43 |
| Satt584 | 37.98 |
| Satt485 | 38.07 |
| Sat_186 | 38.59 |
| Sat_208 | 39.34 |
| BLT049_1 | 39.88 |
| Bng095_2 | 40.13 |
| OP_F13 | 40.16 |
| Satt125 | 40.63 |
| Sat_275 | 40.81 |
| Sle2_3 | 41.36 |
| RGA_6b | 42.10 |

| Chromosome N | |
|---|---|
| Marker | Position (cM) |
| OP_U09b | 42.84 |
| mO128_1 | 43.04 |
| Sat_280 | 43.45 |
| Satt080 | 45.13 |
| Sat_266 | 47.27 |
| L103_1 | 49.73 |
| B162_1 | 49.77 |
| peG488_2 | 51.56 |
| Satt387 | 53.25 |
| Rpg4 | 55.38 |
| Sat_236 | 57.59 |
| Sat_033 | 58.38 |
| Satt521 | 65.45 |
| A808_1 | 68.76 |
| Satt549 | 70.59 |
| S11 | 71.90 |
| Satt660 | 72.59 |
| GMABAB_SSR | 73.10 |
| BLT015_1 | 74.48 |
| Satt237 | 74.98 |
| Satt339 | 75.91 |
| Satt255 | 76.48 |
| Sat_304 | 77.09 |
| Sat_091 | 79.51 |
| Satt312 | 79.86 |
| Sat_285 | 81.91 |
| G214_18 | 82.70 |
| Satt234 | 84.59 |
| Sat_239 | 87.34 |
| Sat_241 | 89.37 |
| Satt257 | 92.55 |
| Sat_306 | 93.11 |
| Sat_295 | 95.00 |
| Satt022 | 102.05 |
| Sat_125 | 103.33 |
| S02115-1-A | 105.63 |
| A455_2 | 113.48 |
| A363_3 | 116.66 |

Figure 6 (continued)

| Chromosome O | |
|---|---|
| Marker | Position (cM) |
| Sat_196 | 0.00 |
| Satt358 | 5.44 |
| Sat_132 | 8.75 |
| Satt487 | 9.53 |
| Satt500 | 14.17 |
| Satt492 | 17.25 |
| Sat_321 | 19.44 |
| Satt445 | 20.43 |
| Sat_303 | 20.93 |
| A081_1 | 21.33 |
| Sat_318 | 24.61 |
| Storage_1 | 28.29 |
| G248_1 | 28.37 |
| BF008905 | 28.95 |
| K265_2 | 30.51 |
| G214_19 | 36.13 |
| A882_1 | 37.75 |
| Satt653 | 38.09 |
| Sat_145 | 39.25 |
| Satt259 | 39.82 |
| Satt347 | 42.29 |
| L185_2 | 43.91 |
| Bng015_1 | 45.50 |
| Satt420 | 49.70 |
| L34842 | 50.36 |
| Sat_221 | 51.00 |
| Sat_291 | 51.90 |
| Satt473 | 52.11 |
| Satt679 | 53.18 |
| K011_7 | 53.49 |
| Satt466 | 53.66 |
| Satt479 | 54.20 |
| Satt585 | 54.68 |
| G214_20 | 54.99 |
| Satt550 | 55.09 |
| Satt188 | 55.58 |
| Satt576 | 55.81 |
| Satt128 | 56.13 |
| Satt608 | 56.27 |
| Satt094 | 56.58 |
| BLT049_6 | 56.68 |
| Satt633 | 56.93 |
| Satt262 | 57.02 |
| OP_L06 | 57.73 |
| Satt173 | 58.40 |

| Chromosome O | |
|---|---|
| Marker | Position (cM) |
| Satt345 | 59.43 |
| Satt241 | 59.49 |
| Bng123_1 | 60.38 |
| Sat_193 | 61.11 |
| Bng062_1 | 61.52 |
| Mng273_1 | 62.88 |
| T003_1 | 63.61 |
| Sat_282 | 63.81 |
| Satt219 | 64.00 |
| DUBC402 | 65.83 |
| Sat_341 | 67.93 |
| Satt563 | 68.38 |
| BE801128 | 68.97 |
| Mng208_1 | 70.25 |
| Satt478 | 71.09 |
| Sat_242 | 74.05 |
| A878_1 | 78.33 |
| Satt477 | 82.08 |
| Satt123 | 86.86 |
| mQ117_1 | 87.76 |
| Bng070_1 | 89.98 |
| Satt331 | 93.37 |
| SOYLBC | 95.00 |
| L204_5 | 95.54 |
| B157_1 | 96.01 |
| Satt592 | 100.37 |
| Legh | 101.02 |
| 138GA26 | 105.40 |
| Satt581 | 106.02 |
| Sat_274 | 107.58 |
| Sat_038 | 112.16 |
| A102_2 | 114.44 |
| Mng211_1 | 116.37 |
| Satt153 | 118.13 |
| Satt243 | 119.50 |
| Pgm1 | 122.22 |
| Sat_307 | 123.43 |
| BLT027_1 | 123.90 |
| T027_1 | 124.16 |
| Mng085_1 | 126.37 |
| T010_1 | 126.98 |
| Sat_109 | 127.50 |
| BLT027_4 | 127.90 |
| Sat_231 | 128.44 |
| Sat_108 | 129.30 |

| Chromosome O | |
|---|---|
| Marker | Position (cM) |
| Sat_190 | 129.80 |
| E2 | 136.33 |
| A664_1 | 137.66 |
| A955_2 | 138.38 |
| Scaa001 | 146.40 |

Figure 7

| Commercial Lines | CRDC Score | Used in Trait Allele | Used in InterGroup |
|---|---|---|---|
| 93M20 | 1 | YES | YES |
| 93M70 | 2 | YES | YES |
| 92M75 | 2 | YES | YES |
| 92M80 | 2 | YES | YES |
| 92M92 | 2 | YES | YES |
| 93B87 | 2 | YES | YES |
| 93B15 | 2 | YES | YES |
| 93B36 | 3 | YES | YES |
| 93B53 | 3 | YES | YES |
| 93B68 | 3 | YES | YES |
| 93M40 | 3 | YES | YES |
| 94B74 | 3 | YES | YES |
| 93M61 | 3 | YES | YES |
| 93B35 | 3 | YES | YES |
| 93B47 | 3 | YES | YES |
| 93M43 | 3 | YES | YES |
| 93M81 | 3 | YES | YES |
| 94B54 | 3 | YES | YES |
| 93M62 | 4 | YES | |
| 93B01 | 4 | YES | |
| 93B09 | 4 | YES | |
| 93B72 | 4 | YES | |
| 93B82 | 4 | YES | |
| 93M11 | 4 | YES | |
| 93M50 | 4 | YES | |
| 93M95 | 4 | YES | |
| 94M31 | 4 | YES | |
| 93M14 | 4 | YES | |
| 93B67 | 4 | YES | |
| 93M12 | 4 | YES | |
| 93M52 | 4 | YES | |
| 93M92 | 4 | YES | |
| 94B13 | 4 | YES | |
| 92B95 | 4 | YES | |
| 92M61 | 4 | YES | |
| 93B26 | 4 | YES | |
| 93B85 | 4 | YES | |
| 93M94 | 4 | YES | |
| 93M01 | 4 | YES | |
| 92B12 | 5 | YES | |
| 92B63 | 5 | YES | |
| 93M51 | 5 | YES | |
| 93M82 | 5 | YES | |

Figure 7 (continued)

| Commercial Lines | CRDC Score | Used in Trait Allele | Used in InterGroup |
|---|---|---|---|
| 94M30 | 5 | YES | |
| 93M60 | 5 | YES | |
| 93M80 | 5 | YES | |
| 94B73 | 5 | YES | |
| 94M71 | 5 | YES | |
| 93M10 | 5 | YES | |
| 93M42 | 5 | YES | |
| 93M93 | 5 | YES | |
| 93M96 | 5 | YES | |
| 94M50 | 5 | YES | |
| 92M70 | 5 | YES | |
| 92M71 | 6 | YES | |
| 92M91 | 6 | YES | |
| 93B86 | 6 | YES | |
| 93M90 | 6 | YES | |
| 92B62 | 6 | YES | |
| 92B74 | 6 | YES | |
| 92M40 | 6 | YES | |
| 94B53 | 6 | YES | |
| 94M40 | 6 | YES | |
| 93M30 | 7 | YES | YES |
| 92M50 | 7 | YES | YES |
| 94M70 | 7 | YES | YES |
| 94M80 | 7 | YES | YES |
| 94M90 | 7 | YES | YES |
| 92B38 | 7 | YES | YES |
| 92B84 | 7 | YES | YES |
| 93M41 | 7 | YES | YES |
| 92B13 | 7 | YES | YES |
| 92B47 | 8 | YES | YES |
| 92M31 | 8 | YES | YES |
| 92B14 | 8 | YES | YES |
| 92M30 | 8 | YES | YES |
| 92B24 | 8 | YES | YES |
| 92B75 | 8 | YES | YES |
| 92B05 | 8 | YES | YES |

SEQUENCE LISTING

<160> NUMBER OF SEQ ID NOS: 30

<210> SEQ ID NO 1
<211> LENGTH: 15
<212> TYPE: DNA
<213> ORGANISM: Glycine Max
<220> FEATURE:
<221> NAME/KEY: source
<222> LOCATION: (0)...(0)
<223> OTHER INFORMATION: Left primer sequence for marker Sct_028 in
      Glycine max

<400> SEQUENCE: 1
tcgccggtac aaaag                                                      15

<210> SEQ ID NO 2
<211> LENGTH: 18
<212> TYPE: DNA
<213> ORGANISM: Glycine max
<220> FEATURE:
<221> NAME/KEY: source
<222> LOCATION: (0)...(0)
<223> OTHER INFORMATION: Right  primer sequence for marker Sct_028 in
      Glycine max

<400> SEQUENCE: 2
cgaatgaaca aacaaaca                                                   18

<210> SEQ ID NO 3
<211> LENGTH: 25
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for marker Satt512 in
      Glycine max

<400> SEQUENCE: 3
aacgtcttca agtcaagtgc ctaca                                           25

<210> SEQ ID NO 4
<211> LENGTH: 26
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for marker Satt512 in
      Glycine max

<400> SEQUENCE: 4
gcccacatag ttttcattt tctcca                                           26

<210> SEQ ID NO 5
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for marker S60211-TB in
      Glycine max

<400> SEQUENCE: 5
gaagatccta acacgatggc cg                                              22

<210> SEQ ID NO 6

```
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for marker S60211-TB in
      Glycine max

<400> SEQUENCE: 6
ttcgttgttt ccttcattgc cg                                                  22

<210> SEQ ID NO 7
<211> LENGTH: 18
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for Rmp1 marker Sat_117 in
      Glycine max

<400> SEQUENCE: 7
tttggcagtt tcttgtag                                                       18

<210> SEQ ID NO 8
<211> LENGTH: 15
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for Rmp1 marker Sat_117
      in Glycine max

<400> SEQUENCE: 8
gctggatcgc agtta                                                          15

<210> SEQ ID NO 9
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for marker S63880-CB in
      Glycine max

<400> SEQUENCE: 9
agtcctcctc gccaacaaca ac                                                  22

<210> SEQ ID NO 10
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for marker S63880-CB in
      Glycine max

<400> SEQUENCE: 10
ttcatttcat ttccaagcgg gt                                                  22

<210> SEQ ID NO 11
<211> LENGTH: 27
<212> TYPE: DNA
<213> ORGANISM: Glycine max
<220> FEATURE:
```

```
<221> NAME/KEY: source
<222> LOCATION: (0)...(0)
<223> OTHER INFORMATION: Left primer sequence for marker P13158A in
      Glycine max

<400> SEQUENCE: 11
actggaagag ggtgcttagg gaatctg                                              27

<210> SEQ ID NO 12
<211> LENGTH: 30
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for marker P13158A in
      Glycine max

<400> SEQUENCE: 12
gagaatctag tctaccacca taccacgaac                                           30

<210> SEQ ID NO 13
<211> LENGTH: 11
<212> TYPE: DNA
<213> ORGANISM: Artificial Sequence
<220> FEATURE:
<223> OTHER INFORMATION: Probe 1 sequence for marker P13158A in Glycine
      max

<400> SEQUENCE: 13
acactgctta c                                                               11

<210> SEQ ID NO 14
<211> LENGTH: 12
<212> TYPE: DNA
<213> ORGANISM: Artificial Sequence
<220> FEATURE:
<223> OTHER INFORMATION: Probe 2 sequence for marker P13158A in Glycine
      max

<400> SEQUENCE: 14
tttttgctag ag                                                              12

<210> SEQ ID NO 15
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for Rmp2 marker S00415-1-A
      in Glycine max

<400> SEQUENCE: 15
acaaaagcgg tgctgtttgc tc                                                   22

<210> SEQ ID NO 16
<211> LENGTH: 23
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for Rmp2 marker
      S00415-1-A in Glycine max

<400> SEQUENCE: 16
tatgaccatg gagtgcaagg tgg                                                  23
```

-continued

<210> SEQ ID NO 17
<211> LENGTH: 14
<212> TYPE: DNA
<213> ORGANISM: Artificial Sequence
<220> FEATURE:
<223> OTHER INFORMATION: Probe 1 sequence for Rmp2 marker S00415-1-A in
      Glycine max

<400> SEQUENCE: 17
caacctcctt cttc                                                       14

<210> SEQ ID NO 18
<211> LENGTH: 14
<212> TYPE: DNA
<213> ORGANISM: Artificial Sequence
<220> FEATURE:
<223> OTHER INFORMATION: Probe 2 sequence for Rmp2 marker S00415-1-A in
      Glycine max

<400> SEQUENCE: 18
caacctcgtt cttc                                                       14

<210> SEQ ID NO 19
<211> LENGTH: 23
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for marker S00705-1-A in
      Glycine max

<400> SEQUENCE: 19
tgtgagatga tgcctccagg ttt                                             23

<210> SEQ ID NO 20
<211> LENGTH: 22
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for marker S00705-1-A in
      Glycine max

<400> SEQUENCE: 20
aatgcgagcc aagcaaaatg at                                              22

<210> SEQ ID NO 21
<211> LENGTH: 16
<212> TYPE: DNA
<213> ORGANISM: Artificial Sequence
<220> FEATURE:
<223> OTHER INFORMATION: Probe 1 sequence for  marker S00705-1-A in
      Glycine max

<400> SEQUENCE: 21
tttgtcatcc aactca                                                     16

<210> SEQ ID NO 22
<211> LENGTH: 16
<212> TYPE: DNA
<213> ORGANISM: Artificial Sequence
<220> FEATURE:
<223> OTHER INFORMATION: Probe 2 sequence for  marker S00705-1-A in
      Glycine max

```
<400> SEQUENCE: 22
tttgtcctcc aactca                                                    16

<210> SEQ ID NO 23
<211> LENGTH: 36
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for marker S02118-1-A in
      Glycine max

<400> SEQUENCE: 23
ggtccatatt acttgaaata caaagtttac agtatg                              36

<210> SEQ ID NO 24
<211> LENGTH: 35
<212> TYPE: DNA
<213> ORGANISM: Glycine max
<220> FEATURE:
<221> NAME/KEY: source
<222> LOCATION: (0)...(0)
<223> OTHER INFORMATION: Right primer sequence for marker S02118-1-A in
      Glycine max

<400> SEQUENCE: 24
cccagaacag gtaatagtag gtatatgctt attaa                               35

<210> SEQ ID NO 25
<211> LENGTH: 15
<212> TYPE: DNA
<213> ORGANISM: Artificial Sequence
<220> FEATURE:
<223> OTHER INFORMATION: Probe 1 sequence for  marker S02118-1-A in
      Glycine max

<400> SEQUENCE: 25
tccaattgct tcttt                                                     15

<210> SEQ ID NO 26
<211> LENGTH: 15
<212> TYPE: DNA
<213> ORGANISM: Artificial Sequence
<220> FEATURE:
<223> OTHER INFORMATION: Probe 2 sequence for  marker S02118-1-A in
      Glycine max

<400> SEQUENCE: 26
tccaattgcg tcttt                                                     15

<210> SEQ ID NO 27
<211> LENGTH: 29
<212> TYPE: DNA
<213> ORGANISM: Glycine max
<220> FEATURE:
<221> NAME/KEY: source
<222> LOCATION: (0)...(0)
<223> OTHER INFORMATION: Left primer sequence for marker S01954-1-A in
      Glycine max

<400> SEQUENCE: 27
cgattatata ggcgcctagg taaactttg                                      29

<210> SEQ ID NO 28
<211> LENGTH: 28
<212> TYPE: DNA
```

```
<213> ORGANISM: Glycine max
<220> FEATURE:
<221> NAME/KEY: source
<222> LOCATION: (0)...(0)
<223> OTHER INFORMATION: Right primer sequence for marker S01954-1-A in
      Glycine max

<400> SEQUENCE: 28
gacgagagaa tccttgccaa atttatag                                          28

<210> SEQ ID NO 29
<211> LENGTH: 16
<212> TYPE: DNA
<213> ORGANISM: Artificial Sequence
<220> FEATURE:
<223> OTHER INFORMATION: Probe 1 for marker S01954-1-A in Glycine max

<400> SEQUENCE: 29
tacgataatg ccctcg                                                       16

<210> SEQ ID NO 30
<211> LENGTH: 16
<212> TYPE: DNA
<213> ORGANISM: Artificial Sequence
<220> FEATURE:
<223> OTHER INFORMATION: Probe 2 for marker S01954-1-A

<400> SEQUENCE: 30
ttacgataac gccctc                                                       16
```

LOCI ASSOCIATED CHARCOAL ROT DROUGHT COMPLEX TOLERANCE IN SOYBEAN

CROSS REFERENCE TO RELATED APPLICATIONS

This application is a divisional of U.S. application Ser. No. 12/342,218 filed Dec. 23, 2008, now U.S. Pat. No. 8,329,982 granted Dec. 11, 2012, and further claims the benefit of U.S. application Ser. No. 12/342,189 filed Dec. 23, 2008, now U.S. Pat. No. 8,212,108 granted Jul. 3, 2012, U.S. application Ser. No. 12/342,204 filed Dec. 23, 2008, now U.S. Pat. No. 8,450,558 granted May 28, 2013, U.S. Application Ser. No. 61/082,024 filed Jul. 18, 2008, and U.S. Application Ser. No. 61/009,643 filed Dec. 31, 2007, all of which are each herein incorporated by reference in their entirety.

FIELD OF THE INVENTION

The present invention relates to compositions and methods for identifying soybean plants that are tolerant, have improved tolerance, or are susceptible to Charcoal Rot Drought Complex, where the methods use molecular genetic markers to identify, select and/or construct disease and/or drought-tolerant plants. The invention also relates to soybean plants that display tolerance or improved tolerance to Charcoal Rot Drought Complex that are generated by the methods of the invention.

BACKGROUND OF THE INVENTION

Soybean, a legume, has become the world's primary source of seed oil and seed protein. In addition, its utilization is being expanded to the industrial, manufacturing and pharmaceutical sectors. Soybean productivity is a vital agricultural and economic consideration. Unfortunately, soybean is host to one of the widest ranges of infectious pathogens of all crops. More than a hundred different pathogens are known to affect soybean plants, some of which pose significant economic threats. Improving soybean disease tolerance to these many pathogens is crucial to preventing yield losses.

Charcoal Rot and Drought

Charcoal rot is caused by the fungus *Macrophomina phaseolina*. The fungus has a particularly wide geographic distribution and is found throughout the world. *M. phaseolina* is most severe between 35° North and 35° South latitude (Wyllie, (1976) '*Macrophomina phaseolina*—Charcoal Rot' P482-484 In L. D. Hill (ed.) World Soybean Research Proc of the World Soybean Res. Conf., Champaign, Ill. Interstate, Danville, Ill.). The fungus also has a wide host range and infects over 500 crop and weed species and is highly variable. Known major crop hosts include alfalfa, maize, cotton, grain sorghum, peanut and soybean.

Symptoms of charcoal rot on soybean can appear during any growth stage. Infected seeds germinate, but usually die within a few days. The fungus also invades seedlings and may or may not exhibit symptoms, but serves as latent sources of inoculum for later in the growing season. The most common charcoal rot symptoms appear later in the season. Initially, disease plants exhibit smaller leaflet size, reduced height, and wilting. Ultimately, *M. phaseolina* can reduce plant height, root volume, and root weight by more than 50%. These deleterious effects on roots are most evident during the pod formation and seed filling stages, when demand for water is high. Affected plants mature several weeks earlier than normal and seed weight, number, and quality are reduced (Smith and Wyllie (1999) '*Charcoal rot*' In G. L. Hartman (ed.) Compendium of soybean diseases. 4$^{th}$ ed. APS Press, St. Paul, Minn.).

High ambient temperatures and low water availability exacerbate charcoal rot symptoms in soybean. Thus, charcoal rot is primarily known as a dry weather or drought induced disease. Symptoms caused by *M. phaseolina* are often attributed drought stress.

In localized areas, yield losses can be as high as 90%. In the period from 1996-2005, charcoal rot was the third leading cause of soybean yield loss in the U.S. Average annual losses were 29 MM bushels resulting in approximately $188 MM annual income loss. Only soybean cyst nematode and phythophthora root rot caused greater economic loss during that period (Wrather and Koenning (2006) 'Soybean Disease Loss Estimates for the United States, 1996-2006'. University of Missouri—Columbia Agriculture Experiment Station. November 2006 http://aes.missouri.edu/delta/research/soyloss.stm Dec. 5, 2007).

Complete or vertical resistance to *M. phaseolina* has not been identified in soybean, which strongly suggests that a single gene conferring resistance does not exist. In most field and greenhouse evaluations, the great majority of soybean cultivars have been found to be either highly or moderately susceptible to *M. phaseolina*. Only a few cultivars have been identified as possessing partial or horizontal resistance (Smith and Carville (1997) 'Field screening of commercial and experimental soybean cultivars for their reaction to *Macrophomina phaseolina*' Plant Dis 81:804-809).

An alternative approach to identifying complete resistance is to identify plants that show phenotypic tolerance to a particular pathogen. Tolerance can be described as the relative ability of a plant to survive infection without showing severe symptoms such as death, stunting, loss of vigor or yield loss. Tolerance includes any mechanism other than whole-plant immunity or resistance that reduces the expression of symptoms indicative of infection. Infected plants that exhibit tolerance will yield nearly as well as uninfected plants. However, phenotypic selection requires pathogenic infection which has many advantages.

The development of molecular genetic markers has facilitated mapping and selection of agriculturally important traits in soybean. Markers tightly linked to disease tolerance genes are an asset in the rapid identification of tolerant soybean lines on the basis of genotype by the use of marker assisted selection (MAS). Introgressing disease tolerance genes into a desired cultivar would also be facilitated by using suitable DNA markers.

Molecular Markers and Marker Assisted Selection

A genetic map is a graphical representation of a genome (or a portion of a genome such as a single chromosome) where the distances between landmarks on the chromosome are measured by the recombination frequencies between the landmarks. A genetic landmark can be any of a variety of known polymorphic markers, for example but not limited to, molecular markers such as SSR markers, RFLP markers, or SNP markers. Furthermore, SSR markers can be derived from genomic or expressed nucleic acids (e.g., ESTs). The nature of these physical landmarks and the methods used to detect them vary, but all of these markers are physically distinguishable from each other (as well as from the plurality of alleles of any one particular marker) on the basis of polynucleotide length and/or sequence.

Although specific DNA sequences which encode proteins are generally well-conserved across a species, other regions of DNA (typically non-coding) tend to accumulate polymorphism, and therefore, can be variable between individuals of the same species. Such regions provide the basis for numerous molecular genetic markers. In general, any differentially inherited polymorphic trait (including nucleic acid polymorphism) that segregates among progeny is a potential marker. The genomic variability can be of any origin, for example, insertions, deletions, duplications, repetitive elements, point mutations, recombination events or the presence and sequence of transposable elements. A large number of soybean molecular markers are known in the art, and are published or available from various sources, such as the SOYBASE internet resource. Similarly, numerous methods for detecting molecular markers are also well-established.

The primary motivation for developing molecular marker technologies from the point of view of plant breeders has been the possibility to increase breeding efficiency through marker assisted selection (MAS). A molecular marker allele that demonstrates linkage disequilibrium with a desired phenotypic trait (e.g., a quantitative trait locus, or QTL, such as resistance to a particular disease) provides a useful tool for the selection of a desired trait in a plant population. The key components to the implementation of this approach are: (i) the creation of a dense genetic map of molecular markers, (ii) the detection of QTL based on statistical associations between marker and phenotypic variability, (iii) the definition of a set of desirable marker alleles based on the results of the QTL analysis, and (iv) the use and/or extrapolation of this information to the current set of breeding germplasm to enable marker-based selection decisions to be made.

The availability of integrated linkage maps of the soybean genome containing increasing densities of public soybean markers has facilitated soybean genetic mapping and MAS. See, e.g., Cregan, et al., (1999) "An Integrated Genetic Linkage Map of the Soybean Genome" *Crop Sci* 39:1464-1490; Song, et al., (2004) "A New Integrated Genetic Linkage Map of the Soybean" *Theor Appl Genet* 109:122-128; Diwan and Cregan (1997) "Automated sizing of fluorescent-labeled simple sequence repeat (SSR) markers to assay genetic variation in Soybean" *Theor Appl Genet* 95:220-225; the SOYBASE resources on the world wide web, including the Shoemaker Lab Home Page and other resources that can be accessed through SOYBASE; and see, the Soybean Genomics and Improvements Laboratory (SGIL) website on the world wide web, and see especially the Cregan Lab webpage.

Two types of markers are frequently used in marker assisted selection protocols, namely simple sequence repeat (SSR, also known as microsatellite) markers, and single nucleotide polymorphism (SNP) markers. The term SSR refers generally to any type of molecular heterogeneity that results in length variability, and most typically is a short (up to several hundred base pairs) segment of DNA that consists of multiple tandem repeats of a two or three base-pair sequence. These repeated sequences result in highly polymorphic DNA regions of variable length due to poor replication fidelity, e.g., caused by polymerase slippage. SSRs appear to be randomly dispersed through the genome and are generally flanked by conserved regions. SSR markers can also be derived from RNA sequences (in the form of a cDNA, a partial cDNA or an EST) as well as genomic material.

The characteristics of SSR heterogeneity make them well suited for use as molecular genetic markers; namely, SSR genomic variability is inherited, is multiallelic, codominant and is reproducibly detectable. The proliferation of increasingly sophisticated amplification-based detection techniques (e.g., PCR-based) provides a variety of sensitive methods for the detection of nucleotide sequence heterogeneity. Primers (or other types of probes) are designed to hybridize to conserved regions that flank the SSR domain, resulting in the amplification of the variable SSR region. The different sized amplicons generated from an SSR region have characteristic and reproducible sizes. The different sized SSR amplicons observed from two homologous chromosomes in an individual, or from different individuals in the plant population are generally termed "marker alleles." As long as there exists at least two SSR alleles that produce PCR products with at least two different sizes, the SSRs can be employed as a marker.

Soybean markers that rely on single nucleotide polymorphisms (SNPs) are also well known in the art. Various techniques have been developed for the detection of SNPs, including allele specific hybridization (ASH; see, e.g., Coryell, et al. (1999) "Allele specific hybridization markers for soybean," *Theor Appl Genet* 98:690-696). Additional types of molecular markers are also widely used, including but not limited to expressed sequence tags (ESTs) and SSR markers derived from EST sequences, restriction fragment length polymorphism (RFLP), amplified fragment length polymorphism (AFLP), randomly amplified polymorphic DNA (RAPD) and isozyme markers. A wide range of protocols are known to one of skill in the art for detecting this variability, and these protocols are frequently specific for the type of polymorphism they are designed to detect. For example, PCR amplification, single-strand conformation polymorphisms (SSCP) and self-sustained sequence replication (3SR; see, Chan and Fox, (1999) "NASBA and other transcription-based amplification methods for research and diagnostic microbiology," *Reviews in Medical Microbiology* 10:185-196).

Linkage of one molecular marker to another molecular marker is measured as a recombination frequency. In general, the closer two loci (e.g., two SSR markers) are on the genetic map, the closer they lie to each other on the physical map. A relative genetic distance (determined by crossing over frequencies, measured in centimorgans; cM) is generally proportional to the physical distance (measured in base pairs, e.g., kilobase pairs [kb] or megabase pairs [Mbp]) that two linked loci are separated from each other on a chromosome. A lack of precise proportionality between cM and physical distance can result from variation in recombination frequencies for different chromosomal regions, e.g., some chromosomal regions are recombinational "hot spots," while others regions do not show any recombination, or only demonstrate rare recombination events. In general, the closer one marker is to another marker, whether measured in terms of recombination or physical distance, the more strongly they are linked. In some aspects, the closer a molecular marker is to a gene that encodes a polypeptide that imparts a particular phenotype (disease tolerance), whether measured in terms of recombination or physical distance, the better that marker serves to tag the desired phenotypic trait.

Genetic mapping variability can also be observed between different populations of the same crop species, including soybean. In spite of this variability in the genetic map that may occur between populations, genetic map and marker information derived from one population generally remains useful across multiple populations in identification of plants with desired traits, counter-selection of plants with undesirable traits and in guiding MAS.

QTL Mapping

It is the goal of the plant breeder to select plants and enrich the plant population for individuals that have desired traits, for example, pathogen tolerance, leading ultimately to increased agricultural productivity. It has been recognized for quite some time that specific chromosomal loci (or intervals) can be mapped in an organism's genome that correlate with particular quantitative phenotypes. Such loci are termed quantitative trait loci, or QTL. The plant breeder can advantageously use molecular markers to identify desired individuals by identifying marker alleles that show a statistically significant probability of co-segregation with a desired phenotype (e.g., pathogenic infection tolerance), manifested as linkage disequilibrium. By identifying a molecular marker or clusters of molecular markers that co-segregate with a quantitative trait, the breeder is thus identifying a QTL. By identifying and selecting a marker allele (or desired alleles from multiple markers) that associates with the desired phenotype, the plant breeder is able to rapidly select a desired phenotype by selecting for the proper molecular marker allele (a process called marker-assisted selection, or MAS). The more molecular markers that are placed on the genetic map, the more potentially useful that map becomes for conducting MAS.

Multiple experimental paradigms have been developed to identify and analyze QTL (see, e.g., Jansen, (1996) *Trends Plant Sci* 1:89). In this study we utilized "Intergroup Allele Frequency Distribution" analysis using GeneFlow™ version 7.0 software. An intergroup allele frequency distribution analysis provides a method for finding non-random distributions of alleles between two phenotypic groups.

During processing, a contingency table of allele frequencies is constructed and from this a G-statistic and probability are calculated (the G statistic is adjusted by using the William's correction factor). The probability value is adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the Charcoal Rot infection phenotype and the marker will co-segregate. A more complete discussion of the derivation of the probability values can be found in the GeneFlow™ version 7.0 software documentation. See, also, Sokal and Rolf, (1981), *Biometry: The Principles and Practices of Statistics in Biological Research,* 2nd ed., San Francisco, W.H. Freeman and Co.

The underlying logic is that markers with significantly different allele distributions between the tolerant and susceptible groups (i.e., non random distributions) might be associated with the trait and can be used to separate them for purposes of marker assisted selection of soybean lines with previously uncharacterized tolerance or susceptibility. The present analysis examined one marker locus at a time and determined if the allele distribution within the tolerant group is significantly different from the allele distribution within the susceptible group. A statistically different allele distribution is an indication that the marker is linked to a locus that is associated with reaction to the trait of interest. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In addition, in this study we utilized "Trait Allele Frequency Analysis" using GeneFlow™ version 7.0 software. For the Trait Allele Correlation report you must select accessions, markers and a single trait. For each allele at each selected marker, the report will show you the effect of having 0, 1 or 2 doses of that allele on the trait of interest. For each dosage comparison it calculates a t-statistic, probability and adjusted probability by comparing the means of two different dosage classes. The adjusted probability gives you a better idea of the experiment-wise significance given the number of alleles being tested, and is calculated as $P\_adj = (1-((1-Prob)^{**}n))$ where n is the number of tests being done in this analysis (see, Experimental Design: Procedures for the Behavioral Sciences). A more complete discussion of the derivation of the probability values can be found in the GeneFlow version 7.0 software documentation. See also, Sokal and Rolf, (1995) Biometry, 3rd ed., San Francisco, W.H. Freeman and Co.

There is a need in the art for improved soybean strains that are tolerant to Charcoal Rot and its causative agents, namely *Macrophomina phaseolina* infection and low-available water growth conditions. There is a need in the art for methods that identify soybean plants or populations (germplasm) that display tolerance to Charcoal Rot Drought Complex. What is needed in the art is to identify molecular genetic markers that are linked to Charcoal Rot Drought Complex tolerance loci in order to facilitate MAS. Such markers can be used to select individual plants and plant populations that show favorable marker alleles in soybean populations and then employed to select the tolerant phenotype, or alternatively, be used to counterselect plants or plant populations that show a Charcoal Rot Drought Complex susceptibility phenotype. The present invention provides these and other advantages.

SUMMARY OF THE INVENTION

Compositions and methods for identifying soybean plants or germplasm with tolerance to Charcoal Rot Drought Complex are provided. Methods of making soybean plants or germplasm that are tolerant to Charcoal Rot Drought Complex, e.g., through introgression of desired tolerance marker alleles and/or by transgenic production methods, as well as plants and germplasm made by these methods, are also provided. Systems and kits for selecting tolerant plants and germplasm are also a feature of the invention.

Charcoal Rot is a major disease of soybean, causing severe losses in soybean viability and overall yield. Charcoal Rot is caused by infection of the plant with the pathogenic fungus *Macrophomina phaseolina*. While Charcoal Rot is more prevalent during periods of low-available water growth conditions, making such conditions another causative factor of Charcoal Rot, Charcoal Rot can exist in the absence of such growth conditions. *Macrophomina* resistant soybean cultivars have been produced in an attempt to reduce losses due to Charcoal Rot. However, the strong selective pressures that resistant soybean impose on *Macrophomina* are likely to cause relatively rapid loss of the resistance phenotype, as has been seen with other fungal pathogens of soybean, such as *Sclerotinia*. In contrast, tolerance to Charcoal Rot or its causative agents, *Macrophomina* infection and/or low-available water growth conditions, in which the plant survives and produces high yields, despite a productive *Macrophomina* infection, is an alternate strategy to combat losses due to Charcoal Rot. Such tolerance provides advantages over pathogen resistance. Selection for tolerance in the plant is less likely to result in the evolution of destructive races of *Macrophomina* that combat and overcome the tolerance traits, leading to a host/pathogen relationship that more resembles commensalism as opposed to parasitism.

Further, low-available water growth conditions, e.g. drought, is and has always been a major cause of soybean damage, causing severe losses in soybean viability and overall yield. Because of this, soybean plants tolerant to low-available water growth conditions are desirable outside of the realm of Charcoal Rot tolerance; tolerance to low-available water growth conditions would have economic benefits even in the absence of Charcoal Rot. Therefore, tolerance to low-available water growth conditions is a desirable trait in soybeans both alone and for its effects on Charcoal Rot tolerance.

The identification and selection of soybean plants that show tolerance to Charcoal Rot Drought Complex using MAS can provide an effective and environmentally friendly approach to overcoming losses caused by these conditions. The present invention provides a number of soybean marker loci and QTL chromosome intervals that demonstrate statistically significant co-segregation with Charcoal Rot Drought Complex tolerance. Detection of these QTL markers or additional loci linked to the QTL markers can be used in marker-assisted soybean breeding programs to produce tolerant plants or plants with improved tolerance.

In some aspects, the invention provides methods for identifying a first soybean plant or germplasm (e.g., a line or variety) that has tolerance, improved tolerance, or susceptibility to Charcoal Rot Drought Complex. In the methods, at least one allele of one or more marker locus (e.g., a plurality of marker loci) that is associated with the tolerance, improved tolerance, or susceptibility is detected in the first soybean plant or germplasm. The marker loci can be selected from the loci provided in FIG. 1, including Sct_028, Satt512, S60211-TB, Sat_117, S01954-1-A, P13158A, S63880-CB, S00415-1-A, S00705-1-A, and S02118-1-A, as well as any other marker that is linked to these QTL markers (e.g., within about 50 cM of these loci). The invention also provides chromosomal QTL intervals that correlate with Charcoal Rot Drought Complex tolerance. These intervals are located on linkage groups C2, E, B2, G, H, B1, C1, D1b and N. Any marker located within these intervals also finds use as a marker for Charcoal Rot Drought Complex tolerance and is also a feature of the invention. These intervals include:
  (i) Satt286 and Satt371 (LG-C2);
  (ii) Satt575 and Sat_136 (LG-E);
  (iii) Satt467 and Satt416 (LG-B2);
  (iv) Satt612 and A681_1 (LG-G);
  (v) Sat_158 and A162_1 (LG-H);
  (vi) Satt444 and Sat_331 (LG-B1);
  (vii) Bng019_1 and Sct_191 (LG-C1);
  (viii) A605_1 and A519_2 (LG-D1b); or,
  (ix) Sat_306 and A363_3 (LG-N).

A plurality of marker loci can be selected in the same plant. Which QTL markers are selected in combination is not particularly limited. The QTL markers used in combinations can be any of the markers listed in FIG. 1, any other marker that is linked to the markers in FIG. 1 (e.g., the linked markers as determined from FIG. 6 or determined from the SOYBASE resource), or any marker within the QTL intervals described herein.

One aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Satt286 and Satt371. In one aspect, the first marker locus localizes within a chromosomal interval flanked by and including Satt205 and Satt433. In another aspect, the first marker locus localizes within a chromosomal interval flanked by and including Sat_238 and Sat_252. In another aspect, the first marker locus localizes within a chromosomal interval flanked by and including Satt307 and A538_1. In yet another aspect, the first marker locus localizes within a chromosomal interval flanked by and including Satt307 and Satt202. In other aspects, the first marker locus localizes within a chromosomal interval flanked by and including, and linked to the Sct_028 marker, e.g., Satt286 and Satt202, Satt286 and Sat_252, Satt286 and Satt316, Satt286 and Satt433, Satt286 and Satt371, Sat_402 and Satt202, Sat_402 and Sat_252, Sat_402 and Satt316, Sat_402 and Satt433, Sat_402 and Satt371, Satt277 and Satt202, Satt277 and Sat_252, Satt277 and Satt316, Satt277 and Satt433, Satt277 and Satt371, Satt365 and Satt202, Satt365 and Sat_252, Satt365 and Satt316, Satt365 and Satt433, Satt365 and Satt371, Satt205 and Satt202, Satt205 and Sat_252, Satt205 and Satt316, Satt205 and Satt433, Satt205 and Satt371, Satt557 and Satt202, Satt557 and Sat_252, Satt557 and Satt316, Satt557 and Satt433, Satt557 and Satt371, Satt289 and Satt202, Satt289 and Sat_252, Satt289 and Satt316, Satt289 and Satt433, Satt289 and Satt371, Satt134 and Satt202, Satt134 and Sat_252, Satt134 and Satt316, Satt134 and Satt433, Satt134 and Satt371, Sat_312 and Satt202, Sat_312 and Sat_252, Sat_312 and Satt316, Sat_312 and Satt433, Sat_312 and Satt371, Satt489 and Satt202, Satt489 and Sat_252, Satt489 and Satt316, Satt489 and Satt433, Satt489 and Satt371, Satt319 and Satt202, Satt319 and Sat_252, Satt319 and Satt316, Satt319 and Satt433, Satt319 and Satt371, Satt658 and Satt202, Satt658 and Sat_252, Satt658 and Satt316, Satt658 and Satt433, Satt658 and Satt371, AG36 and Satt202, AG36 and Sat_252, AG36 and Satt316, AG36 and Satt433, AG36 and Satt371, Satt100 and Satt202, Satt100 and Sat_252, Satt100 and Satt316, Satt100 and Satt433, Satt100 and Satt371, Sat_251 and Satt202, Sat_251 and Sat_252, Sat_251 and Satt316, Sat_251 and Satt433, Sat_251 and Satt371, Sat_142 and Satt202, Sat_142 and Sat_252, Sat_142 and Satt316, Sat_142 and Satt433, Sat_142 and Satt371, Satt708 and Satt202, Satt708 and Sat_252, Satt708 and Satt316, Satt708 and Satt433, Satt708 and Satt371, Sat_238 and Satt202, Sat_238 and Sat_252, Sat_238 and Satt316, Sat_238 and Satt433, Sat_238 and Satt371, Satt460 and Satt202, Satt460 and Sat_252, Satt460 and Satt316, Satt460 and Satt433, Satt460 and Satt371, Satt079 and Satt202, Satt079 and Sat_252, Satt079 and Satt316, Satt079 and Satt433, Satt079 and Satt371, Sat_263 and Satt202, Sat_263 and Sat_252, Sat_263 and Satt316, Sat_263 and Satt433, Sat_263 and Satt371, Staga001 and Satt202, Staga001 and Sat_252, Staga001 and Satt316, Staga001 and Satt433, Staga001 and Satt371, Satt307 and Satt202, Satt307 and Sat_252, Satt307 and Satt316, Satt307 and Satt433, and Satt307 and Satt371. In some aspects, the first marker locus localizes within a chromosomal interval flanked by and including, and closely linked to the Sct_028 marker, e.g., Satt205 and Satt202, Satt205 and Sat_252, Satt205 and Satt316, Satt205 and Satt433, Satt557 and Satt202, Satt557 and Sat_252, Satt557 and Satt316, Satt557 and Satt433, Satt289 and Satt202, Satt289 and Sat_252, Satt289 and Satt316, Satt289 and Satt433, Satt134 and Satt202, Satt134 and Sat_252, Satt134 and Satt316, Satt134 and Satt433, Sat_312 and Satt202, Sat_312 and Sat_252, Sat_312 and Satt316, Sat_312 and Satt433, Satt489 and Satt202, Satt489 and Sat_252, Satt489 and Satt316, Satt489 and Satt433, Satt319 and Satt202, Satt319 and Sat_252, Satt319 and Satt316, Satt319 and Satt433, Satt658 and Satt202, Satt658 and Sat_252, Satt658 and Satt316, Satt658 and Satt433, AG36 and Satt202, AG36 and Sat_252, AG36 and Satt316, AG36 and Satt433, Satt100 and Satt202, Satt100 and Sat_252, Satt100 and Satt316, Satt100 and Satt433, Sat_251 and Satt202, Sat_251 and Sat_252, Sat_251 and Satt316, Sat_251 and Satt433, Sat_142 and Satt202, Sat_142 and Sat_252, Sat_142 and Satt316, Sat_142 and Satt433, Satt708 and Satt202, Satt708 and Sat_252, Satt708 and Satt316, Satt708 and Satt433, Sat_238 and Satt202, Sat_238 and Sat_252, Sat_238 and Satt316, Sat_238 and Satt433, Satt460 and Satt202, Satt460 and Sat_252, Satt460 and Satt316, Satt460 and Satt433, Satt079 and Satt202, Satt079 and Sat_252, Satt079 and Satt316, Satt079 and Satt433, Sat_263 and Satt202, Sat_263 and Sat_252, Sat_263 and Satt316, Sat_263 and Satt433, Staga001 and Satt202, Staga001 and Sat_252, Staga001 and Satt316, Staga001 and Satt433, Satt307 and Satt202, Satt307 and Sat_252, Satt307 and Satt316, and Satt307 and Satt433. In a preferred embodiment, the first marker locus is Sct_028. In another preferred embodiment, the at least one allele comprises Sct_028:allele-3.

Methods wherein the first marker locus localizes within a chromosomal interval flanked by and including Satt286 and Satt371 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3. In further aspects, these methods can further comprise detecting in the first soybean plant or germplasm at least one allele of each of at least four additional marker loci that are associated with the tolerance, improved tolerance or susceptibility, wherein the at least four additional marker loci localize within the chromosome intervals flanked by and including Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3. In still further aspects, these methods can further comprise detecting in the first soybean plant or germplasm at least one allele of each of at least five additional marker loci that are associated with the tolerance, improved tolerance or susceptibility, wherein the at least five additional marker loci localize within the chromosome intervals flanked by and including Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3. In still further aspects, these methods can further comprise detecting in the first soybean plant or germplasm at least one allele of each of at least six additional marker loci that are associated with the tolerance, improved tolerance or susceptibility, wherein the at least six additional marker loci localize within the chromosome intervals flanked by and including Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3. In still further aspects, these methods can further comprise detecting in the first soybean plant or germplasm at least one allele of each of at least seven additional marker loci that are associated with the tolerance, improved tolerance or susceptibility, wherein the at least seven additional marker loci localize within the chromosome intervals flanked by and including Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3. In still further aspects, these methods can further comprise detecting in the first soybean plant or germplasm at least one allele of each of at least eight additional marker loci that are associated with the tolerance, improved tolerance or susceptibility, wherein the at least eight additional marker loci localize within the chromosome intervals flanked by and including Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3.

In methods wherein the first marker locus localizes within a chromosomal interval flanked by and including Satt286 and Satt371, in some aspects, the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects. In one aspect, the introgressed soybean plant or germplasm comprises Sct_028: allele-3.

Another aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Satt575 and Sat_136. In one aspect, the first marker locus localizes within a chromosomal interval flanked by and including Satt411 and Satt720. In another aspect, the first marker locus localizes within a chromosomal interval flanked by and including Sat_124 and A963_1. In yet another aspect, the first marker locus localizes within a chromosomal interval flanked by and including Sat_124 and Satt384. In other aspects, the first marker locus localizes within a chromosomal interval flanked by and including, and linked to the Satt512 marker, e.g., Satt575 and Satt384, Satt575 and Satt691, Satt575 and Satt720, Satt575 and Satt651, Satt575 and Satt212, Satt575 and Satt598, Satt575 and Satt573, Satt575 and Sat_136, Satt213 and Satt384, Satt213 and Satt691, Satt213 and Satt720, Satt213 and Satt651, Satt213 and Satt212, Satt213 and Satt598, Satt213 and Satt573, Satt213 and Sat_136, Sat_112 and Satt384, Sat_112 and Satt691, Sat_112 and Satt720, Sat_112 and Satt651, Sat_112 and Satt212, Sat_112 and Satt598, Sat_112 and Satt573, Sat_112 and Sat_136, Satt411 and Satt384, Satt411 and Satt691, Satt411 and Satt720, Satt411 and Satt651, Satt411 and Satt212, Satt411 and Satt598, Satt411 and Satt573, Satt411 and Sat_136, Sat_124 and Satt384, Sat_124 and Satt691, Sat_124 and Satt720, Sat_124 and Satt651, Sat_124 and Satt212, Sat_124 and Satt598, Sat_124 and Satt573, Sat_124 and Sat_136, In some aspects, the first marker locus localizes within a chromosomal interval flanked by and including, and closely linked to the Satt512 marker, e.g., Satt411 and Satt384, Satt411 and Satt691, Satt411 and Satt720, Sat_124 and Satt384, Sat_124 and Satt691, and Sat_124 and Satt720. In a preferred embodiment, the first marker locus is Satt512. In another preferred embodiment, the at least one allele comprises Satt512:allele-2 or Satt512:allele-5.

Methods wherein the first marker localizes within a chromosomal interval flanked by and including Satt575 and Sat_136 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked by and including chromosomal intervals selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Sat467 and Satt416, Satt612 and A681_1, Sat_158 and A162_1, Satt444 and Sat_331, Bng019_1 and Sct_191, A605_1 and A519_2, and Sat_306 and A363_3.

In methods wherein the first marker locus localizes within a chromosomal interval flanked by and including Satt575 and Sat_136, in some aspects, the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects. In one aspect, the introgressed soybean plant or germplasm comprises Satt512:allele-2 or Satt512:allele-5.

A further aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Satt467 and Satt416. In one aspect, the first marker locus localizes within a chromosomal interval flanked by and including Satt126 and Sct_034. In another aspect, the first marker locus localizes with a chromosomal interval flanked by and including RGA_8 and A343_1. In yet another aspect, the first marker locus localizes within a chromosomal interval flanked by and including Sat_287 and OP_T02. In still another aspect, the first marker locus localizes within a chromosomal interval flanked by and including Sat_287 and Sct_034. In other aspects, the first marker locus localizes within a chromosomal interval flanked by and including, and linked to the S60211-TB marker, e.g., Satt467 and Sct_034, Satt467 and Satt083, Satt467 and Satt168, Satt467 and Satt416, Sat_342 and Sct_034, Sat_342 and Satt083, Sat_342 and Satt168, Sat_342 and Satt416, Satt126 and Sct_034, Satt126 and Satt083, Satt126 and Satt168, Satt126 and Satt416, Sat_287 and Sct_034, Sat_287 and Satt083, Sat_287 and Satt168, and Sat_287 and Satt416. In some aspects, the first marker locus localizes within a chromosomal interval flanked by and including, and closely linked to the S60211-TB marker, e.g., Satt126 and A343_1, Satt126 and OP_T02, Satt126 and B142_1, Sat_287 and A343_1, Sat_287 and OP_T02, and Sat_287 and B142_1. In a preferred embodiment, the first marker locus is S60211-TB. In another preferred embodiment, the at least one allele comprises S60211-TB:allele-1.

Methods wherein the first marker locus localizes within a chromosome interval flanked by and including Satt467 and Satt416 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals flanked by and including chromosomal intervals selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked by and including chromosomal intervals selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Satt575 and Sat_136, Satt612 and A681_1, Sat_158 and A162_1, Satt444 and Sat_331, Bng019_1 and Sct_191, A605_1 and A519_2, and Sat_306 and A363_3.

In methods wherein the first marker locus localizes within a chromosomal interval flanked by and including Satt467 and Satt416, in some aspects, the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects. In one aspect, the introgressed soybean plant or germplasm comprises S60211-TB: allele-1.

Another aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Satt612 and A681_1. In one aspect, the first marker locus localizes within a chromosomal interval flanked by and including Satt612 and Sat_064. In one aspect, the first marker locus localizes within a chromosomal interval flanked by and including Sct_199 and Sat_064. In another aspect, the first marker locus localizes with a chromosomal interval flanked by and including L154_1 and A690_2. In yet another aspect, the first marker locus localizes within a chromosomal interval flanked by and including Satt191 and Sct_187. In still another aspect, the first marker localizes within a chromosomal interval flanked by and including Satt472 and Sct_187. In other aspects, the first marker locus localizes within a chromosomal interval flanked by and including, and linked to the Sat_117 marker or the S01954-1-A marker, e.g., Satt612 and A690_2, Satt612 and Bng069_1, Satt612 and Sct_187, Satt612 and Sat_372, Satt612 and Sat_064, Satt612 and A681_1, AF162283 and A690_2, AF162283 and Bng069_1, AF162283 and Sct_187, AF162283 and Sat_372, AF162283 and Sat_064, AF162283 and A681_1, Sct_199 and A690_1, Sct_199 and Bng069_1, Sct_199 and Sct_187, Sct_199 and Sat_372, Sct_199 and Sat_064, Sct_199 and A681_1, Satt472 and A690_1, Satt472 and Bng069_1, Satt472 and Sct_187, Satt472 and Sat_372, Satt472 and Sat_064, Satt472 and A681_1, Satt191 and A690_1, Satt191 and Bng069_1, Satt191 and Sct_187, Satt191 and Sat_372, Satt191 and Sat_064, and Satt191 and A681_1. In some aspects, the first marker locus localizes with a chromosomal interval flanked by and including, and closely linked to the Sat_117 marker or the S01954-1-A marker, e.g., Sct_199 and A690_1, Sct_199 and Bng069_1, Sct_199 and Sct_187, Sct_199 and Sat_372, Sct_199 and Sat_064, Satt472 and A690_1, Satt472 and Bng069_1, Satt472 and Sct_187, Satt472 and Sat_372, Satt472 and Sat_064, Satt191 and A690_1, Satt191 and Bng069_1, Satt191 and Sct_187, Satt191 and Sat_372, and Satt191 and Sat_064. In a preferred embodiment, the first marker locus is Sat_117. In another preferred embodiment, the at least one allele comprises Sat_117:allele-2.

Methods wherein the first marker locus localizes within a chromosomal interval flanked by and including Satt288 and A681_1, or Satt612 and A681_1, can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals flanked by and including chromosomal intervals selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked by and including chromosomal intervals selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Satt575 and Sat_136, Satt467 and Satt416, Sat_158 and A162_1, Satt444 and Sat_331, Bng019_1 and Sct_191, A605_1 and A519_2, and Sat_307 and A363_3.

In methods wherein the first marker locus localizes within a chromosomal interval flanked by and including Satt612 and A681_1, in some aspects, the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects. In one aspect, the introgressed soybean plant or germplasm comprises Sat_117: allele-2.

A further aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Sat_158 and A162_1. In one aspect, the first marker locus localizes within a chromosomal interval flanked by and including Satt637 and Satt434. In another aspect, the first marker locus localizes with a chromosomal interval flanked by and including Satt181 and Sat_218. In yet another aspect, the first marker locus localizes with a chromosomal interval flanked by and including Satt181 and A810_1. In other aspects, the first marker locus localizes within a chromosomal interval flanked by and including, and linked to the P13158A marker, e.g., Sat_158 and Sat_218, Sat_158 and Sat_180, Sat_158 and Satt434, Sat_158 and A162_1, Satt302 and Sat_218, Satt302 and Sat_180, Satt302 and Satt434, Satt302 and A162_1, Sat_175 and Sat_218, Sat_175 and Sat_180, Sat_175 and Satt434, Sat_175 and A162_1, Sat_216 and Sat_218, Sat_216 and Sat_180, Sat_216 and Satt434, Sat_216 and A162_1, Satt637 and Sat_218, Satt637 and Sat_180, Satt637 and Satt434, Satt637 and A162_1, Satt142 and Sat_218, Satt142 and Sat_180, Satt142 and Satt434, Satt142 and A162_1, Satt293 and Sat_218, Satt293 and Sat_180, Satt293 and Satt434, Satt293 and A162_1, Satt317 and Sat_218, Satt317 and Sat_180, Satt317 and Satt434, Satt317 and A162_1, Satt181 and Sat_218, Satt181 and Sat_180, Satt181 and Satt434, Satt181 and A162_1. In some aspects, the first marker locus localizes within a chromosomal interval flanked by and including, and closely linked to the P13158A marker, e.g., Sat_181 and A810_1, and Sat_181 and Sat_218. In a preferred embodiment, the first marker locus is P13158A. In another preferred embodiment, the at least one allele comprises P13158A:allele-2.

Methods wherein the first marker locus localizes within a chromosomal interval flanked by and including Sat_158 and A162_1 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Satt575 and Satt1362, Satt467 and Satt416, Satt612 and A681_1, Satt444 and Sat_331, Bng019_1 and Sct_191, A605_1 and A519_2, and Sat_306 and A363_3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Satt575 and Satt1362, Satt467 and Satt416, Satt612 and A681_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Satt575 and Satt1362, Satt467 and Satt416, Satt612 and A681_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Satt575 and Satt1362, Satt467 and Satt416, Satt612 and A681_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Satt575 and Satt1362, Satt467 and Satt416, Satt612 and A681_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals flanked by and including chromosomal intervals selected from the group consisting of Satt286 and Satt371, Satt575 and Satt1362, Satt467 and Satt416, Satt612 and A681_1, Satt444 and Sat_ 331, Bng019_1 and Sct_191, A605_1 and A519_2, and Sat_306 and A363_3. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked by and including chromosomal intervals selected from the group consisting of Satt286 and Satt371, Satt575 and Satt1362, Satt467 and Satt416, Satt612 and A681_1, Satt444 and Sat_331, Bng019_1 and Sct_191, A605_1 and A519_2, and Sat_306 and A363_3. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Satt575 and Satt1362, Satt467 and Satt416, Satt612 and A681_1, Satt444 and Sat_331, Bng019_1 and Sct_191, A605_1 and A519_2, and Sat_ 306 and A363_3.

In methods wherein the first marker locus localizes within a chromosomal interval flanked by and including Sat_158 and A162_1, in some aspects the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects. In one aspect, the introgressed soybean plant or germplasm comprises P13158A: allele-2.

A further aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Satt444 and Sat_331. In one aspect, the first marker locus localizes within a chromosomal interval flanked by and including Sat_123 and Satt484. In another aspect, the first marker locus localizes with a chromosomal interval flanked by and including Satt359 and Satt484. In yet another aspect, the first marker locus localizes with a chromosomal interval flanked by and including Satt359 and R244_1. In other aspects, the first marker locus localizes within a chromosomal interval flanked by and including, and linked to the S63880-CB marker, e.g., Satt444 and Satt484, Satt444 and Satt453, Satt444 and Sat_331, Satt665 and Satt484, Satt665 and Satt453, Satt665 and Sat_331, Sat_123 and Satt484, Sat_123 and Satt453, Sat_123 and Sat_331, Satt359 and Satt484, Satt359 and Satt453, and Satt359 and Sat_331. In some aspects, the first marker locus localizes within a chromosomal interval flanked by and including, and closely linked to the S63880-CB marker, e.g., Sat_123 and Satt484, and Satt359 and Satt484. In a preferred embodiment, the first marker locus is S63880-CB.

Methods wherein the first marker locus localizes within a chromosomal interval flanked by and including Satt444 and Sat_331 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Bng019__1 and Sct__191, A605__1 and A519__2, and Sat__306 and A363__3.

In methods wherein the first marker locus localizes within a chromosomal interval flanked by and including Satt444 and Sat__331, in some aspects the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects.

A further aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Bng019__1 and Sct__191. In one aspect, the first marker locus localizes within a chromosomal interval flanked by and including Satt578 and Satt294. In another aspect, the first marker locus localizes with a chromosomal interval flanked by and including Satt607 and G214__24. In yet another aspect, the first marker locus localizes with a chromosomal interval flanked by and including Dia and L192__1. In other aspects, the first marker locus localizes within a chromosomal interval flanked by and including, and linked to the S00415-1-A marker, e.g., Satt578 and Sat__311, Satt578 and Satt670, Satt578 and Sat__476, Satt578 and Sat399, Satt578 and Satt139, Satt578 and Satt718, Satt607 and Sat__311, Satt607 and Satt670, Satt607 and Sat__476, Satt607 and Sat399, Satt607 and Satt139, Satt607 and Satt718, Satt646 and Sat__311, Satt646 and Satt670, Satt646 and Sat__476, Satt646 and Sat399, Satt646 and Satt139, Satt646 and Satt718, Dia and Sat__311, Dia and Satt670, Dia and Sat__476, Dia and Sat399, Dia and Satt139, and Dia and Satt718. In some aspects, the first marker locus localizes within a chromosomal interval flanked by and including, and closely linked to the S00415-1-A marker, e.g., Satt607 and Sat399, Satt607 and Satt139, Satt607 and Satt718, Satt646 and Sat399, Satt646 and Satt139, Satt646 and Satt718, Dia and Sat399, Dia and Satt139, and Dia and Satt718. In a preferred embodiment, the first marker locus is S00415-1-A.

Methods wherein the first marker locus localizes within a chromosomal interval flanked by and including Bng019__1 and Sct__191 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Satt575 and Satt1362, Satt467 and Satt416, Satt612 and A681__1, Sat__158 and A162__1, Satt444 and Sat__331, A605__1 and A519__2, and Sat__306 and A363__3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, A605__1 and A519__2, and Sat__306 and A363__3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A1621, Satt444 and Sat__331, A605__1 and A519__2, and Sat__306 and A363__3. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A1621, Satt444 and Sat__331, A605__1 and A519__2, and Sat__306 and A363__3. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A1621, Satt444 and Sat__331, A605__1 and A519__2, and Sat__306 and A363__3. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A1621, Satt444 and Sat__331, A605__1 and A519__2, and Sat__306 and A363__3. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked and including chromosomal intervals selected from the group consisting of Satt286 and Satt371, Satt575 and Satt1362, Satt467 and Satt416, Satt612 and A681__1, Sat__158 and A1621, Satt444 and Sat__331, A6051 and A519__2, and Sat__306 and A363__3. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, A6051 and A519__2, and Sat__306 and A363__3.

In methods wherein the first marker locus localizes within a chromosomal interval flanked by and including Bng019__1 and Sct__191, in some aspects the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects.

A further aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including A605__1 and A519__2. In one aspect, the first marker locus localizes within a chromosomal interval flanked by and including Satt360 and Sat__139. In another aspect, the first marker locus localizes with a chromosomal interval flanked by and including Satt428 and B194__2. In yet another aspect, the first marker locus localizes with a chromosomal interval flanked by and including Satt644 and Satt041. In other aspects, the first marker locus localizes within a chromosomal interval flanked by and including, and linked to the S00705-1-A marker, e.g., Sat__423 and Sat__069, Sat__423 and Sat__139, Sat__423 and B194__2, Sat__423 and Satt041, Satt290 and Sat__069, Satt290 and Sat__139, Satt290 and B194__2, Satt290 and Satt041, Satt005 and Sat__069, Satt005 and Sat__139, Satt005 and B194__2, Satt005 and Satt041, Satt579 and Sat__069, Satt579 and Sat__139, Satt579 and B194__2, Satt579 and Satt041, Satt428 and Sat__069, Satt428 and Sat__139, Satt428 and B194__2, Satt428 and Satt041, Satt644 and Sat__069, Satt644 and Sat__139, Satt644 and B194__2, and Satt644 and Satt041. In some aspects, the first marker locus localizes within a chromosomal interval flanked by and including, and closely linked to the S00705-1-A marker, e.g., Satt428 and B194__2, Satt428 and Satt041, Satt644 and B194__2, and Satt644 and Satt041. In a preferred embodiment, the first marker locus is S00705-1-A.

Methods wherein the first marker locus localizes within a chromosomal interval flanked by and including A605__1 and A519__2 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and Sat__306 and A363__3.

In methods wherein the first marker locus localizes within a chromosomal interval flanked by and including A605__1 and A519__2, in some aspects the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects.

A further aspect relates to a method of identifying a first soybean plant or germplasm that displays tolerance, improved tolerance, or susceptibility to Charcoal Rot Drought Complex, the method comprising detecting in the first soybean plant or germplasm at least one allele of a first marker locus that is associated with the tolerance, improved tolerance or susceptibility, wherein the first marker locus localizes within a chromosome interval flanked by and including Sat__306 and A363__3. In one aspect, the first marker locus localizes within a chromosomal interval flanked by and including Sat__295 and A363__3. In another aspect, the first marker locus localizes with a chromosomal interval flanked by and including Satt022 and A363__3. In yet another aspect, the first marker locus localizes with a chromosomal interval flanked by and including Sat__125 and A455__2. In other aspects, the first marker locus localizes within a chromosomal interval flanked by and including, and linked to the S02118-1-A marker, e.g., Sat__306 and A455__2, Sat__295 and A455__2, Satt022 and A455__2, and Sat__125 and A363__3. In some aspects, the first marker locus localizes within a chromosomal interval flanked by and including, and closely linked to the S02118-1-A marker, e.g., Satt022 and A455__2, Satt022 and A363__3, Sat__125 and A455__2, and Sat__125 and A363__3. In a preferred embodiment, the first marker locus is S02118-1-A.

Methods wherein the first marker locus localizes within a chromosomal interval flanked by and including Sat__306 and A363__3 can further comprise detecting in the first soybean plant or germplasm at least one allele of at least one additional marker locus that is associated with the tolerance, improved tolerance or susceptibility, wherein the at least one additional marker locus localizes within a chromosome interval flanked by and including a chromosomal interval selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and A605__1 and A519__2. In some aspects, these methods can further comprise detecting in the first soybean plant or germplasm at least one allele of each of at least two additional marker loci that are associated with the tolerance, improved tolerance or susceptibility, wherein the at least two additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and A605__1 and A519__2. In additional aspects, these methods can further comprise detecting in the first soybean plant or germplasm at least one allele of each of at least three additional marker loci that are associated with the tolerance, improved tolerance or susceptibility, wherein the at least three additional marker loci localize within chromosome intervals flanked by and including chromosomal intervals selected from the group consisting of Satt286 and Satt371, Satt575 and Satt1362, Satt467 and Satt416, Satt612 and A681__1, Sat__158 and A162__1, Satt444 and Sat__331, Bng019__1 and Sct__191, and A605__1 and A519__2. In additional aspects, these methods can further comprise detecting in the first soybean plant or germplasm at least one allele of each of at least four additional marker loci that are associated with the tolerance, improved tolerance or susceptibility, wherein the at least four additional marker loci localize within chromosome intervals flanked by and including chromosomal intervals selected from the group consisting of Satt286 and Satt371, Satt575 and Satt1362, Satt467 and Satt416, Satt612 and A681_1, Sat_158 and A162_1, Satt444 and Sat_331, Bng019_1 and Sct_191, and A605_1 and A519_2. In additional aspects, these methods can further comprise detecting in the first soybean plant or germplasm at least one allele of each of at least five additional marker loci that are associated with the tolerance, improved tolerance or susceptibility, wherein the at least five additional marker loci localize within chromosome intervals flanked by and including chromosomal intervals selected from the group consisting of Satt286 and Satt371, Satt575 and Satt1362, Satt467 and Satt416, Satt612 and A681_1, Sat_158 and A162_1, Satt444 and Sat_331, Bng019_1 and Sct_191, and A605_1 and A519_2. In additional aspects, these methods can further comprise detecting in the first soybean plant or germplasm at least one allele of each of at least six additional marker loci that are associated with the tolerance, improved tolerance or susceptibility, wherein the at least six additional marker loci localize within chromosome intervals flanked by and including chromosomal intervals selected from the group consisting of Satt286 and Satt371, Satt575 and Satt1362, Satt467 and Satt416, Satt612 and A681_1, Sat_158 and A162_1, Satt444 and Sat_331, Bng019_1 and Sct_191, and A605_1 and A519_2. In additional aspects, these methods can further comprise detecting in the first soybean plant or germplasm at least one allele of each of at least seven additional marker loci that are associated with the tolerance, improved tolerance or susceptibility, wherein the at least seven additional marker loci localize within chromosome intervals flanked by and including chromosomal intervals selected from the group consisting of Satt286 and Satt371, Satt575 and Satt1362, Satt467 and Satt416, Satt612 and A681_1, Sat_158 and A162_1, Satt444 and Sat_331, Bng019_1 and Sct_191, and A605_1 and A519_2. In additional aspects, these methods can further comprise detecting in the first soybean plant or germplasm at least one allele of each of at least eight additional marker loci that are associated with the tolerance, improved tolerance or susceptibility, wherein the at least eight additional marker loci localize within chromosome intervals flanked by and including chromosomal intervals selected from the group consisting of Satt286 and Satt371, Satt575 and Satt1362, Satt467 and Satt416, Satt612 and A681_1, Sat_158 and A162_1, Satt444 and Sat_331, Bng019_1 and Sct_191, and A605_1 and A519_2.

In methods wherein the first marker locus localizes within a chromosomal interval flanked by and including Sat_306 and A363_3, in some aspects the at least one allele is correlated with tolerance or improved tolerance, and the method further comprises introgressing the allele in the first soybean plant or germplasm into a second soybean plant or germplasm to produce an introgressed soybean plant or germplasm. Introgressed soybean plants or germplasm produced by these methods are additional aspects.

An additional aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Satt286 and Satt371 on linkage group C2, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

Another aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Satt575 and Sat_136 on linkage group E, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

A further aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Satt467 and Satt416 on linkage group B2, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

Another aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Satt612 and A681_1 on linkage group G, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

Yet another aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Satt612 and Sat_064 on linkage group G, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

An additional aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Sat_158 and A162_1 on linkage group H, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

An additional aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Sat_158 and A162_1 on linkage group H, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

Yet another aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Satt444 and Sat_331 on linkage group B1, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

A further additional aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Bng019_1 and Sct_191 on linkage group C1, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

A further additional aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers A605_1 and A519_2 on linkage group D1b, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

A further additional aspect relates to a method of selecting at least one soybean plant by marker assisted selection of a quantitative trait locus associated with tolerance or improved tolerance to Charcoal Rot Drought Complex, wherein said quantitative trait locus is localized to a chromosomal interval defined by and including markers Sat_306 and A363_3 on linkage group N, said method comprising (a) testing at least one marker on said chromosomal interval for said quantitative trait locus; and (b) selecting said soybean plant comprising said quantitative trait locus. Other chromosomal intervals, such as those described above or elsewhere herein, are also useful in these methods.

Further aspects relate to methods of selecting at least one soybean plant by marker assisted selection of a quantitative trait locus associated with tolerance or improved tolerance to Charcoal Rot Drought Complex, wherein said quantitative trait locus is localized to at least one of (i) a chromosomal interval defined by and including markers Satt286 and Satt371 on linkage group C2, (ii) a chromosomal interval defined by and including markers Satt575 and Sat_136 on linkage group E, (iii) a chromosomal interval defined by and including markers Satt467 and Satt416 on linkage group B2, (iv) a chromosomal interval defined by and including markers Satt612 and A681_1 on linkage group G, (v) a chromosomal interval defined by and including markers Satt612 and Sat_064 on linkage group G, (vi) a chromosomal interval defined by and including markers Sat_158 and A162_1 on linkage group H, (vii) a chromosomal interval defined by and including markers Sat_158 and Satt434 on linkage group H, (viii) a chromosomal interval defined by and including markers Satt444 and Sat_331 on linkage group B1, (ix) a chromosomal interval defined by and including markers Bng019_1 and Sct_191 on linkage group C1, (x) a chromosomal interval defined by and including markers Satt578 and Sct_191 on linkage group C1, (xi) a chromosomal interval defined by and including markers A605_1 and A519_2 on linkage group D1b, (xii) a chromosomal interval defined by and including markers Sat_423 and Sat_069 on linkage group D1b, and (xiii) a chromosomal interval defined by and including markers Sat_306 and A363_3 on linkage group N, said method comprising: (a) testing at least one maker on each of said chromosomal intervals for said quantitative trait locus; and (b) selecting said soybean plant comprising said quantitative trait locus. Other chromosomal intervals, such as those described above or elsewhere herein, are also useful in these methods.

Additional aspects relate to methods of producing a soybean plant having tolerance or improved tolerance to Charcoal Rot Drought Complex, the method comprising introducing an exogenous nucleic acid into a target soybean plant or progeny thereof, wherein the exogenous nucleic acid is derived from a nucleotide sequence that is linked to at least one favorable allele of a marker locus that is associated with tolerance or improved tolerance to Charcoal Rot Drought Complex, wherein the marker locus localizes within a chromosomal interval selected from the group consisting of chromosomal intervals flanked by and including Satt286 and Satt371, Satt575 and Sat_136, Satt467 and Satt416, Satt612 and A681_1, Sat_158 and A162_1, Satt444 and Sat_331, Bng019_1 and Sct_191, A605_1 and A519_2, and Sat_306 and A363_3; whereby the resulting transgenic plant displays tolerance or improved tolerance to Charcoal Rot Drought Complex. Other chromosomal intervals, such as those described above or elsewhere herein, are also useful in these methods.

The markers that are linked to the QTL markers of FIG. 1 can be closely linked, for example, within about 10 cM from the FIG. 1 QTL markers. In some embodiments, the linked locus displays a genetic recombination distance of 9 cM, 8, 7, 6, 5, 4, 3, 2, 1, 0.75, 0.5 or 0.25, or less from the QTL marker. In some embodiments, the closely linked locus is selected from the list of marker loci provided in FIG. 6.

In some embodiments, preferred QTL markers are selected from Satt512 on linkage group E, SCT_028 on linkage group C2, S60211-TB on linkage group B2, Sat_117 on linkage group G, S01954-1-A on linkage group G, and S00415-1-A on linkage group C1. In other embodiments, preferred favorable alleles are selected from Satt512:allele-2, Satt512:allele-5, SCT_028:allele-3, S60211-TB:allele-1, and Sat_117:allele-2. In additional embodiments, preferred unfavorable alleles are/selected from Satt512:allele-1, SCT_028:allele-1, and S60211-TB:allele-2.

In some embodiments, the germplasm is a soybean line or variety. In some aspects, the tolerance or improved tolerance is a non-race specific tolerance or a non-race specific improved tolerance. In some aspects, the tolerance, improved tolerance, or susceptibility of a soybean plant to Charcoal Rot Drought Complex can be quantitated using any suitable means, for example soybean cultivars may be grown at a field location with a known history of Charcoal Rot and rated based on disease symptoms at the appropriate time.

Experienced plant breeders can recognize tolerant soybean plants in the field, and can select the tolerant individuals or populations for breeding purposes or for propagation. In this context, the plant breeder recognizes "tolerant" and "non-tolerant," or "susceptible" soybean plants.

Such plant breeding practitioners will appreciate that plant tolerance is a phenotypic spectrum consisting of extremes in tolerance, susceptibility and a continuum of intermediate tolerance phenotypes. Tolerance also varies due to environmental effects and the severity of pathogen infection. Evaluation of phenotypes using reproducible assays and tolerance scoring methods are of value to scientists who seek to identify genetic loci that impart tolerance, conduct marker assisted selection for tolerant population, and for introgression techniques to breed a tolerance trait into an elite soybean line, for example.

Various methods are known in the art for determining (and measuring) the tolerance of a soybean plant to Charcoal Rot Drought Complex. They describe a tolerance measurement scale of 1-9, with 9=no disease and 1=total necrosis caused by *Macrophomina phaseolina*. It will be appreciated that all such scales are relative and that numbering and precise correlation to any scale can be performed at the discretion of the practitioner.

Typically, individual field tests are monitored for Charcoal rot symptoms during the middle to late vegetative stages, but such symptoms typically appear in the early reproductive stage (during flowering and early pod set). Data collection is usually done in 3 or 4 successive scorings about 7 days apart. Scorings continue until worsening symptoms can no longer be quantified or until the symptoms are confounded by other factors such as other diseases, insect pressure, severe weather, or advancing maturity.

In general, while there is a certain amount of subjectivity to assigning severity measurements for disease caused symptoms, assignment to a given scale as noted above is well within the skill of a practitioner in the field. Measurements can also be averaged across multiple scorers to reduce variation in field measurements. Furthermore, although protocols using artificial inoculation of field nurseries with *Macrophomina phaseolina* can certainly be used in assessing tolerance, it is also typical for tolerance ratings to be based on actual field observations of fortuitous natural disease incidence, with the information corresponding to disease incidence for a cultivar being averaged over many locations and, typically, several years of crop growing.

If there is no disease present, the rating system above is inapplicable, because everything in an uninfected field scores as tolerant. However, if Charcoal Rot does occur in a specific field location, all of the lines at that location can be scored as noted above. These scores can accumulate over locations and years to show disease tolerance for given cultivars. Thus, older lines can have more years of observation than newer ones etc. However, relative measurements can easily be made using the scoring system noted above. Furthermore, the tolerance ratings can be updated and refined each year based on the previous year's observations in the field. Based on this, Charcoal Rot scores for a cultivar are relative measurements of tolerance.

The experiments described herein score soybean tolerance to Charcoal Rot Drought Complex using the following scale: 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death. FIG. 8 gives a representative example of cultivars with vastly different Charcoal Rot Drought Complex tolerance using this scoring system.

Any of a variety of techniques can be used to identify a marker allele. It is not intended that the method of allele detection be limited in any way. Methods for allele detection typically include molecular identification methods such as amplification and detection of the marker amplicon. For example, an allelic form of a polymorphic simple sequence repeat (SSR), or of a single nucleotide polymorphism (SNP) can be detected, e.g., by an amplification based technology. In these and other amplification based detection methods, the marker locus or a portion of the marker locus is amplified (e.g., via PCR, LCR or transcription using a nucleic acid isolated from a soybean plant of interest as a template) and the resulting amplified marker amplicon is detected. In one example of such an approach, an amplification primer or amplification primer pair is admixed with genomic nucleic acid isolated from the first soybean plant or germplasm, wherein the primer or primer pair is complementary or partially complementary to at least a portion of the marker locus, and is capable of initiating DNA polymerization by a DNA polymerase using the soybean genomic nucleic acid as a template. The primer or primer pair (e.g., a primer pair provided in FIG. 2) is extended in a DNA polymerization reaction having a DNA polymerase and a template genomic nucleic acid to generate at least one amplicon. In any case, data representing the detected allele(s) can be transmitted (e.g., electronically or via infrared, wireless or optical transmission) to a computer or computer readable medium for analysis or storage. In some embodiments, plant RNA is the template for the amplification reaction. In other embodiments, plant genomic DNA is the template for the amplification reaction. In some embodiments, the QTL marker is a SNP type marker, and the detected allele is a SNP allele (see, e.g., FIG. 3), and the method of detection is allele specific hybridization (ASH).

In some embodiments, the allele that is detected is a favorable allele that positively correlates with tolerance or improved tolerance. Alternatively, the allele that is detected can be an allele that correlates with disease susceptibility or reduced disease tolerance, and that allele is counter-selected. For example, alleles that can be selected for (favorable alleles) or against (unfavorable alleles) include:

Favorable Alleles:
Sct_028:allele-3, Satt512:allele-2, Satt512:allele-5, S60211-TB:allele-1, Sat_117:allele-2, P13158A:allele-2.

Unfavorable Alleles:
Sct_028:allele-1, Satt512:allele-1, S60211-TB:allele-2, S63880-CB:allele-3.

In the case where more than one marker is selected, an allele is selected for each of the markers; thus, two or more alleles are selected. In some embodiments, it can be the case that a marker locus will have more than one advantageous allele, and in that case, either allele can be selected.

It will be appreciated that the ability to identify QTL marker loci that correlate with tolerance, improved tolerance, or susceptibility of a soybean plant to Charcoal Rot Drought Complex provides a method for selecting plants that have favorable marker loci as well. That is, any plant that is identified as comprising a desired marker locus (e.g., a marker allele that positively correlates with tolerance) can be selected for, while plants that lack the locus, or that have a locus that negatively correlates with tolerance, can be selected against. Thus, in one method, subsequent to identification of a marker locus, the methods include selecting (e.g., isolating) the first soybean plant or germplasm, or selecting a progeny of the first plant or germplasm. In some embodiments, the resulting selected first soybean plant or germplasm can be crossed with a second soybean plant or germplasm (e.g., an elite or exotic soybean, depending on characteristics that are desired in the progeny).

Similarly, in other embodiments, if an allele is correlated with tolerance or improved tolerance to Charcoal Rot Drought Complex, the method can include introgressing the allele into a second soybean plant or germplasm to produce an introgressed soybean plant or germplasm. In some embodiments, the second soybean plant or germplasm will typically display reduced tolerance to Charcoal Rot Drought Complex as compared to the first soybean plant or germplasm, while the introgressed soybean plant or germplasm will display an increased tolerance to Charcoal Rot Drought Complex as compared to the second plant or germplasm. An introgressed soybean plant or germplasm produced by these methods is also a feature of the invention. In some embodiments, the favorable introgressed allele is selected from Sct_028:allele-3, Satt512:allele-2, S60211-TB:allele-1, Sat_117:allele-2, and P13158A:allele-2.

In other aspects, various software is used in determining linked marker loci. For example, TASSEL, MapManager-QTX, and GeneFlow all find use with the invention. In some embodiments, such as when software is used in the linkage analysis, the detected allele information (i.e., the data) is electronically transmitted or electronically stored, for example, in a computer readable medium.

In other aspects, various software is used in determining linked marker loci used to construct a transgenic plant. For example, TASSEL, MapManager-QTX, and GeneFlow all find use with the invention.

Systems for identifying a soybean plant predicted to have tolerance or improved tolerance to Charcoal Rot Drought Complex are also a feature of the invention. Typically, the systems include a set of marker primers and/or probes configured to detect at least one favorable allele of one or more marker locus associated with tolerance or improved tolerance to Charcoal Rot Drought Complex, wherein the marker locus or loci are selected from: Sct_028, Satt512, S60211-TB, Sat_117, S01954-1-A, P13158A, S63880-CB, S00415-1-A, S00705-1-A, and S02118-1-A as well as any other marker that is linked (or in some embodiments, closely linked, e.g., demonstrating not more than 10% recombination frequency) to these QTL markers; and furthermore, any marker locus that is located within the chromosomal QTL intervals including:
 (i) Satt286 and Satt371 (LG-C2);
 (ii) Satt575 and Sat_136 (LG-E);
 (iii) Satt467 and Satt416 (LG-B2);
 (iv) Satt612 and A681_1 (LG-G);
 (v) Sat_158 and A162_1 (LG-H);
 (vi) Satt444 and Sat_331 (LG-B1));
 (vii) Bng019_1 and Sct_191 (LG-C1);
 (viii) A605_1 and A519_2 (LG-D1b); and,
 (xi) Sat_306 and A363_3 (LG-N).

In some embodiments, preferred QTL markers used are selected from Satt512, SCT_028, S60211-TB, Sat_117, S01954-1-A, and, S00415-1-A.

Where a system that performs marker detection or correlation is desired, the system can also include a detector that is configured to detect one or more signal outputs from the set of marker probes or primers, or amplicon thereof, thereby identifying the presence or absence of the allele; and/or system instructions that correlate the presence or absence of the favorable allele with the predicted tolerance. The precise configuration of the detector will depend on the type of label used to detect the marker allele. Typical embodiments include light detectors, radioactivity detectors, and the like. Detection of the light emission or other probe label is indicative of the presence or absence of a marker allele. Similarly, the precise form of the instructions can vary depending on the components of the system, e.g., they can be present as system software in one or more integrated unit of the system, or can be present in one or more computers or computer readable media operably coupled to the detector. In one typical embodiment, the system instructions include at least one look-up table that includes a correlation between the presence or absence of the favorable allele and predicted tolerance, improved tolerance or susceptibility.

In some embodiments, the system can be comprised of separate elements or can be integrated into a single unit for convenient detection of markers alleles and for performing marker-tolerance trait correlations. In some embodiments, the system can also include a sample, for example, genomic DNA, amplified genomic DNA, cDNA, amplified cDNA, RNA, or amplified RNA from soybean or from a selected soybean plant tissue.

Kits are also a feature of the invention. For example, a kit can include appropriate primers or probes for detecting tolerance associated marker loci and instructions in using the primers or probes for detecting the marker loci and correlating the loci with predicted Charcoal Rot Drought Complex tolerance. The kits can further include packaging materials for packaging the probes, primers or instructions, controls such as control amplification reactions that include probes, primers or template nucleic acids for amplifications, molecular size markers, or the like.

DEFINITIONS

Before describing the present invention in detail, it is to be understood that this invention is not limited to particular embodiments, which can, of course, vary. It is also to be understood that the terminology used herein is for the purpose of describing particular embodiments only, and is not intended to be limiting. As used in this specification and the appended claims, terms in the singular and the singular forms "a", "an" and "the", for example, include plural referents unless the content clearly dictates otherwise. Thus, for example, reference to "plant", "the plant" or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Unless otherwise indicated, nucleic acids are written left to right in 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant. Thus, the term "soybean plant" includes whole soybean plants, soybean plant cells, soybean plant protoplast, soybean plant cell or soybean tissue culture from which soybean plants can be regenerated, soybean plant calli, soybean plant clumps and soybean plant cells that are intact in soybean plants or parts of soybean plants, such as soybean seeds, soybean pods, soybean flowers, soybean cotyledons, soybean leaves, soybean stems, soybean buds, soybean roots, soybean root tips and the like.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

The term "allele" refers to one of two or more different nucleotide sequences that occur at a specific locus. For example, a first allele can occur on one chromosome, while a second allele occurs on a second homologous chromosome, e.g., as occurs for different chromosomes of a heterozygous individual, or between different homozygous or heterozygous individuals in a population. A "favorable allele" is the allele at a particular locus that confers, or contributes to, an agronomically desirable phenotype, e.g., tolerance to Charcoal Rot Drought Complex, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease-prone plants. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An allele "positively" correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "locus" is a chromosomal region where a polymorphic nucleic acid, trait determinant, gene or marker is located. Thus, for example, a "gene locus" is a specific chromosome location in the genome of a species where a specific gene can be found.

The term "quantitative trait locus" or "QTL" refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

The terms "marker", "molecular marker", "marker nucleic acid", and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA or a cDNA), or from an encoded polypeptide. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele", alternatively an "allele of a marker locus", is one of a plurality of polymorphic nucleotide sequences found at a marker locus in a population that is polymorphic for the marker locus. In some aspects, the present invention provides marker loci correlating with tolerance to Charcoal Rot Drought Complex in soybean. Each of the identified markers is expected to be in close physical and genetic proximity (resulting in physical and/or genetic linkage) to a genetic element, e.g., a QTL that contributes to tolerance.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes.

Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A "genetic map" is a description of genetic linkage relationships among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map.

A "genetic recombination frequency" is the frequency of a crossing over event (recombination) between two genetic loci. Recombination frequency can be observed by following the segregation of markers and/or traits following meiosis. A genetic recombination frequency can be expressed in centimorgans (cM), where one cM is the distance between two genetic markers that show a 1% recombination frequency (i.e., a crossing-over event occurs between those two markers once in every 100 cell divisions).

As used herein, the term "linkage" is used to describe the degree with which one marker locus is "associated with" another marker locus or some other locus (for example, a tolerance locus).

As used herein, linkage equilibrium describes a situation where two markers independently segregate, i.e., sort among progeny randomly. Markers that show linkage equilibrium are considered unlinked (whether or not they lie on the same chromosome).

As used herein, linkage disequilibrium describes a situation where two markers segregate in a non-random manner, i.e., have a recombination frequency of less than 50% (and by definition, are separated by less than 50 cM on the same linkage group). Markers that show linkage disequilibrium are considered linked. Linkage occurs when the marker locus and a linked locus are found together in progeny plants more frequently than not together in the progeny plants. As used herein, linkage can be between two markers, or alternatively between a marker and a phenotype. A marker locus can be associated with (linked to) a trait, e.g., a marker locus can be associated with tolerance or improved tolerance to a plant pathogen when the marker locus is in linkage disequilibrium with the tolerance trait. The degree of linkage of a molecular marker to a phenotypic trait is measured, e.g., as a statistical probability of co-segregation of that molecular marker with the phenotype.

As used herein, the linkage relationship between a molecular marker and a phenotype is given as a "probability" or "adjusted probability". The probability value is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "insignificant". In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p=0.5). For example, a significant probability can be less than 0.25, less than 0.20, less than 0.15, or less than 0.1.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The term "physically linked" is sometimes used to indicate that two loci, e.g., two marker loci, are physically present on the same chromosome.

Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic tolerance). For example, in some aspects, these markers can be termed linked QTL markers. In other aspects, especially useful molecular markers are those markers that are linked or closely linked.

In some aspects, linkage can be expressed as any desired limit or range. For example, in some embodiments, two linked loci are two loci that are separated by less than 50 cM map units. In other embodiments, linked loci are two loci that are separated by less than 40 cM. In other embodiments, two linked loci are two loci that are separated by less than 30 cM. In other embodiments, two linked loci are two loci that are separated by less than 25 cM. In other embodiments, two linked loci are two loci that are separated by less than 20 cM. In other embodiments, two linked loci are two loci that are separated by less than 15 cM. In some aspects, it is advantageous to define a bracketed range of linkage, for example, between 10 and 20 cM, or between 10 and 30 cM, or between 10 and 40 cM.

The more closely a marker is linked to a second locus, the better an indicator for the second locus that marker becomes. Thus, in one embodiment, closely linked loci such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

As used herein, the terms "chromosome interval" or "chromosome segment" designate a contiguous linear span of genomic DNA that resides in planta on a single chromosome. The genetic elements or genes located on a single chromosome interval are physically linked. The size of a chromosome interval is not particularly limited.

In some aspects, for example in the context of the present invention, generally the genetic elements located within a single chromosome interval are also genetically linked, typically within a genetic recombination distance of, for example, less than or equal to 20 cM, or alternatively, less than or equal to 10 cM. That is, two genetic elements within a single chromosome interval undergo recombination at a frequency of less than or equal to 20% or 10%.

In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The phrase "Charcoal Rot" refers to the plant disease caused by an infection of the plant with the fungal pathogen *Macrophomina phaseolina*. While Charcoal Rot is more common in the presence of low-available water growth conditions, it can exist even in the absence of such growth conditions.

The phrase 'Charcoal Rot Drought Complex' or CRDC refers to a condition in a plant in which the disease caused by an infection with the fungal pathogen *Macrophomina phaseolina* interacts with low-available water growth conditions to subdue the plant. It is a combination of the infection of the fungus and the low-available water conditions that are most commonly encountered under field conditions. Under these field conditions, the plant is stressed by both the pathogen and environment and is subdued by the two stresses operating substantially simultaneously.

"Tolerance" or "improved tolerance" in a soybean plant to Charcoal Rot Drought Complex is an indication that the soybean plant is less affected with respect to yield and/or survivability or other relevant agronomic measures, upon introduction of the causative agents of that disease, e.g., *Macrophomina* infection and low-available water growth conditions. "Tolerance" or "improved tolerance" in a soybean plant to *Macrophomina* infection is an indication that the soybean plant is less affected with respect to yield and/or survivability or other relevant agronomic measures, upon infection of the plant with *Macrophomina* species, than a less tolerant or more "susceptible" plant. "Tolerance" or "improved tolerance" in a soybean plant to low-available water growth conditions is an indication that the soybean plant is less affected with respect to yield and/or survivability or other relevant agronomic measures, when faced with low-available water growth conditions or less-than-ideal hydration conditions, than a less tolerant or more "susceptible" plant. Tolerance is a relative term, indicating that the infected plant produces better yield of soybean than another, similarly treated, more susceptible plant. That is, the conditions cause a reduced decrease in soybean survival and/or yield in a tolerant soybean plant, as compared to a susceptible soybean plant.

One of skill will appreciate that soybean plant tolerance to Charcoal Rot Drought Complex varies widely, can represent a spectrum of more tolerant or less tolerant phenotypes, and can vary depending on the severity of the infection. However, by simple observation, one of skill can determine the relative tolerance or susceptibility of different plants, plant lines or plant families to Charcoal Rot Drought Complex, and furthermore, will also recognize the phenotypic gradations of "tolerant."

Ratings are assigned by evaluating all plants of a cultivar in a 2 row by 15 foot plot. Cultivar scores are based on a 1 to 9 system where a score of '9' would indicate that all plants in the plot are normal with no disease symptoms and a score of '1' would indicate that all plants in the plot are dead from disease. The experiments described herein score soybean tolerance to Charcoal Rot Drought Complex using the following scale: 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death. FIG. 8 gives a representative example of cultivars with vastly different Charcoal Rot Drought Complex tolerance using this scoring system.

Charcoal Rot Drought Complex "tolerance" differs from *Macrophomina* "resistance" in that tolerance is a measure of a soybean plant's ability to survive and yield soybean despite the presence of *Macrophomina* infection, as opposed to a measure of the soybean plant's ability to resist infection, just as low-available water growth condition tolerance describes a soybean plant's ability to survive and yield soybean despite the existence of low-available water growth conditions. As used in the art, "tolerance" is sometimes referred to as "general resistance", "rate-reducing resistance" or "partial resistance".

The term "crossed" or "cross" in the context of this invention means the fusion of gametes via pollination to produce progeny (e.g., cells, seeds or plants). The term encompasses both sexual crosses (the pollination of one plant by another) and selfing (self-pollination, e.g., when the pollen and ovule are from the same plant).

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, or the like. In any case, offspring comprising the desired allele can be repeatedly backcrossed to a line having a desired genetic background and selected for the desired allele, to result in the allele becoming fixed in a selected genetic background.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor. Traditionally, a "subline" has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. In the context of the invention, marker-based sublines, that differ from each other based on qualitative polymorphism at the DNA level at one or more specific marker loci, are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (yield, tolerance, etc.).

An "ancestral line" is a parent line used as a source of genes e.g., for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and its parents, grand parents, great-grand parents, etc.

An "elite line" or "elite strain" is an agronomically superior line that has resulted from many cycles of breeding and selection for superior agronomic performance. Numerous elite lines are available and known to those of skill in the art of soybean breeding. An "elite population" is an assortment of elite individuals or lines that can be used to represent the state of the art in terms of agronomically superior genotypes of a given crop species, such as soybean. Similarly, an "elite germplasm" or elite strain of germplasm is an agronomically superior germplasm, typically derived from and/or capable of giving rise to a plant with superior agronomic performance, such as an existing or newly developed elite line of soybean.

In contrast, an "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, or enhancer regions) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

An "exogenous nucleic acid" is a nucleic acid that is not native to a specified system (e.g., a germplasm, plant, or variety), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts.

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

The term "recombinant" in reference to a nucleic acid or polypeptide indicates that the material (e.g., a recombinant nucleic acid, gene, polynucleotide, or polypeptide) has been altered by human intervention. Generally, the arrangement of parts of a recombinant molecule is not a native configuration, or the primary sequence of the recombinant polynucleotide or polypeptide has in some way been manipulated. The alteration to yield the recombinant material can be performed on the material within or removed from its natural environment or state. For example, a naturally occurring nucleic acid becomes a recombinant nucleic acid if it is altered, or if it is transcribed from DNA which has been altered, by means of human intervention performed within the cell from which it originates. A gene sequence open reading frame is recombinant if that nucleotide sequence has been removed from it natural context and cloned into any type of artificial nucleic acid vector. Protocols and reagents to produce recombinant molecules, especially recombinant nucleic acids, are common and routine in the art. In one embodiment, an artificial chromosome can be created and inserted into maize plants by any method known in the art (e.g., direct transfer processes, such as, e.g., PEG-induced DNA uptake, protoplast fusion, microinjection, electroporation, and microprojectile bombardment). An artificial chromosome is a piece of DNA that can stably replicate and segregate alongside endogenous chromosomes. It has the capacity to accommodate and express heterologous genes inserted therein. Integration of heterologous DNA into the megareplicator region (primary replication initiation site of centromeres) or in close proximity thereto, initiates a large-scale amplification of megabase-size chromosomal segments, which leads to de novo chromosome formation. See, e.g., U.S. Pat. No. 6,077,697, incorporated herein by reference.

The term recombinant can also refer to an organism that harbors recombinant material, e.g., a plant that comprises a recombinant nucleic acid is considered a recombinant plant. In some embodiments, a recombinant organism is a transgenic organism.

The term "introduced" when referring to translocating a heterologous or exogenous nucleic acid into a cell refers to the incorporation of the nucleic acid into the cell using any methodology. The term encompasses such nucleic acid introduction methods as "transfection", "transformation" and "transduction".

As used herein, the term "vector" is used in reference to polynucleotide or other molecules that transfer nucleic acid segment(s) into a cell. The term "vehicle" is sometimes used interchangeably with "vector". A vector optionally comprises parts which mediate vector maintenance and enable its intended use (e.g., sequences necessary for replication, genes imparting drug or antibiotic resistance, a multiple cloning site, or operably linked promoter/enhancer elements which enable the expression of a cloned gene). Vectors are often derived from plasmids, bacteriophages, or plant or animal viruses. A "cloning vector" or "shuttle vector" or "subcloning vector" contains operably linked parts that facilitate subcloning steps (e.g., a multiple cloning site containing multiple restriction endonuclease sites).

The term "expression vector" as used herein refers to a vector comprising operably linked polynucleotide sequences that facilitate expression of a coding sequence in a particular host organism (e.g., a bacterial expression vector or a plant expression vector). Polynucleotide sequences that facilitate expression in prokaryotes typically include, e.g., a promoter, an operator (optional), and a ribosome binding site, often along with other sequences. Eukaryotic cells can use promoters, enhancers, termination and polyadenylation signals and other sequences that are generally different from those used by prokaryotes.

The term "transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

A specified nucleic acid is "derived from" a given nucleic acid when it is constructed using the given nucleic acid's sequence, or when the specified nucleic acid is constructed using the given nucleic acid. For example, a cDNA or EST is derived from an expressed mRNA.

The term "genetic element" or "gene" refers to a heritable sequence of DNA, i.e., a genomic sequence, with functional significance. The term "gene" can also be used to refer to, e.g., a cDNA and/or a mRNA encoded by a genomic sequence, as well as to that genomic sequence.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome segment.

The terms "phenotype", or "phenotypic trait" or "trait" refers to one or more trait of an organism. The phenotype can be observable to the naked eye, or by any other means of evaluation known in the art, e.g., microscopy, biochemical analysis, genomic analysis, or an assay for a particular disease resistance. In some cases, a phenotype is directly controlled by a single gene or genetic locus, i.e., a "single gene trait". In other cases, a phenotype is the result of several genes.

A "molecular phenotype" is a phenotype detectable at the level of a population of (one or more) molecules. Such molecules can be nucleic acids such as genomic DNA or RNA, proteins, or metabolites. For example, a molecular phenotype can be an expression profile for one or more gene products, e.g., at a specific stage of plant development, in response to an environmental condition or stress, etc. Expression profiles are typically evaluated at the level of RNA or protein, e.g., on a nucleic acid array or "chip" or using antibodies or other binding proteins.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

A "set" of markers or probes refers to a collection or group of markers or probes, or the data derived therefrom, used for a common purpose, e.g., identifying soybean plants with a desired trait (e.g., tolerance to Charcoal Rot Drought Complex). Frequently, data corresponding to the markers or probes, or data derived from their use, is stored in an electronic medium. While each of the members of a set possess utility with respect to the specified purpose, individual markers selected from the set as well as subsets including some, but not all of the markers, are also effective in achieving the specified purpose.

A "look up table" is a table that correlates one form of data to another, or one or more forms of data with a predicted outcome that the data is relevant to. For example, a look up table can include a correlation between allele data and a predicted trait that a plant comprising a given allele is likely to display. These tables can be, and typically are, multidimensional, e.g., taking multiple alleles into account simultaneously, and, optionally, taking other factors into account as well, such as genetic background, e.g., in making a trait prediction.

A "computer readable medium" is an information storage media that can be accessed by a computer using an available or custom interface. Examples include memory (e.g., ROM, RAM, or flash memory), optical storage media (e.g., CD-ROM), magnetic storage media (computer hard drives, floppy disks, etc.), punch cards, and many others that are commercially available. Information can be transmitted between a system of interest and the computer, or to or from the computer to or from the computer readable medium for storage or access of stored information. This transmission can be an electrical transmission, or can be made by other available methods, such as an IR link, a wireless connection, or the like.

"System instructions" are instruction sets that can be partially or fully executed by the system. Typically, the instruction sets are present as system software.

BRIEF DESCRIPTION OF THE DRAWINGS AND SEQUENCES

FIG. 1 provides a table listing soybean markers demonstrating linkage disequilibrium with the Charcoal Rot Drought Complex tolerance phenotype as determined by intergroup allele frequency distribution analysis, association mapping analysis, QTL interval mapping (including single marker regression analysis), and marker regression and interval mapping analysis using MapManager. The table indicates the genomic-SSR or EST-SSR marker type (all simple sequence repeats) or SNP markers, the chromosome on which the marker is located and its approximate genetic map position relative to other known markers, given in cM, with position zero being the first (most distal) marker on the chromosome, as provided in the integrated genetic map in FIG. 6. Also shown are the soybean populations used in the analysis and the statistical probability of random segregation of the marker and the tolerance/susceptibility phenotype given as an adjusted probability taking into account the variability and false positives of multiple tests. Probability values from single marker regression are also shown.

FIG. 2 provides a table listing genomic and EST SSR markers, including those markers that demonstrated linkage disequilibrium with the Charcoal Rot Drought Complex tolerance phenotype. The table provides the sequences of the left and right PCR primers used in the SSR marker locus genotyping analysis. Also shown is the pigtail sequence used on the 5' end of the right primer, and the number of nucleotides in the tandem repeating element in the SSR.

FIG. 3 provides a table listing the SNP markers that demonstrated linkage disequilibrium with the Charcoal Rot Drought Complex tolerance phenotype. The table provides the sequences of the PCR primers used to generate a SNP-containing amplicon, and the allele-specific probes that were used to identify the SNP allele in an allele-specific hybridization assay (ASH assay).

FIG. 4 provides an allele dictionary for the alleles of the SSR markers shown in FIG. 1, including those markers that demonstrated linkage disequilibrium with the Charcoal Rot Drought Complex tolerance phenotype. Each allele is defined by the size of a PCR amplicon generated from soybean genomic DNA or mRNA using the primers listed in FIG. 2. Sizes of the PCR amplicons are indicated in base pairs (bp).

FIG. 5 provides a table listing genetic markers that are linked and genetic markers that are closely linked to the Charcoal Rot Drought Complex tolerance markers identified by the present invention.

FIG. 6 (6.1-6.21) provides an integrated genetic map of soybean markers. These markers are distributed over each soybean chromosome. The genetic map positions of the markers are indicated in centiMorgans (cM), typically with position zero being the first (most distal) marker on the chromosome. The markers within the linked interval, and closely linked interval around a central marker are indicated.

FIG. 7 provides a table listing the soybean lines used in the current Charcoal Rot Drought Complex tolerance analysis, the Charcoal Rot Drought Complex tolerance score of each line used, and whether the particular line was used in the Trait Allele and/or InterGroup analyses.

FIG. 8 provides an example of cultivars with vastly different Charcoal Rot Drought Complex tolerance scores. Using the scoring system described herein, the two row plot of one cultivar of soybean plants on the left scored a 6 while the two row plot of a different cultivar of soybean plants on the right scored a 1. This was based on the determination that the two row plot of one cultivar of soybean plants on the left had wilting at the uppermost three nodes and leaflet yellowing beginning appear, while the two row plot of a different cultivar of soybean plants on the right had near 100% plant death.

DETAILED DESCRIPTION OF THE INVENTION

Charcoal Rot is a disease of soybean, causing reduced plant viability and reductions in yield. This disease is caused by infection of the plant with *Macrophomina* phaseolina, a fungal pathogen. Though this disease is most prevalent during low-available water growth conditions, it can exist even in the absence of such growth conditions. While *Macrophomina* resistant plants have been previously developed, the strong selective pressures that resistant soybean impose on *Macrophomina* is likely to cause relatively rapid loss of resistance against races of *Macrophomina* that evolve to combat resistance traits in the resistant soybean, as has been seen with other soybean fungal pathogens, such as *Sclerotinia*. Accordingly, tolerance to Charcoal Rot and/or *Macrophomina* infection, in which the plant survives, thrives and produces high yields, despite a productive *Macrophomina* infection, is an alternate strategy to combat losses due to Charcoal Rot and/or *Macrophomina* infection. That is, there is not a strong negative selection against *Macrophomina* imposed by tolerance, because tolerant soybean plants support a productive *Macrophomina* infection.

Further, as plant stress caused by low-available water growth conditions is related to the existence and severity of Charcoal Rot and/or *Macrophomina* infection, with plants showing reduced survivability and yield from these conditions when coupled with low-available water growth conditions, soybean plants tolerant to low-available water growth conditions would show increased Charcoal Rot and/or *Macrophomina* infection tolerance, as well, and are therefore desirable. In addition, as low-available water growth condition is itself a major cause of loss of plant viability and yield, even in the absence of Charcoal Rot and/or *Macrophomina* infection, plants tolerant to such growth conditions are desirable for their direct benefits, not related to Charcoal Rot as well.

The identification and selection of soybean plants that show tolerance to Charcoal Rot Drought Complex using MAS can provide an effective and environmentally friendly approach to overcoming losses caused by this disease. The present invention provides soybean marker loci that demonstrate statistically significant co-segregation with Charcoal Rot Drought Complex tolerance. Detection of these loci or additional linked loci can be used in marker assisted soybean breeding programs to produce tolerant plants, or plants with improved tolerance. The linked SSR and SNP markers identified herein are provided in FIG. 1. These markers include Sct_028, Satt512, S60211-TB, Sat_117, S01954-1-A, P13158A, S63880-CB, S00415-1-A, S00705-1-A, and S02118-1-A.

Each of the SSR-type markers display a plurality of alleles that can be visualized as different sized PCR amplicons, as summarized in the SSR allele dictionary in FIG. 4. The PCR primers that are used to generate the SSR-marker amplicons are provided in FIG. 2. The alleles of SNP-type markers are determined using an allele-specific hybridization protocol, as known in the art. The PCR primers used to amplify the SNP domain, and the allele-specific probes used to genotype the locus are provided in FIG. 3.

As recognized in the art, any other marker that is linked to a QTL marker (e.g., a disease tolerance marker) also finds use for that same purpose. Examples of additional markers that are linked to the disease tolerance markers recited herein are provided. For example, a linked marker can be determined from the soybean consensus genetic map provided in FIG. 6. Additional linked and closely linked markers are further provided in FIG. 5. It is not intended, however, that linked markers finding use with the invention be limited to those recited in FIG. 5 or 6.

The invention also provides chromosomal QTL intervals that correlate with Charcoal Rot Drought Complex tolerance. These intervals are located on linkage groups C2, E, B2, G, H, B1, C1, D1b and N. Any marker located within these intervals finds use as a marker for Charcoal Rot Drought Complex tolerance. These intervals include:
  (i) Satt286 and Satt371 (LG-C2);
  (ii) Satt575 and Sat_136 (LG-E);
  (iii) Satt467 and Satt416 (LG-B2);
  (iv) Satt612 and A681_1 (LG-G);
  (v) Sat_158 and A162_1 (LG-H);
  (vi) Satt444 and Sat_331 (LG-B1);
  (vii) Bng019_1 and Sct_191 (LG-C1);
  (viii) A605_1 and A519_2 (LG-D1b); and,
  (xi) Sat_306 and A363_3 (LG-N).

Methods for identifying soybean plants or germplasm that carry preferred alleles of tolerance marker loci are a feature of the invention. In these methods, any of a variety of marker detection protocols is used to identify marker loci, depending on the type of marker loci. Typical methods for marker detection include amplification and detection of the resulting amplified markers, e.g., by PCR, LCR, transcription based amplification methods, or the like. These include ASH, SSR detection, RFLP analysis and many others.

Although particular marker alleles can show co-segregation with a disease tolerance or susceptibility phenotype, it is important to note that the marker locus is not necessarily part of the QTL locus responsible for the tolerance or susceptibility. For example, it is not a requirement that the marker polynucleotide sequence be part of a gene that imparts disease resistance (for example, be part of the gene open reading frame). The association between a specific marker allele with the tolerance or susceptibility phenotype is due to the original "coupling" linkage phase between the marker allele and the QTL tolerance or susceptibility allele in the ancestral soybean line from which the tolerance or susceptibility allele originated. Eventually, with repeated recombination, crossing over events between the marker and QTL locus can change this orientation. For this reason, the favorable marker allele may change depending on the linkage phase that exists within the tolerant parent used to create segregating populations. This does not change the fact that the genetic marker can be used to monitor segregation of the phenotype. It only changes which marker allele is considered favorable in a given segregating population.

Identification of soybean plants or germplasm that include a marker locus or marker loci linked to a tolerance trait or traits provides a basis for performing marker assisted selection of soybean. Soybean plants that comprise favorable markers or favorable alleles are selected for, while soybean plants that comprise markers or alleles that are negatively correlated with tolerance can be selected against. Desired markers and/or alleles can be introgressed into soybean having a desired (e.g., elite or exotic) genetic background to produce an introgressed tolerant soybean plant or germplasm. In some aspects, it is contemplated that a plurality of tolerance markers are sequentially or simultaneous selected and/or introgressed. The combinations of tolerance markers that are selected for in a single plant is not limited, and can include any combination of markers recited in FIG. 1, any markers linked to the markers recited in FIG. 1, or any markers located within the QTL intervals defined herein.

Various methods are known in the art for determining (and measuring) the tolerance of a soybean plant to Charcoal Rot Drought Complex. They describe a tolerance measurement scale of 1-9, with 9=no disease and 1=total necrosis caused by *Macrophomina phaseolina*. It will be appreciated that all such scales are relative and that numbering and precise correlation to any scale can be performed at the discretion of the practitioner.

Typically, individual field tests are monitored for Charcoal Rot symptoms during the middle to late vegetative stages, but such symptoms typically appear in the early reproductive stage (during flowering and early pod set). Data collection is usually done in 3 or 4 successive scorings about 7 days apart. Scorings continue until worsening symptoms can no longer be quantified or until the symptoms are confounded by other factors such as other diseases, insect pressure, severe weather, or advancing maturity.

In general, while there is a certain amount of subjectivity to assigning severity measurements for disease caused symptoms, assignment to a given scale as noted above is well within the skill of a practitioner in the field. Measurements can also be averaged across multiple scorers to reduce variation in field measurements. Furthermore, although protocols using artificial inoculation of field nurseries with *Macrophomina phaseolina* can certainly be used in assessing tolerance, it is also typical for tolerance ratings to be based on actual field observations of fortuitous natural disease incidence, with the information corresponding to disease incidence for a cultivar being averaged over many locations and, typically, several years of crop growing.

If there is no disease present, the rating system above is inapplicable, because everything in an uninfected field scores as tolerant. However, if Charcoal Rot does occur in a specific field location, all of the lines at that location can be scored as noted above. These scores can accumulate over locations and years to show disease tolerance for given cultivars. Thus, older lines can have more years of observation than newer ones etc. However, relative measurements can easily be made using the scoring system noted above. Furthermore, the tolerance ratings can be updated and refined each year based on the previous year's observations in the field. Based on this, Charcoal Rot scores for a cultivar are relative measurements of tolerance.

The experiments described herein score soybean tolerance to Charcoal Rot Drought Complex using the following scale: 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death. FIG. 8 gives a representative example of cultivars with vastly different Charcoal Rot Drought Complex tolerance using this scoring system.

Tolerance assays are useful to verify that the tolerance trait still segregates with the marker in any particular plant or population, and, of course, to measure the degree of tolerance improvement achieved by introgressing or recombinantly introducing the trait into a desired background.

Systems, including automated systems for selecting plants that comprise a marker of interest and/or for correlating presence of the marker with tolerance are also a feature of the invention. These systems can include probes relevant to marker locus detection, detectors for detecting labels on the probes, appropriate fluid handling elements and temperature controllers that mix probes and templates and/or amplify templates, and systems instructions that correlate label detection to the presence of a particular marker locus or allele.

Kits are also a feature of the invention. For example, a kit can include appropriate primers or probes for detecting tolerance associated marker loci and instructions in using the primers or probes for detecting the marker loci and correlating the loci with predicted Charcoal Rot Drought Complex tolerance. The kits can further include packaging materials for packaging the probes, primers or instructions, controls such as control amplification reactions that include probes, primers or template nucleic acids for amplifications, molecular size markers, or the like.

Tolerance Markers and Favorable Alleles

In traditional linkage analysis, no direct knowledge of the physical relationship of genes on a chromosome is required. Mendel's first law is that factors of pairs of characters are segregated, meaning that alleles of a diploid trait separate into two gametes and then into different offspring. Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked". The frequency with which the traits are inherited together is the primary measure of how tightly the traits are linked, i.e., traits which are inherited together with a higher frequency are more closely linked than traits which are inherited together with lower (but still above random) frequency. Traits are linked because the genes which underlie the traits reside on the same chromosome. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in two genes segregating separately into progeny.

A common measure of linkage is the frequency with which traits cosegregate. This can be expressed as a percentage of cosegregation (recombination frequency) or, also commonly, in centiMorgans (cM). The cM is named after the pioneering geneticist Thomas Hunt Morgan and is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency. For example, in soybean, 1 cM correlates, on average, to about 400,000 base pairs (400 Kb).

Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation. The markers herein, as described in FIG. 1, e.g., Sct_028, Satt512, S60211-TB, Sat_117, S01954-1-A, P13158A, S63880-CB, S00415-1-A, S00705-1-A, S02118-1-A as well as any of the chromosome intervals:

(i) Satt286 and Satt371 (LG-C2);
(ii) Satt575 and Sat_136 (LG-E);
(iii) Satt467 and Satt416 (LG-B2);
(iv) Satt612 and A681_1 (LG-G);
(v) Sat_158 and A162_1 (LG-H);
(vi) Satt444 and Sat_331 (LG-B1);
(vii) Bng019_1 and Sct_191 (LG-C1);
(viii) A605_1 and A519_2 (LG-D1b); and,
(xi) Sat_306 and A363_3 (LG-N)

have been found to correlate with tolerance, improved tolerance or susceptibility to Charcoal Rot Drought Complex in soybean. This means that the markers are sufficiently proximal to a tolerance trait that they can be used as a predictor for the tolerance trait. This is extremely useful in the context of marker assisted selection (MAS), discussed in more detail herein. In brief, soybean plants or germplasm can be selected for markers or marker alleles that positively correlate with tolerance, without actually raising soybean and measuring for tolerance or improved tolerance (or, contrarily, soybean plants can be selected against if they possess markers that negatively correlate with tolerance or improved tolerance). MAS is a powerful shortcut to selecting for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the most preferred QTL markers are a subset of the markers provided in FIG. 1. For example, the most preferred markers are Satt512, SCT_028, S60211-TB, Sat_177, S01954-1-A, and S00415-1-A.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

A favorable allele of a marker is that allele of the marker that co-segregates with a desired phenotype (e.g., disease tolerance). As used herein, a QTL marker has a minimum of one favorable allele, although it is possible that the marker might have two or more favorable alleles found in the population. Any favorable allele of that marker can be used advantageously for the identification and construction of tolerant soybean lines. Optionally, one, two, three or more favorable allele(s) of different markers are identified in, or introgressed into a plant, and can be selected for or against during MAS. Desirably, plants or germplasm are identified that have at least one such favorable allele that positively correlates with tolerance or improved tolerance.

Alternatively, a marker allele that co-segregates with disease susceptibility also finds use with the invention, since that allele can be used to identify and counter select disease-susceptible plants. Such an allele can be used for exclusionary purposes during breeding to identify alleles that negatively correlate with tolerance, to eliminate susceptible plants or germplasm from subsequent rounds of breeding.

In some embodiments of the invention, a plurality of marker alleles are simultaneously selected for in a single plant or a population of plants. In these methods, plants are selected that contain favorable alleles from more than one tolerance marker, or alternatively, favorable alleles from more than one tolerance marker are introgressed into a desired soybean germplasm. One of skill in the art recognizes that the simultaneous selection of favorable alleles from more than one disease tolerance marker in the same plant is likely to result in an additive (or even synergistic) protective effect for the plant.

One of skill recognizes that the identification of favorable marker alleles is germplasm-specific. The determination of which marker alleles correlate with tolerance (or susceptibility) is determined for the particular germplasm under study. One of skill recognizes that methods for identifying the favorable alleles are routine and well known in the art, and furthermore, that the identification and use of such favorable alleles is well within the scope of the invention. Furthermore still, identification of favorable marker alleles in soybean populations other than the populations used or described herein is well within the scope of the invention.

Amplification primers for amplifying SSR-type marker loci are a feature of the invention. Another feature of the invention is primers specific for the amplification of SNP domains (SNP markers), and the probes that are used to genotype the SNP sequences. FIGS. 2 and 3 provide specific primers for marker locus amplification and probes for detecting amplified marker loci. However, one of skill will immediately recognize that other sequences to either side of the given primers can be used in place of the given primers, so long as the primers can amplify a region that includes the allele to be detected. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the invention is not limited to the primers and probes specifically recited herein.

In some aspects, methods of the invention utilize an amplification step to detect/genotype a marker locus. However, it will be appreciated that amplification is not a requirement for marker detection—for example, one can directly detect unamplified genomic DNA simply by performing a Southern blot on a sample of genomic DNA. Procedures for performing Southern blotting, amplification (PCR, LCR, or the like) and many other nucleic acid detection methods are well established and are taught, e.g., in Sambrook, et al., (2000) *Molecular Cloning—A Laboratory Manual* (3rd Ed.), Vol. 1-3, Cold Spring Harbor Laboratory, Cold Spring Harbor, N.Y., ("Sambrook"); *Current Protocols in Molecular Biology*, Ausubel, et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis, et al., eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Typically, molecular markers are detected by any established method available in the art, including, without limitation, allele specific hybridization (ASH) or other methods for detecting single nucleotide polymorphisms (SNP), amplified fragment length polymorphism (AFLP) detection, amplified variable sequence detection, randomly amplified polymorphic DNA (RAPD) detection, restriction fragment length polymorphism (RFLP) detection, self-sustained sequence replication detection, simple sequence repeat (SSR) detection, single-strand conformation polymorphisms (SSCP) detection, isozyme markers detection, or the like. Any of the aforementioned marker types can be employed in the context of the invention to identify chromosome segments encompassing genetic element that contribute to superior agronomic performance (e.g., tolerance or improved tolerance).

QTL Chromosome Intervals

In some aspects, the invention provides QTL chromosome intervals, where a QTL (or multiple QTLs) that segregate with Charcoal Rot Drought Complex tolerance are contained in those intervals. A variety of methods well known in the art are available for identifying chromosome intervals (also as described in detail in Example 1). The boundaries of such chromosome intervals are drawn to encompass markers that will be linked to one or more QTL. In other words, the chromosome interval is drawn such that any marker that lies within that interval (including the terminal markers that define the boundaries of the interval) can be used as markers for disease tolerance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifying the same QTL or two different QTL. Regardless, knowledge of how many QTL are in a particular interval is not necessary to make or practice the invention.

The present invention provides soybean chromosome intervals, where the markers within that interval demonstrate co-segregation with tolerance to Charcoal Rot Drought Complex. Thus, each of these intervals comprises at least one Charcoal Rot Drought Complex tolerance QTL. These intervals are:

| Linkage Group | Flanking Markers | Method(s) of Identification |
|---|---|---|
| C2 | Satt286 and Satt371 | Trait Allele Correlation and Intergroup Analysis |
| E | Satt575 and Sat_136 | Trait Allele Correlation and Intergroup Analysis |
| B2 | Satt467 and Satt416 | Intergroup Analysis |
| G | Sat_158 and A681_1 | Trait Allele Correlation and Intergroup Analysis |
| H | Satt444 and A162_1 | Trait Allele Correlation |
| B1 | Satt444 and Sat_331 | Trait Allele Correlation |
| C1 | Bng019_1 and Sct_191 | Marker Regression and Interval Mapping Analysis |
| D1b | A605_1 and A519_2 | Marker Regression and Interval Mapping Analysis |
| N | Sat_306 and A363_3 | Marker Regression and Interval Mapping Analysis |

Each of the intervals described above shows a clustering of markers that co-segregate with Charcoal Rot Drought Complex tolerance. This clustering of markers occurs in relatively small domains on the linkage groups, indicating the presence of one or more QTL in those chromosome regions. QTL intervals were drawn to encompass the markers that co-segregate with tolerance. The intervals are defined by the markers on their termini, where the interval encompasses all the markers that map within the interval as well as the markers that define the termini.

In some cases, an interval can be drawn, where the interval is defined by linkage to a preferred marker. For example, an interval on LG-C2 is defined where any marker that is linked to the marker Sct_028 is a member of that interval. For example, as used here, linkage is defined as any marker that is within 25 cM from Sct_028. This interval on LG-C2 is further illustrated in FIG. 5. The experimentally demonstrated marker Sct_028 is shown, as are markers that are linked to Sct_028 (e.g., within 25 cM of Sct_028) as determined by any suitable genetic linkage map (for example, the GmComposite 2003 map found on the Soybase website). These markers are shown in genetic order. Each of the markers listed, including the terminal markers Satt286 and Satt371, are members of the interval. The Satt286 and Satt371 markers are known in the art.

As described above, an interval (e.g., a chromosome interval or a QTL interval) need not depend on an absolute measure of interval size such as a centimorgans value. An interval can be described by the terminal markers that define the endpoints of the interval, and typically the interval will include the terminal markers that define the extent of the interval. An interval can include any marker localizing within that chromosome domain, whether those markers are currently known or unknown. In situations where the interval is close to or comprises one end of the linkage group, the interval can be described by one marker, for example the interval on linkage group G can be described as including marker Satt612 and below, the interval on linkage group N can be described as including marker Sat_306 and below, and the interval on linkage group E can be described as including marker Sat_136 and above, where "above" and "below" are the terms commonly used in the art to describe the marker's position relative to the distal end (position zero), with above being closer to position zero. The invention provides a variety of means for defining a chromosome interval, for example, the marker loci provided in the genetic map in FIG. 6, in the lists of linked markers of FIG. 5, and in references cited herein (e.g., Song, et al., (2004) "A New Integrated Genetic Linkage Map of the Soybean" *Theor Appl Genet* 109:122-128).

Genetic Maps

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL/marker genetic map relationships. However, it is not intended that the invention be limited to any particular mapping populations, use of any particular software, or any particular set of software parameters to determine linkage of a particular marker or chromosome interval with the Charcoal Rot Drought Complex tolerance phenotype. It is well within the ability of one of ordinary skill in the art to extrapolate the novel features described herein to any soybean gene pool or population of interest, and using any particular software and software parameters. Indeed, observations regarding tolerance markers and chromosome intervals in populations in additions to those described herein are readily made using the teaching of the present disclosure.

Mapping Populations

Any suitable soybean strains can be used to generate mapping data or for marker association studies. A large number of commonly used soybean lines (e.g., commercial varieties) and mapping populations are known in the art. A broad range of mapping populations was used in the current study, including, but not limited to those listed in FIG. 7.

Mapping Software

A variety of commercial software is available for genetic mapping and marker association studies (e.g., QTL mapping). This software includes but is not limited to:

| Software | Description/References |
|---|---|
| JoinMap ® | VanOoijen, and Voorrips (2001) "JoinMap 3.0 software for the calculation of genetic linkage maps," Plant Research International, Wageningen, the Netherlands; and, Stam "Construction of integrated genetic linkage maps by means of |

| Software | Description/References |
|---|---|
| | a new computer package: JoinMap" The Plant Journal 3(5): 739-744 (1993) |
| MapQTL ® | J. W. vanOoijen, "Software for the mapping of quantitative trait loci in experimental populations" Kyazma B. V., Wageningen, Netherlands |
| MapManager QT | Manly and Olson, "Overview of QTL mapping software and introduction to Map Manager QT" Mamm. Genome 10: 327-334 (1999) |
| MapManager QTX | Manly, Cudmore and Meer, "MapManager QTX, cross-platform software for genetic mapping" Mamm. Genome 12: 930-932 (2001) |
| GeneFlow ® and QTLocate ™ | GENEFLOW, Inc. (Alexandria, VA) |
| TASSEL | (Trait Analysis by aSSociation, Evolution, and Linkage) by Edward Buckler, and information about the program can be found on the Buckler Lab web page at the Institute for Genomic Diversity at Cornell University. |

Unified Genetic Maps

"Unified", "consensus" or "integrated" genetic maps have been created that incorporate mapping data from two or more sources, including sources that used different mapping populations and different modes of statistical analysis. The merging of genetic map information increases the marker density on the map, as well as improving map resolution. These improved maps can be advantageously used in marker assisted selection, map-based cloning, provide an improved framework for positioning newly identified molecular markers and aid in the identification of QTL chromosome intervals and clusters of advantageously-linked markers.

In some aspects, a consensus map is derived by simply overlaying one map on top of another. In other aspects, various algorithms, e.g., JoinMap® analysis, allows the combination of genetic mapping data from multiple sources, and reconciles discrepancies between mapping data from the original sources. See, Van Ooijen, and Voorrips (2001) "Join-Map 3.0 software for the calculation of genetic linkage maps," Plant Research International, Wageningen, the Netherlands; and, Stam (1993) "Construction of integrated genetic linkage maps by means of a new computer package: Join-Map," *The Plant Journal* 3(5):739-744.

FIG. 6 provides a composite genetic map that incorporates mapping information from various sources. The markers that are on this map are known in the art (i.e., have been previously described; see, e.g., the SOYBASE on-line resource for extensive listings of these markers and descriptions of the individual markers) or are described herein.

Additional integrated maps are known in the art. See, e.g., Cregan, et al., (1999) "An Integrated Genetic Linkage Map of the Soybean Genome", *Crop Science* 39:1464-1490; and also, International Application Number PCT/US2004/024919 by Sebastian, filed Jul. 27, 2004, entitled "Soybean Plants Having Superior Agronomic Performance and Methods for their Production".

Song, et al., provides another integrated soybean genetic map that incorporates mapping information from five different mapping populations (Song, et al., (2004) "A New Integrated Genetic Linkage Map of the Soybean," *Theor Appl Genet* 109:122-128). This integrated map contains approximately 1,800 soybean markers, including SSR and SNP-type markers, as well as EST markers, RFLP markers, AFLP, RAPD, isozyme and classical markers (e.g., seed coat color). The markers that are on this map are known in the art and have been previously characterized. This information is also available at the website for the Soybean Genomics and Improvement Laboratory (SGIL) at the USDA Beltsville Agricultural Research Center (BARC). See, specifically, the description of projects in the Cregan Laboratory on that website.

The soybean integrated linkage map provided in Song, et al., (2004) is based on the principle described by Stam (1993) "Construction of integrated genetic linkage maps by means of a new computer package: JoinMap," *The Plant Journal* 3(5): 739-744; and Van Ooijen and Voorrips (2001) "JoinMap 3.0 software for the calculation of genetic linkage maps," Plant Research International, Wageningen, the Netherlands. Mapping information from five soybean populations was used in the map integration, and also used to place recently identified SSR markers onto the soybean genome. These mapping populations were Minsoy×Noir 1 (MN), Minsoy×Archer (MA), Noir 1×Archer (NA), Clark×Harosoy (CH) and A81-356022×P1468916 (MS). The JoinMap® analysis resulted in a map with 20 linkage groups containing a total of 1849 markers, including 1015 SSRs, 709 RFLPs, 73 RAPDs, 24 classical traits, six AFLPs, ten isozymes and 12 others. Among the mapped SSR markers were 417 previously uncharacterized SSRs.

Initially, LOD scores and pairwise recombination frequencies between markers were calculated. A LOD of 5.0 was used to create groups in the MS, MA, NA populations and LOD 4.0 in the MN and CH populations. The map of each linkage group was then integrated. Recombination values were converted to genetic distances using the Kosambi mapping function.

Linked Markers

From the present disclosure and widely recognized in the art, it is clear that any genetic marker that has a significant probability of co-segregation with a phenotypic trait of interest (e.g., in the present case, a tolerance or improved tolerance trait) can be used as a marker for that trait. A list of useful QTL markers provided by the present invention is provided in FIG. 1.

In addition to the QTL markers noted in FIG. 1, additional markers linked to (showing linkage disequilibrium with) the QTL markers can also be used to predict the tolerance or improved tolerance trait in a soybean plant. In other words, any other marker showing less than 50% recombination frequency (separated by a genetic distance less than 50 cM) with a QTL marker of the invention (e.g., the markers provided in FIG. 1) is also a feature of the invention. Any marker that is linked to a QTL marker can also be used advantageously in marker-assisted selection for the particular trait.

Genetic markers that are linked to QTL markers (e.g., QTL markers provided in FIG. 1) are particularly useful when they are sufficiently proximal (e.g., closely linked) to a given QTL marker so that the genetic marker and the QTL marker display a low recombination frequency. In the present invention, such closely linked markers are a feature of the invention. As defined herein, closely linked markers display a recombination frequency of about 10% or less (the given marker is within 10 cM of the QTL). Put another way, these closely linked loci co-segregate at least 90% of the time. Indeed, the closer a marker is to a QTL marker, the more effective and advantageous that marker becomes as an indicator for the desired trait.

Thus, in other embodiments, closely linked loci such as a QTL marker locus and a second locus display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus such as a QTL) display a recombination a frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

In some aspects, linked markers (including closely linked markers) of the invention are determined by review of a genetic map, for example, the integrated genetic map shown in FIG. 6. For example, it is shown herein that the linkage group LG-C2 marker Sct_028 correlates with at least one Charcoal Rot Drought Complex tolerance QTL. Markers that are linked to Sct_028 can be determined from the map provided in FIG. 6. For example, SSR markers on linkage group LG-C2 that are linked to Sct_028 include:

| Marker | Map Position |
| --- | --- |
| Satt286 | 101.75 |
| Sat_402 | 103.33 |
| Satt277 | 107.58 |
| Satt365 | 111.68 |
| Satt205 | 112.18 |
| Satt557 | 112.19 |
| Satt289 | 112.34 |
| Satt134 | 112.83 |
| Sat_312 | 112.84 |
| Satt489 | 113.38 |
| Satt319 | 113.41 |
| Satt658 | 113.62 |
| AG36 | 113.69 |
| Satt100 | 113.95 |
| Sat_251 | 114.19 |
| Sat_142 | 115.09 |
| Satt708 | 115.48 |
| Sat_238 | 117.45 |
| Satt460 | 117.76 |
| Satt079 | 117.87 |
| Sat_263 | 118.77 |
| Staga001 | 119.84 |
| Satt307 | 121.26 |
| Sct_028 | 122.01 |
| Satt202 | 126.23 |

-continued

| Marker | Map Position |
| --- | --- |
| Sat_252 | 127.00 |
| Satt316 | 127.66 |
| Satt433 | 128.22 |
| Satt371 | 145.47 |

In other aspects, closely linked markers of the invention can be determined by review of this same genetic map. For example, SSR markers that are closely linked (e.g., separated by not more than 10 cM) to Sct_028 on linkage group LG-C2 include:

| Marker | Map Position |
| --- | --- |
| Satt205 | 112.18 |
| Satt557 | 112.19 |
| Satt289 | 112.34 |
| Satt134 | 112.83 |
| Sat_312 | 112.84 |
| Satt489 | 113.38 |
| Satt319 | 113.41 |
| Satt658 | 113.62 |
| AG36 | 113.69 |
| Satt100 | 113.95 |
| Sat_251 | 114.19 |
| Sat_142 | 115.09 |
| Satt708 | 115.48 |
| Sat_238 | 117.45 |
| Satt460 | 117.76 |
| Satt079 | 117.87 |
| Sat_263 | 118.77 |
| Staga001 | 119.84 |
| Satt307 | 121.26 |
| Sct_028 | 122.01 |
| Satt202 | 126.23 |
| Sat_252 | 127.00 |
| Satt316 | 127.66 |
| Satt433 | 128.22 |

Markers that are linked to Satt512 can be determined from the map provided in FIG. 6. For example, SSR markers on linkage group LG-E that are linked to Satt512 include:

| Marker | Map Position |
| --- | --- |
| Satt575 | 3.30 |
| Satt213 | 3.72 |
| Sat_112 | 8.67 |
| Satt411 | 12.92 |
| Sat_124 | 15.86 |
| Satt512 | 16.73 |
| Satt384 | 19.29 |
| Satt691 | 19.70 |
| Satt720 | 20.79 |
| Satt651 | 32.09 |
| Satt212 | 32.27 |
| Satt598 | 34.20 |
| Satt573 | 35.79 |
| Sat_136 | 39.16 |

In other aspects, closely linked markers of the invention can be determined by review of this same genetic map. For example, SSR markers that are closely linked (e.g., separated by not more than 10 cM) to Satt512 on linkage group LG-E include:

| Marker | Map Position |
|---|---|
| Sat_112 | 8.67 |
| Satt411 | 12.92 |
| Sat_124 | 15.86 |
| Satt512 | 16.73 |
| Satt384 | 19.29 |
| Satt691 | 19.70 |
| Satt720 | 20.79 |

Markers that are linked to S60211-TB can be determined from the map provided in FIG. 6. For example, SSR markers on linkage group LG-B2 that are linked to S60211-TB include:

| Marker | Map Position |
|---|---|
| Satt467 | 17.77 |
| Sat_342 | 20.30 |
| Satt126 | 27.62 |
| Sat_287 | 31.87 |
| S60211-TB | 36.51 |
| Sct_034 | 51.45 |
| Satt083 | 51.49 |
| Satt168 | 55.20 |
| Satt416 | 56.95 |

In other aspects, closely linked markers of the invention can be determined by review of this same genetic map. For example, SSR markers that are closely linked (e.g., separated by not more than 10 cM) to S60211-TB on linkage group LG-B2 include:

| Marker | Map Position |
|---|---|
| Satt126 | 27.62 |
| Sat_287 | 31.87 |
| S60211-TB | 36.51 |

Markers that are linked to Sat_117 can be determined from the map provided in FIG. 6. For example, SSR markers on linkage group LG-G that are linked to Sat_117 include:

| Marker | Map Position |
|---|---|
| Satt612 | 80.37 |
| AF162283 | 87.94 |
| Sct_199 | 94.40 |
| Satt472 | 94.83 |
| Satt191 | 96.57 |
| Sat_117 | 100.00 |
| Sct_187 | 107.11 |
| Sat_372 | 107.75 |
| Sat_064 | 108.69 |

In other aspects, closely linked markers of the invention can be determined by review of this same genetic map. For example, SSR markers that are closely linked (e.g., separated by not more than 10 cM) to Sat_117 on linkage group LG-G include:

| Marker | Map Position |
|---|---|
| Sct_199 | 94.40 |
| Satt472 | 94.83 |
| Satt191 | 96.57 |
| Sat_117 | 100.00 |

-continued

| Marker | Map Position |
|---|---|
| Sct_187 | 107.11 |
| Sat_372 | 107.75 |
| Sat_064 | 108.69 |

Markers that are linked to P13158A can be determined from the map provided in FIG. 6. For example, SSR markers on linkage group LG-H that are linked to P13158A include:

| Marker | Map Position |
|---|---|
| Sat_158 | 73.45 |
| Satt302 | 81.04 |
| Sat_175 | 83.19 |
| Sat_216 | 85.26 |
| Satt637 | 85.79 |
| Satt142 | 86.48 |
| Satt293 | 89.08 |
| Satt317 | 89.51 |
| Satt181 | 91.12 |
| P13158A | 96.00 |
| Sat_218 | 99.50 |
| Sat_180 | 104.37 |
| Satt434 | 105.73 |

In other aspects, closely linked markers of the invention can be determined by review of this same genetic map. For example, SSR markers that are closely linked (e.g., separated by not more than 10 cM) to P13158A on linkage group LG-H include:

| Marker | Map Position |
|---|---|
| Satt142 | 86.48 |
| Satt293 | 89.08 |
| Satt317 | 89.51 |
| Satt181 | 91.12 |
| P13158A | 96.00 |
| Sat_218 | 99.50 |
| Sat_180 | 104.37 |
| Satt434 | 105.73 |

Markers that are linked to S63880-CB can be determined from the map provided in FIG. 6. For example, SSR markers on linkage group LG-B1 that are linked to S63880-CB include:

| Marker | Map Position |
|---|---|
| Satt444 | 85.91 |
| Satt665 | 96.36 |
| Sat_123 | 100.87 |
| Satt359 | 102.55 |
| S63880-CB | ~107 |
| Satt484 | 118.52 |
| Satt453 | 123.95 |
| Sat_331 | 125.73 |

In other aspects, closely linked markers of the invention can be determined by review of this same genetic map. For example, SSR markers that are closely linked (e.g., separated by not more than 10 cM) to S63880-CB on linkage group LG-B1 include:

| Marker | Map Position |
| --- | --- |
| Sat_123 | 100.87 |
| Satt359 | 102.55 |
| S63880-CB | ~107 |
| Satt484 | 118.52 |

Markers that are linked to S00415-1-A can be determined from the map provided in FIG. 6. For example, SSR markers on linkage group LG-C1 that are linked to S00799-1-A include:

| Marker | Map Position |
| --- | --- |
| Bng019_1 | 53.86 |
| K472_1 | 53.91 |
| V38a | 54.18 |
| Satt578 | 65.08 |
| Satt607 | 67.02 |
| A519_3 | 69.30 |
| Bng140_1 | 69.68 |
| Satt646 | 70.51 |
| Bng161_1 | 70.57 |
| Dia | 71.08 |
| S00415-1-A | 71.24 |
| L192_1 | 73.16 |
| Satt190 | 73.32 |
| Satt161 | 73.38 |
| Satt718 | 73.79 |
| Sat_404 | 73.84 |
| Satt661 | 74.36 |
| Satt139 | 74.45 |
| AW277661 | 74.79 |
| Satt136 | 75.11 |
| Satt361 | 75.51 |
| Sat_077 | 76.00 |
| Satt399 | 76.23 |
| Sat_416 | 76.41 |
| Sat_357 | 76.43 |
| G214_25 | 76.43 |
| Sat_085 | 76.91 |
| G214_24 | 77.26 |
| Satt294 | 78.65 |
| Sat_322 | 79.26 |
| Satt476 | 80.62 |
| Sat_042 | 82.51 |
| Satt195 | 84.80 |
| Bng143_1 | 85.08 |
| Satt670 | 85.37 |
| Sat_207 | 87.30 |
| Satt713 | 88.94 |
| Sat_311 | 90.11 |
| A063_1 | 90.72 |
| Sct_191 | 92.98 |

In other aspects, closely linked markers of the invention can be determined by review of this same genetic map. For example, SSR markers that are closely linked (e.g., separated by not more than 10 cM) to S00415-1-A on linkage group LG-C1 include:

| Marker | Map Position |
| --- | --- |
| Satt607 | 67.02 |
| A519_3 | 69.30 |
| Bng140_1 | 69.68 |
| Satt646 | 70.51 |
| Bng161_1 | 70.57 |
| Dia | 71.08 |
| S00799-1-A | 71.24 |
| L192_1 | 73.16 |
| Satt190 | 73.32 |
| Satt161 | 73.38 |
| Satt718 | 73.79 |
| Sat_404 | 73.84 |
| Satt661 | 74.36 |
| Satt139 | 74.45 |
| AW277661 | 74.79 |
| Satt136 | 75.11 |
| Satt361 | 75.51 |
| Sat_077 | 76.00 |
| Satt399 | 76.23 |
| Sat_416 | 76.41 |
| Sat_357 | 76.43 |
| G214_25 | 76.43 |
| Sat_085 | 76.91 |
| G214_24 | 77.26 |

Markers that are linked to S00705-1-A can be determined from the map provided in FIG. 6. For example, SSR markers on linkage group LG-D1b that are linked to S00705-1-A include:

| Marker | Map Position |
| --- | --- |
| A605_1 | 64.91 |
| Sat_423 | 67.62 |
| A747_1 | 69.18 |
| Sat_135 | 70.65 |
| Satt412 | 72.57 |
| Satt141 | 72.88 |
| Satt290 | 73.34 |
| Satt611 | 74.01 |
| Satt604 | 74.20 |
| K011_4 | 74.55 |
| Satt506 | 74.79 |
| Satt005 | 75.29 |
| Satt600 | 75.41 |
| L050_3 | 75.44 |
| Satt537 | 75.66 |
| Satt579 | 75.94 |
| Satt282 | 76.09 |
| Sat_089 | 76.27 |
| Satt189 | 76.32 |
| Satt350 | 76.59 |
| Satt428 | 77.34 |
| Mng137_1 | 77.55 |
| Bng047_1 | 77.87 |
| Sat_169 | 78.44 |
| Satt644 | 79.41 |
| S00705-1-A | 83.80 |
| Satt041 | 84.04 |
| RGA_1f | 85.14 |
| Satt546 | 87.19 |
| M7E8mr2 | 87.80 |
| B194_2 | 88.36 |
| Sat_139 | 93.34 |
| Satt703 | 98.75 |
| Satt172 | 100.88 |
| Sat_069 | 102.59 |
| Idh1 | 105.41 |
| A519_2 | 107.61 |

In other aspects, closely linked markers of the invention can be determined by review of this same genetic map. For example, SSR markers that are closely linked (e.g., separated by not more than 10 cM) to S00705-1-A on linkage group LG-D1b include:

| Marker | Map Position |
| --- | --- |
| Satt428 | 77.34 |
| Mng137_1 | 77.55 |
| Bng047_1 | 77.87 |
| Sat_169 | 78.44 |

-continued

| Marker | Map Position |
| --- | --- |
| Satt644 | 79.41 |
| S00705-1-A | 83.80 |
| Satt041 | 84.04 |
| RGA_1f | 85.14 |
| Satt546 | 87.19 |
| M7E8mr2 | 87.80 |
| B194_2 | 88.36 |

Markers that are linked to S02118-1-A can be determined from the map provided in FIG. 6. For example, SSR markers on linkage group LG-N that are linked to S02118-1-A include:

| Marker | Map Position |
| --- | --- |
| Sat_306 | 93.11 |
| Sat_295 | 95.00 |
| Satt022 | 102.05 |
| Sat_125 | 103.33 |
| S02118-1-A | 105.63 |
| A455_2 | 113.48 |
| A363_3 | 116.66 |

In other aspects, closely linked markers of the invention can be determined by review of this same genetic map. For example, SSR markers that are closely linked (e.g., separated by not more than 10 cM) to S02118-1-A on linkage group LG-N include:

| Marker | Map Position |
| --- | --- |
| Satt022 | 102.05 |
| Sat_125 | 103.33 |
| S02118-1-A | 105.63 |
| A455_2 | 113.48 |
| A363_3 | 116.66 |

Similarly, linked markers (including closely linked markers) of the invention can be determined by review of any suitable soybean genetic map. For example, the integrated genetic map described in Song, et al., (2004) also provides a means to identify linked (including closely linked) markers. See, Song, et al., (2004) "A New Integrated Genetic Linkage Map of the Soybean" *Theor Appl Genet* 109:122-128; see also the website for the Soybean Genomics and Improvement Laboratory (SGIL) at the USDA Beltsville Agricultural Research Center (BARC), and see specifically the description of projects in the Cregan Laboratory on that website. That genetic map incorporates a variety of genetic markers that are known in the art or alternatively are described in that reference. Detailed descriptions of numerous markers, including many of those described in Song, et al., (2004) can be found at the SOYBASE website resource.

It is not intended that the determination of linked or closely linked markers be limited to the use of any particular soybean genetic map. Indeed, a large number of soybean genetic maps are available and are well known to one of skill in the art. Another map that finds use with the invention in this respect is the integrated soybean genetic maps found on the SOYBASE website resource. Alternatively still, the determination of linked and closely linked markers can be made by the generation of an experimental dataset and linkage analysis.

It is not intended that the identification of markers that are linked (e.g., within about 50 cM or within about 10 cM) to the Charcoal Rot Drought Complex tolerance QTL markers identified herein be limited to any particular map or methodology. The integrated genetic map provided in FIG. 6 serves only as example for identifying linked markers. Indeed, linked markers as defined herein can be determined from any genetic map known in the art (an experimental map or an integrated map), or alternatively, can be determined from any new mapping dataset.

It is noted that lists of linked and closely linked markers may vary between maps and methodologies due to various factors. First, the markers that are placed on any two maps may not be identical, and furthermore, some maps may have a greater marker density than another map. Also, the mapping populations, methodologies and algorithms used to construct genetic maps can differ. One of skill in the art recognizes that one genetic map is not necessarily more or less accurate than another, and furthermore, recognizes that any soybean genetic map can be used to determine markers that are linked and closely linked to the QTL markers of the present invention.

Techniques for Marker Detection

The invention provides molecular markers that have a significant probability of co-segregation with QTL that impart a Charcoal Rot Drought Complex tolerance phenotype. These QTL markers find use in marker assisted selection for desired traits (tolerance or improved tolerance), and also have other uses. It is not intended that the invention be limited to any particular method for the detection of these markers.

Markers corresponding to genetic polymorphisms between members of a population can be detected by numerous methods well-established in the art (e.g., PCR-based sequence specific amplification, restriction fragment length polymorphisms (RFLPs), isozyme markers, allele specific hybridization (ASH), amplified variable sequences of the plant genome, self-sustained sequence replication, simple sequence repeat (SSR), single nucleotide polymorphism (SNP), random amplified polymorphic DNA ("RAPD") or amplified fragment length polymorphisms (AFLP)). In one additional embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In general, the majority of genetic markers rely on one or more property of nucleic acids for their detection. For example, some techniques for detecting genetic markers utilize hybridization of a probe nucleic acid to nucleic acids corresponding to the genetic marker (e.g., amplified nucleic acids produced using genomic soybean DNA as a template). Hybridization formats, including but not limited to solution phase, solid phase, mixed phase, or in situ hybridization assays are useful for allele detection. An extensive guide to the hybridization of nucleic acids is found in Tijssen (1993) *Laboratory Techniques in Biochemistry and Molecular Biology—Hybridization with Nucleic Acid Probes* Elsevier, New York; Berger and Kimmel, *Guide to Molecular Cloning Techniques, Methods in Enzymology* volume 152 Academic Press, Inc., San Diego, Calif. ("Berger"); as well as in Sambrook and Ausubel (herein).

For example, markers that comprise restriction fragment length polymorphisms (RFLP) are detected, e.g., by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic)

lengths in different individuals or populations. Determining one or more restriction enzyme that produces informative fragments for each cross is a simple procedure, well known in the art. After separation by length in an appropriate matrix (e.g., agarose or polyacrylamide) and transfer to a membrane (e.g., nitrocellulose, nylon, etc.), the labeled probe is hybridized under conditions which result in equilibrium binding of the probe to the target followed by removal of excess probe by washing.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.) (Available on CD ROM).

Amplification-Based Detection Methods

PCR, RT-PCR and LCR are in particularly broad use as amplification and amplification-detection methods for amplifying nucleic acids of interest (e.g., those comprising marker loci), facilitating detection of the markers. Details regarding the use of these and other amplification methods can be found in any of a variety of standard texts, including, e.g., Sambrook, Ausubel, Berger and Croy, herein. Many available biology texts also have extended discussions regarding PCR and related amplification methods. One of skill will appreciate that essentially any RNA can be converted into a double stranded DNA suitable for restriction digestion, PCR expansion and sequencing using reverse transcriptase and a polymerase ("Reverse Transcription-PCR, or "RT-PCR"). See also Ausubel, Sambrook and Berger, above.

Real Time Amplification/Detection Methods

In one aspect, real time PCR or LCR is performed on the amplification mixtures described herein, e.g., using molecular beacons or TaqMan™ probes. A molecular beacon (MB) is an oligonucleotide or PNA which, under appropriate hybridization conditions, self-hybridizes to form a stem and loop structure. The MB has a label and a quencher at the termini of the oligonucleotide or PNA; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, e.g., to a region of an amplicon during amplification), the MB label is unquenched. Details regarding standard methods of making and using MBs are well established in the literature and MBs are available from a number of commercial reagent sources. See also, e.g., Leone, et al., (1995) "Molecular beacon probes combined with amplification by NASBA enable homogenous real-time detection of RNA" *Nucleic Acids Res* 26:2150-2155; Tyagi and Kramer, (1996) "Molecular beacons: probes that fluoresce upon hybridization" *Nature Biotechnology* 14:303-308; Blok and Kramer, (1997) "Amplifiable hybridization probes containing a molecular switch" *Mol Cell Probes* 11:187-194; Hsuih, et al., (1997) "Novel, ligation-dependent PCR assay for detection of hepatitis C in serum" *J Clin Microbiol* 34:501-507; Kostrikis, et al., (1998) "Molecular beacons: spectral genotyping of human alleles" *Science* 279:1228-1229; Sokol, et al., (1998) "Real time detection of DNA:RNA hybridization in living cells" *Proc Natl Acad Sci USA* 95:11538-11543; Tyagi, et al., (1998) "Multicolor molecular beacons for allele discrimination" *Nature Biotechnology* 16:49-53; Bonnet, et al., (1999) "Thermodynamic basis of the chemical specificity of structured DNA probes" *Proc Natl Acad Sci USA* 96:6171-6176; Fang, et al., (1999) "Designing a novel molecular beacon for surface-immobilized DNA hybridization studies" *J Am Chem Soc* 121:2921-2922; Marras, et al., (1999) "Multiplex detection of single-nucleotide variation using molecular beacons" *Genet Anal Biomol Eng* 14:151-156; and Vet, et al., (1999) "Multiplex detection of four pathogenic retroviruses using molecular beacons" *Proc Natl Acad Sci USA* 96:6394-6399. Additional details regarding MB construction and use is found in the patent literature, e.g., U.S. Pat. No. 5,925,517 (Jul. 20, 1999) to Tyagi, et al., entitled "Detectably labeled dual conformation oligonucleotide probes, assays and kits;" U.S. Pat. No. 6,150,097 (Nov. 21, 2000) to Tyagi, et al., entitled "Nucleic acid detection probes having non-FRET fluorescence quenching and kits and assays including such probes" and U.S. Pat. No. 6,037,130 (Mar. 14, 2000) to Tyagi, et al., entitled "Wavelength-shifting probes and primers and their use in assays and kits."

PCR detection and quantification using dual-labeled fluorogenic oligonucleotide probes, commonly referred to as "TagMan™" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. Accordingly, TagMan™ probes are oligonucleotides that have a label and a quencher, where the label is released during amplification by the exonuclease action of the polymerase used in amplification. This provides a real time measure of amplification during synthesis. A variety of TagMan™ reagents are commercially available, e.g., from Applied Biosystems (Division Headquarters in Foster City, Calif.) as well as from a variety of specialty vendors such as Biosearch Technologies (e.g., black hole quencher probes).

Additional Details Regarding Amplified Variable Sequences, SSR, AFLP ASH, SNPs and Isozyme Markers Amplified variable sequences refer to amplified sequences of the plant genome which exhibit high nucleic acid residue variability between members of the same species. All organisms have variable genomic sequences and each organism (with the exception of a clone) has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNase H, and (3) a DNA-dependent RNA polymerase (Guatelli, et al., (1990) *Proc Natl Acad Sci USA* 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos, et al., (1995) *Nucleic Acids Res* 23:4407). The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker, et al., (1995) *Mol Gen Genet* 249:65; and Meksem, et al., (1995) *Mol Gen Genet* 249:74).

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, the ASH probe sequence may be bound to a membrane.

In one embodiment, ASH data are typically obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are also appropriate.

Isozyme markers can be employed as genetic markers, e.g., to track markers other than the tolerance markers herein, or to track isozyme markers linked to the markers herein. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

Additional Details Regarding Nucleic Acid Amplification

As noted, nucleic acid amplification techniques such as PCR and LCR are well known in the art and can be applied to the present invention to amplify and/or detect nucleic acids of interest, such as nucleic acids comprising marker loci. Examples of techniques sufficient to direct persons of skill through such in vitro methods, including the polymerase chain reaction (PCR), the ligase chain reaction (LCR), Qββ-replicase amplification and other RNA polymerase mediated techniques (e.g., NASBA), are found in the references noted above, e.g., Innis, Sambrook, Ausubel, Berger and Croy. Additional details are found in Mullis, et al., (1987) U.S. Pat. No. 4,683,202; Arnheim and Levinson, (Oct. 1, 1990) C&EN 36-47; The Journal Of NIH Research (1991) 3:81-94; Kwoh, et al., (1989) *Proc Natl Acad Sci USA* 86:1173; Guatelli, et al., (1990) *Proc Natl Acad Sci USA* 87:1874; Lomeli, et al., (1989) *J Clin Chem* 35:1826; Landegren, et al., (1988) *Science* 241:1077-1080; Van Brunt, (1990) *Biotechnology* 8:291-294; Wu and Wallace, (1989) *Gene* 4:560; Barringer, et al., (1990) *Gene* 89:117, and Sooknanan and Malek, (1995) *Biotechnology* 13:563-564. Improved methods of amplifying large nucleic acids by PCR, which is useful in the context of positional cloning, are further summarized in Cheng, et al., (1994) *Nature* 369:684, and the references therein, in which PCR amplicons of up to 40 kb are generated.

Probe/Primer Synthesis Methods

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described by Beaucage and Caruthers, (1981) *Tetrahedron Letts* 22(20): 1859-1862, e.g., using a commercially available automated synthesizer, e.g., as described in Needham-VanDevanter, et al., (1984) *Nucleic Acids Res* 12:6159-6168. Oligonucleotides, including modified oligonucleotides can also be ordered from a variety of commercial sources known to persons of skill. There are many commercial providers of oligo synthesis services, and thus this is a broadly accessible technology. Any nucleic acid can be custom ordered from any of a variety of commercial sources, such as The Midland Certified Reagent Company, The Great American Gene Company, ExpressGen Inc., Operon Technologies Inc. (Alameda, Calif.) and many others. Similarly, PNAs can be custom ordered from any of a variety of sources, such as PeptidoGenic, HTI Bio-Products, Inc., BMA Biomedicals Ltd (U.K.), Bio•Synthesis, Inc., and many others.

In Silico Marker Detection

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST, or even simple word processors.

Amplification Primers for Marker Detection

In some preferred embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers".

It will be appreciated that, although many specific examples of primers are provided herein (see, FIG. 2), suitable primers to be used with the invention can be designed using any suitable method. It is not intended that the invention be limited to any particular primer or primer pair. For example, primers can be designed using any suitable software program, such as LASERGENE®.

In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons.

It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those given in the allele definitions in FIG. 4. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited in FIG. 4 also find use with the present invention.

Marker Assisted Selection and Breeding of Plants

A primary motivation for development of molecular markers in crop species is the potential for increased efficiency in plant breeding through marker assisted selection (MAS). Genetic markers are used to identify plants that contain a desired genotype at one or more loci, and that are expected to transfer the desired genotype, along with a desired phenotype to their progeny. Genetic markers can be used to identify plants that contain a desired genotype at one locus, or at several unlinked or linked loci (e.g., a haplotype), and that would be expected to transfer the desired genotype, along with a desired phenotype to their progeny. The present invention provides the means to identify plants, particularly soybean plants, that are tolerant, exhibit improved tolerance or are susceptible to Charcoal Rot Drought Complex by identifying plants having a specified allele at one of those loci, e.g., Sct_028, Satt512, S60211-TB, Sat_117, P13158A, S63880-CB, S00415-1-A, S00705-1-A, and S02118-1-A.

Similarly, by identifying plants lacking the desired marker locus, susceptible or less tolerant plants can be identified, and, e.g., eliminated from subsequent crosses. Similarly, these marker loci can be introgressed into any desired genomic background, germplasm, plant, line, variety, etc., as part of an overall MAS breeding program designed to enhance soybean yield.

The invention also provides chromosome QTL intervals that find equal use in MAS to select plants that demonstrate Charcoal Rot Drought Complex tolerance or improved tolerance. Similarly, the QTL intervals can also be used to counter-select plants that are susceptible or have reduced tolerance to Charcoal Rot Drought Complex. Any marker that maps within the QTL interval (including the termini of the intervals) finds use with the invention. These intervals are defined by the following pairs of markers:

(i) Satt286 and Satt371 (LG-C2);
(ii) Satt575 and Sat_136 (LG-E);
(iii) Satt467 and Satt416 (LG-B2);
(iv) Satt612 and A681_1 (LG-G);
(v) Sat_158 and A162_1 (LG-H);
(vi) Satt444 and Sat_331 (LG-B1);
(vii) Bng019_1 and Sct_191 (LG-C1);
(viii) A605_1 and A519_2 (LG-D1b); and,
(xi) Sat_306 and A363_3 (LG-N).

In general, MAS uses polymorphic markers that have been identified as having a significant likelihood of co-segregation with a tolerance trait. Such markers are presumed to map near a gene or genes that give the plant its tolerance phenotype, and are considered indicators for the desired trait, and are termed QTL markers. Plants are tested for the presence of a desired allele in the QTL marker. The most preferred markers (or marker alleles) are those that have the strongest association with the tolerance trait.

Linkage analysis is used to determine which polymorphic marker allele demonstrates a statistical likelihood of co-segregation with the tolerance phenotype (thus, a "tolerance marker allele"). Following identification of a marker allele for co-segregation with the tolerance phenotype, it is possible to use this marker for rapid, accurate screening of plant lines for the tolerance allele without the need to grow the plants through their life cycle and await phenotypic evaluations, and furthermore, permits genetic selection for the particular tolerance allele even when the molecular identity of the actual tolerance QTL is unknown. Tissue samples can be taken, for example, from the first leaf of the plant and screened with the appropriate molecular marker, and it is rapidly determined which progeny will advance. Linked markers also remove the impact of environmental factors that can often influence phenotypic expression.

A polymorphic QTL marker locus can be used to select plants that contain the marker allele (or alleles) that correlate with the desired tolerance phenotype. In brief, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, or the like. A variety of procedures for detecting markers are described herein, e.g., in the section entitled "TECHNIQUES FOR MARKER DETECTION." After the presence (or absence) of a particular marker allele in the biological sample is verified, the plant is selected, e.g., used to make progeny plants by selective breeding.

Soybean plant breeders desire combinations of tolerance loci with genes for high yield and other desirable traits to develop improved soybean varieties. Screening large numbers of samples by non-molecular methods (e.g., trait evaluation in soybean plants) can be expensive, time consuming, and unreliable. Use of the polymorphic markers described herein, when genetically-linked to tolerance loci, provide an effective method for selecting resistant varieties in breeding programs. For example, one advantage of marker-assisted selection over field evaluations for tolerance resistance is that MAS can be done at any time of year, regardless of the growing season. Moreover, environmental effects are largely irrelevant to marker-assisted selection.

When a population is segregating for multiple loci affecting one or multiple traits, e.g., multiple loci involved in tolerance, or multiple loci each involved in tolerance or resistance to different diseases, the efficiency of MAS compared to phenotypic screening becomes even greater, because all of the loci can be evaluated in the lab together from a single sample of DNA. In the present instance, the Sct__028, Satt512, S60211-TB, Sat__117, P13158A, S63880-CB, S00415-1-A, S00705-1-A, and S02118-1-A markers, as well as any of the chromosome intervals
  (i) Satt286 and Satt371 (LG-C2);
  (ii) Satt575 and Sat__136 (LG-E);
  (iii) Satt467 and Satt416 (LG-B2);
  (iv) Satt612 and A681__1 (LG-G);
  (v) Sat__158 and A162__1 (LG-H);
  (vi) Satt444 and Sat__331 (LG-B1);
  (vii) Bng019__1 and Sct__191 (LG-C1);
  (viii) A605__1 and A519__2 (LG-D1b); and,
  (xi) Sat__306 and A363__3 (LG-N).
can be assayed simultaneously or sequentially from a single sample or a population of samples.

Another use of MAS in plant breeding is to assist the recovery of the recurrent parent genotype by backcross breeding. Backcross breeding is the process of crossing a progeny back to one of its parents or parent lines. Backcrossing is usually done for the purpose of introgressing one or a few loci from a donor parent (e.g., a parent comprising desirable tolerance marker loci) into an otherwise desirable genetic background from the recurrent parent (e.g., an otherwise high yielding soybean line). The more cycles of backcrossing that are done, the greater the genetic contribution of the recurrent parent to the resulting introgressed variety. This is often necessary, because tolerant plants may be otherwise undesirable, e.g., due to low yield, low fecundity, or the like. In contrast, strains which are the result of intensive breeding programs may have excellent yield, fecundity or the like, merely being deficient in one desired trait such as tolerance to Charcoal Rot Drought Complex.

The presence and/or absence of a particular genetic marker or allele, e.g., Sct__028, Satt512, S60211-TB, Sat__117, P13158A, S63880-CB, S00415-1-A, S00705-1-A, and S02118-1-A markers, as well as any of the chromosome intervals
  (i) Satt286 and Satt371 (LG-C2);
  (ii) Satt575 and Sat__136 (LG-E);
  (iii) Satt467 and Satt416 (LG-B2);
  (iv) Satt612 and A681__1 (LG-G);
  (v) Sat__158 and A162__1 (LG-H);
  (vi) Satt444 and Sat__331 (LG-B1);
  (vii) Bng019__1 and Sct__191 (LG-C1);
  (viii) A605__1 and A519__2 (LG-D1b); and,
  (xi) Sat__306 and A363__3 (LG-N)
in the genome of a plant is made by any method noted herein. If the nucleic acids from the plant are positive for a desired genetic marker allele, the plant can be self fertilized to create a true breeding line with the same genotype, or it can be crossed with a plant with the same marker or with other desired characteristics to create a sexually crossed hybrid generation.

Introgression of Favorable Alleles—Efficient Backcrossing of Tolerance Markers into Elite Lines One application of MAS, in the context of the present invention is to use the tolerance or improved tolerance markers to increase the efficiency of an introgression or backcrossing effort aimed at introducing a tolerance QTL into a desired (typically high yielding) background. In marker assisted backcrossing of specific markers (and associated QTL) from a donor source, e.g., to an elite or exotic genetic background, one selects among backcross progeny for the donor trait and then uses repeated backcrossing to the elite or exotic line to reconstitute as much of the elite/exotic background's genome as possible.

Thus, the markers and methods of the present invention can be utilized to guide marker assisted selection or breeding of soybean varieties with the desired complement (set) of allelic forms of chromosome segments associated with superior agronomic performance (tolerance, along with any other available markers for yield, disease resistance, etc.). Any of the disclosed marker alleles can be introduced into a soybean line via introgression, by traditional breeding (or introduced via transformation, or both) to yield a soybean plant with superior agronomic performance. The number of alleles associated with tolerance that can be introduced or be present in a soybean plant of the present invention ranges from 1 to the number of alleles disclosed herein, each integer of which is incorporated herein as if explicitly recited.

The present invention also extends to a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with tolerance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant of the present invention in that it comprises at least one of the allelic forms of the markers of the present invention, such that the progeny are capable of inheriting the allele.

Often, a method of the present invention is applied to at least one related soybean plant such as from progenitor or descendant lines in the subject soybean plant's pedigree such that inheritance of the desired tolerance allele can be traced. The number of generations separating the soybean plants being subject to the methods of the present invention will generally be from 1 to 20, commonly 1 to 5, and typically 1, 2 or 3 generations of separation, and quite often a direct descendant or parent of the soybean plant will be subject to the method (i.e., one generation of separation).

Introgression of Favorable Alleles—Incorporation of "Exotic" Germplasm while Maintaining Breeding Progress Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite×exotic soybean lines by subjecting the segregating progeny to MAS to maintain major yield alleles, along with the tolerance marker alleles herein.

Generation of Transgenic Cells and Plants

The present invention also relates to host cells and organisms which are transformed with nucleic acids corresponding to tolerance QTL identified according to the invention. For example, such nucleic acids include chromosome intervals (e.g., genomic fragments) that encode a tolerance or improved tolerance trait.

General texts which describe molecular biological techniques for the cloning and manipulation of nucleic acids and production of encoded polypeptides include Berger, Sambrook, and Ausubel, herein. These texts describe mutagenesis, the use of vectors, promoters and many other relevant topics related to, e.g., the generation of clones that comprise nucleic acids of interest, e.g., marker loci, marker probes, QTL that segregate with marker loci, etc.

Host cells are genetically engineered (e.g., transduced, transfected, transformed, etc.) with the vectors of this invention which can be, for example, a cloning vector, a shuttle vector or an expression vector. Such vectors are, for example, in the form of a plasmid, a phagemid, an *agrobacterium*, a virus, a naked polynucleotide (linear or circular), or a conjugated polynucleotide. Vectors can be introduced into bacteria, especially for the purpose of propagation and expansion. The vectors are also introduced into plant tissues, cultured plant cells or plant protoplasts by a variety of standard methods known in the art, including but not limited to electroporation (Fromm, et al., (1985) *Proc Natl Acad Sci USA* 82:5824), infection by viral vectors such as cauliflower mosaic virus (CaMV) (Hohn, et al., (1982) *Molecular Biology of Plant Tumors* Academic Press, New York, pp. 549-560; Howell, U.S. Pat. No. 4,407,956), high velocity ballistic penetration by small particles with the nucleic acid either within the matrix of small beads or particles, or on the surface (Klein, et al., (1987) *Nature* 327:70), use of pollen as vector (WO85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch, et al., (1984) *Science* 233:496; Fraley, et al., (1983) *Proc Natl Acad Sci USA* 80:4803). Additional details regarding nucleic acid introduction methods are found in Sambrook, Berger and Ausubel, supra. The method of introducing a nucleic acid of the present invention into a host cell is not critical to the instant invention, and it is not intended that the invention be limited to any particular method for introducing exogenous genetic material into a host cell. Thus, any suitable method, e.g., including but not limited to the methods provided herein, which provides for effective introduction of a nucleic acid into a cell or protoplast can be employed and finds use with the invention.

The engineered host cells can be cultured in conventional nutrient media modified as appropriate for such activities as, for example, activating promoters or selecting transformants. These cells can optionally be cultured into transgenic plants. In addition to Sambrook, Berger and Ausubel, supra, plant regeneration from cultured protoplasts is described in Evans, et al., (1983) "Protoplast Isolation and Culture," *Handbook of Plant Cell Cultures* 1:124-176 (MacMillan Publishing Co., New York; Davey, (1983) "Recent Developments in the Culture and Regeneration of Plant Protoplasts," *Protoplasts*, pp. 12-29, (Birkhauser, Basel); Dale, (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton, Fla.). Additional details regarding plant cell culture and regeneration include Payne, et al., (1992) *Plant Cell and Tissue Culture in Liquid Systems* John Wiley & Sons, Inc. New York, N.Y.; Gamborg and Phillips, (eds) (1995) *Plant Cell, Tissue and Organ Culture; Fundamental Methods* Springer Lab Manual, Springer-Verlag (Berlin Heidelberg New York) and *Plant Molecular Biology* (1993) Croy, Ed. Bios Scientific Publishers, Oxford, U.K. ISBN 0 12 198370 6. Cell culture media in general are also set forth in Atlas and Parks, (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., *the Plant Culture Catalogue* and supplement (e.g., 1997 or later) also from Sigma-Aldrich, Inc (St Louis, Mo.) ("Sigma-PCCS").

The present invention also relates to the production of transgenic organisms, which may be bacteria, yeast, fungi, animals or plants, transduced with the nucleic acids of the invention (e.g., nucleic acids comprising the marker loci and/or QTL noted herein). A thorough discussion of techniques relevant to bacteria, unicellular eukaryotes and cell culture is found in references enumerated herein and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAprep™ from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman and Smith, (1979) *Gene* 8:81; Roberts, et al., (1987) *Nature* 328: 731; Schneider, et al., (1995) *Protein Expr Purif* 6435:10; Ausubel, Sambrook, Berger (all supra). A catalogue of Bacteria and Bacteriophages useful for cloning is provided, e.g., by the ATCC, e.g., *The ATCC Catalogue of Bacteria and Bacteriophaqe* (1992) Gherna, et al., (eds) published by the ATCC. Additional basic procedures for sequencing, cloning and other aspects of molecular biology and underlying theoretical considerations are also found in Watson, et al., (1992) *Recombinant DNA*, Second Edition, Scientific American Books, NY. In addition, essentially any nucleic acid (and virtually any labeled nucleic acid, whether standard or nonstandard) can be custom or standard ordered from any of a variety of commercial sources, such as the Midland Certified Reagent Company (Midland, Tex.), The Great American Gene Company (Ramona, Calif.), ExpressGen Inc. (Chicago, Ill.), Operon Technologies Inc. (Alameda, Calif.) and many others.

Introducing Nucleic Acids into Plants.

Techniques for transforming plant cells with nucleic acids are widely available and can be readily adapted to the invention. In addition to Berger, Ausubel and Sambrook, all supra, useful general references for plant cell cloning, culture and regeneration include Jones, (ed) (1995) *Plant Gene Transfer and Expression Protocols—Methods in Molecular Biology*, Volume 49 Humana Press Towata N.J.; Payne, et al., (1992) *Plant Cell and Tissue Culture in Liquid Systems* John Wiley & Sons, Inc. New York, N.Y. (Payne); and Gamborg and Phillips, (eds) (1995) *Plant Cell, Tissue and Organ Culture; Fundamental Methods* Springer Lab Manual, Springer-Verlag (Berlin Heidelberg New York) (Gamborg). A variety of cell culture media are described in Atlas and Parks, (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St Louis, Mo.) (Sigma-PCCS). Additional details regarding plant cell culture are found in Croy, (ed.) (1993) *Plant Molecular Biology*, Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Techniques for transforming a wide variety of higher plant species are also well known and described in widely available technical, scientific, and patent literature. See, for example, Weissinger, et al., (1988) *Ann Rev Genet* 22:421-477. The DNA constructs of the invention, for example plasmids, phagemids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting plant, e.g., cells, embryos, callus and protoplasts, are known in the art and well described in the scientific and patent literature. For example, a number of methods are described in Jones, (ed) (1995) *Plant Gene Transfer and Expression Protocols—Methods in Molecular Biology*, Volume 49 Humana Press, Towata, N.J., as well as in the other references noted herein and available in the literature.

For example, the introduction of DNA constructs using polyethylene glycol precipitation is described in Paszkowski, et al., (1984) *EMBO J* 3:2717. Electroporation techniques are described in Fromm, et al., (1985) *Proc Natl Acad Sci USA* 82:5824. Ballistic transformation techniques are described in Klein, et al., (1987) *Nature* 327:70-73. Additional details are found in Jones, (1995) and Gamborg and Phillips, (1995), supra, and in U.S. Pat. No. 5,990,387.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example, Horsch, et al., (1984) *Science* 233:496; and Fraley, et al., (1984) *Proc Natl Acad Sci USA* 80:4803 and recently reviewed in Hansen and Chilton, (1998) *Current Topics in Microbiology* 240:22; and Das, (1998) *Subcellular Biochemistry* 29: *Plant Microbe Interactions*, pp 343-363.

DNA constructs are optionally combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller, (1987) In: *Genetic Engineering*, vol. 6, PWJ Rigby, Ed., London, Academic Press; and Lichtenstein and Draper (1985) In: *DNA Cloning*, Vol. II, Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman, et al., (1984) *Plant Cell Physiol* 25:1353), (3) the vortexing method (see, e.g., Kindle, (1990) *Proc Natl Acad Sci USA* 87:1228.

DNA can also be introduced into plants by direct DNA transfer into pollen as described by Zhou, et al., (1983) *Methods in Enzymology* 101:433; Hess, (1987) *Intern Rev Cytol* 107:367; Luo, et al., (1988) *Plant Mol Biol Rep* 6:165. Expression of polypeptide coding genes can be obtained by injection of the DNA into reproductive organs of a plant as described by Pena, et al., (1987) *Nature* 325:274. DNA can also be injected directly into the cells of immature embryos and the desiccated embryos rehydrated as described by Neuhaus, et al., (1987) *Theor Appl Genet* 75:30; and Benbrook, et al., (1986) in *Proceedings Bio Expo* Butterworth, Stoneham, Mass., pp. 27-54. A variety of plant viruses that can be employed as vectors are known in the art and include cauliflower mosaic virus (CaMV), geminivirus, brome mosaic virus, and tobacco mosaic virus.

Generation/Reqeneration of Transqenic Plants

Transformed plant cells which are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Payne, et al., (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Evans, et al., (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton. Regeneration can also be obtained from plant callus., explants, somatic embryos (Dandekar, et al., (1989) *J Tissue Cult Meth* 12:145; McGranahan, et al., (1990) *Plant Cell Rep* 8:512) organs, or parts thereof. Such regeneration techniques are described generally in Klee, et al., (1987) *Ann Rev Plant Phys* 38:467-486. Additional details are found in Payne, (1992) and Jones (1995), both supra, and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTLs according to the methods of the invention.

In addition, the regeneration of plants containing nucleic acids of the present invention and introduced by *Agrobacterium* into cells of leaf explants can be achieved as described by Horsch, et al., (1985) *Science* 227:1229-1231. In this procedure, transformants are grown in the presence of a selection agent and in a medium that induces the regeneration of shoots in the plant species being transformed as described by Fraley, et al., (1983) *Proc Natl Acad Sci USA* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

It is not intended that plant transformation and expression of polypeptides that provide disease tolerance, as provided by the present invention, be limited to soybean species. Indeed, it is contemplated that the polypeptides that provide the desired tolerance in soybean can also provide such tolerance when transformed and expressed in other agronomically and horticulturally important species. Such species include primarily dicots, e.g., of the families: Leguminosae (including pea, beans, lentil, peanut, yam bean, cowpeas, velvet beans, soybean, clover, alfalfa, lupine, vetch, lotus, sweet clover, wisteria and sweetpea); and Compositae (the largest family of vascular plants, including at least 1,000 genera, including important commercial crops such as sunflower).

Additionally, preferred targets for modification with the nucleic acids of the invention, as well as those specified above, plants from the genera: *Allium, Apium, Arachis, Brassica, Capsicum, Cicer, Cucumis, Curcubita, Daucus, Fagopyrum, Glycine, Helianthus, Lactuca, Lens, Lycopersicon, Medicago, Pisum, Phaseolus, Solanum, Trifolium, Vigna* and many others.

Common crop plants which are targets of the present invention include soybean, sunflower, canola, peas, beans, lentils, peanuts, yam beans, cowpeas, velvet beans, clover, alfalfa, lupine, vetch, sweet clover, sweetpea, field pea, fava bean, broccoli, brussel sprouts, cabbage, cauliflower, kale, kohlrabi, celery, lettuce, carrot, onion, pepper, potato, eggplant and tomato.

In construction of recombinant expression cassettes of the invention, which include, for example, helper plasmids comprising virulence functions, and plasmids or viruses comprising exogenous DNA sequences such as structural genes, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill. Alternatively, the plant promoter may direct expression of nucleic acids of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds or flowers.

Any of a number of promoters which direct transcription in plant cells can be suitable. The promoter can be either constitutive or inducible. In addition to the promoters noted above, promoters of bacterial origin that operate in plants include the octopine synthase promoter, the nopaline synthase promoter and other promoters derived from native Ti plasmids. See, Herrara-Estrella, et al., (1983) *Nature* 303:209. Viral promoters include the 35S and 19S RNA promoters of cauliflower mosaic virus. See, Odell, et al., (1985) *Nature* 313:810. Other plant promoters include Kunitz trypsin inhibitor promoter (KTI), SCP1, SUP, UCD3, the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J* 7:3315. Many other promoters are in current use and can be coupled to an exogenous DNA sequence to direct expression.

If expression of a polypeptide from a cDNA is desired, a polyadenylation region at the 3'-end of the coding region is typically included. The polyadenylation region can be derived from the natural gene, from a variety of other plant genes, or from, e.g., T-DNA.

A vector comprising sequences of the invention will typically include a nucleic acid subsequence, a marker gene which confers a selectable, or alternatively, a screenable, phenotype on plant cells. For example, the marker can encode biocide tolerance, particularly antibiotic tolerance, such as tolerance to kanamycin, G418, bleomycin, hygromycin, or herbicide tolerance, such as tolerance to chlorosulforon, or phosphinothricin (the active ingredient in the herbicides bialaphos or Basta). See, e.g., Padgette, et al., (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops that encode appropriate herbicide metabolizing enzymes from other organisms, such as microbes. See, Vasil, (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic or introgressed plants comprising nucleic acids of the present invention can be screened for transmission of the nucleic acid of the present invention by, for example, standard nucleic acid detection methods or by immunoblot protocols.

A preferred embodiment of the invention is a transgenic plant that is homozygous for the added heterologous nucleic acid; e.g., a transgenic plant that contains two added nucleic acid sequence copies. A homozygous transgenic plant can be obtained by sexually mating (self-fertilizing) a heterozygous transgenic plant that contains a single added heterologous nucleic acid. Back-crossing to a parental plant and out-crossing with a non-transgenic plant can be used to introgress the heterologous nucleic acid into a selected background (e.g., an elite or exotic soybean line).

Methods for Charcoal Rot Drought Complex Tolerant Soybean Plants

Experienced plant breeders can recognize tolerant soybean plants in the field, and can select the tolerant individuals or populations for breeding purposes or for propagation. In this context, the plant breeder recognizes "tolerant" and "non-tolerant" or "susceptible", soybean plants.

Such plant breeding practitioners will appreciate that plant tolerance is a phenotypic spectrum consisting of extremes in tolerance, susceptibility and a continuum of intermediate tolerance phenotypes. Tolerance also varies due to environmental effects and the severity of pathogen infection. Evaluation of phenotypes using reproducible assays and tolerance scoring methods are of value to scientists who seek to identify genetic loci that impart tolerance, conduct marker assisted selection for tolerant populations, and for introgression techniques to breed a tolerance trait into an elite soybean line, for example.

In contrast to fortuitous field observations that classify plants as either "tolerant" or "susceptible", various systems are known for scoring the degree of plant tolerance or susceptibility. These techniques can be applied to different fields at different times, and provide approximate tolerance scores that can be used to characterize a given strain regardless of growth conditions or location.

Ratings are assigned by evaluating all plants of a cultivar in a 2 row by 15 foot plot. Cultivar scores are based on a 1 to 9 system where a score of 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death. FIG. 8 gives a representative example of cultivars with vastly different Charcoal Rot Drought Complex tolerance using this scoring system.

Automated Detection/Correlation Systems of the Invention

In some embodiments, the present invention includes an automated system for detecting markers of the invention and/or correlating the markers with a desired phenotype (e.g., tolerance). Thus, a typical system can include a set of marker probes or primers configured to detect at least one favorable allele of one or more marker locus associated with tolerance or improved tolerance to Charcoal Rot Drought Complex. These probes or primers are configured to detect the marker alleles noted in the tables and examples herein, e.g., using any available allele detection format, e.g., solid or liquid phase array based detection, microfluidic-based sample detection, etc.

For example, in one embodiment, the marker locus is Sct_028, Satt512, S60211-TB, Sat_117, P13158A, S63880-CB, S00415-1-A, S00705-1-A, and S02118-1-A, or any combination thereof, as well as any of the chromosome intervals (i) Satt286 and Satt371 (LG-C2);
(ii) Satt575 and Sat_136 (LG-E);
(iii) Satt467 and Satt416 (LG-B2);
(iv) Satt612 and A681_1 (LG-G);
(v) Sat_158 and A162_1 (LG-H);
(vi) Satt444 and Sat_331 (LG-B1);
(vii) Bng019_1 and Sct_191 (LG-C1);
(viii) A605_1 and A519_2 (LG-D1b); and,
(xi) Sat_306 and A363_3 (LG-N) or any combination thereof, and the probe set is configured to detect the locus.

The typical system includes a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, arrays and array scanners, scanning detectors, phototubes and photodiodes, microscope stations, galvo-scanns, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector embodiments include light (e.g., fluorescence) detectors or radioactivity detectors. For example, detection of a light emission (e.g., a fluorescence emission) or other probe label is indicative of the presence or absence of a marker allele. Fluorescent detection is especially preferred and is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele.

The detector(s) optionally monitors one or a plurality of signals from an amplification reaction. For example, the detector can monitor optical signals which correspond to "real time" amplification assay results.

System instructions that correlate the presence or absence of the favorable allele with the predicted tolerance are also a feature of the invention. For example, the instructions can include at least one look-up table that includes a correlation between the presence or absence of the favorable alleles and the predicted tolerance or improved tolerance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical embodiment, the system instructions include at least one look-up table that includes a correlation between the presence or absence of the favorable alleles and predicted tolerance or improved tolerance. The instructions also typically include instructions providing a user interface with the system, e.g., to permit a user to view results of a sample analysis and to input parameters into the system.

The system typically includes components for storing or transmitting computer readable data representing or designating the alleles detected by the methods of the present invention, e.g., in an automated system. The computer readable media can include cache, main, and storage memory and/or other electronic data storage components (hard drives, floppy drives, storage drives, etc.) for storage of computer code. Data representing alleles detected by the method of the present invention can also be electronically, optically, or magnetically transmitted in a computer data signal embodied in a transmission medium over a network such as an intranet or internet or combinations thereof. The system can also or alternatively transmit data via wireless, IR, or other available transmission alternatives.

During operation, the system typically comprises a sample that is to be analyzed, such as a plant tissue, or material isolated from the tissue such as genomic DNA, amplified genomic DNA, cDNA, amplified cDNA, RNA, amplified RNA, or the like.

The phrase "allele detection/correlation system" in the context of this invention refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program", by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or SigmaPlot) for charting or creating look up tables of relevant allele-trait correlations. Other useful software tools in the context of the integrated systems of the invention include statistical packages such as SAS, Genstat, Matlab, Mathematica, and S-Plus and genetic modeling packages such as QU-GENE. Furthermore, additional programming languages such as visual basic are also suitably employed in the integrated systems of the invention.

For example, tolerance marker allele values assigned to a population of progeny descending from crosses between elite lines are recorded in a computer readable medium, thereby establishing a database corresponding tolerance alleles with unique identifiers for members of the population of progeny. Any file or folder, whether custom-made or commercially available (e.g., from Oracle or Sybase) suitable for recording data in a computer readable medium is acceptable as a database in the context of the present invention. Data regarding genotype for one or more molecular markers, e.g., ASH, SSR, RFLP, RAPD, AFLP, SNP, isozyme markers or other markers as described herein, are similarly recorded in a computer accessible database. Optionally, marker data is obtained using an integrated system that automates one or more aspects of the assay(s) used to determine marker(s) genotype. In such a system, input data corresponding to genotypes for molecular markers are relayed from a detector, e.g., an array, a scanner, a CCD, or other detection device directly to files in a computer readable medium accessible to the central processing unit. A set of system instructions (typically embodied in one or more programs) encoding the correlations between tolerance and the alleles of the invention is then executed by the computational device to identify correlations between marker alleles and predicted trait phenotypes.

Typically, the system also includes a user input device, such as a keyboard, a mouse, a touchscreen, or the like (for, e.g., selecting files, retrieving data, reviewing tables of maker information), and an output device (e.g., a monitor, a printer) for viewing or recovering the product of the statistical analysis.

Thus, in one aspect, the invention provides an integrated system comprising a computer or computer readable medium comprising a set of files and/or a database with at least one data set that corresponds to the marker alleles herein. The system also includes a user interface allowing a user to selectively view one or more of these databases. In addition, standard text manipulation software such as word processing software (e.g., Microsoft Word™ or Corel WordPerfect™) and database or spreadsheet software (e.g., spreadsheet software such as Microsoft Excel™, Corel Quattro Pro™, or database programs such as Microsoft Access™ or Paradox™) can be used in conjunction with a user interface (e.g., a GUI in a standard operating system such as a Windows, Macintosh, Unix or Linux system) to manipulate strings of characters corresponding to the alleles or other features of the database.

The systems optionally include components for sample manipulation, e.g., incorporating robotic devices. For example, a robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system. Many such automated robotic fluid handling systems are commercially available. For example, a variety of automated systems are available from Caliper Technologies (Hopkinton, Mass.), which utilize various Zymate systems, which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). As an alternative to conventional robotics, microfluidic systems for performing fluid handling and detection are now widely available, e.g., from Caliper Technologies Corp. (Hopkinton, Mass.) and Agilent Technologies (Palo Alto, Calif.).

Systems for molecular marker analysis of the present invention can, thus, include a digital computer with one or more of high-throughput liquid control software, image analysis software for analyzing data from marker labels, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to markers on a solid support operably linked to the digital computer. The image scanner interfaces with the image analysis software to provide a measurement of, e.g., nucleic acid probe label intensity upon hybridization to an arrayed sample nucleic acid population (e.g., comprising one or more markers), where the probe label intensity measurement is interpreted by the data interpretation software to show whether, and to what degree, the labeled probe hybridizes to a marker nucleic acid (e.g., an amplified marker allele). The data so derived is then correlated with sample identity, to determine the identity of a plant with a particular genotype(s) for particular markers or alleles, e.g., to facilitate marker assisted selection of soybean plants with favorable allelic forms of chromosome segments involved in agronomic performance (e.g., tolerance or improved tolerance).

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (Intel x86 or Pentium chip-compatible DOS™, OS2™ WINDOWS™, WINDOWS NT™ or WINDOWS 95™ based machines), MACINTOSH™, LINUX, or UNIX based (e.g., SUN™ work station) computers.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Intergroup Allele Frequency Distribution Analysis

Two independent allele frequency distribution analyses were undertaken to identify soybean genetic marker loci associated with tolerance to CRDC. By identifying such genetic markers, marker assisted selection (MAS) can be used to improve the efficiency of breeding for improved tolerance of soybean to CRDC.

Soybean Lines and Tolerance Scoring

The plant varieties used in the analysis were from diverse sources, including elite germplasm, commercially released cultivars and other public lines representing a broad range of germplasm. The lines used in the study had a broad maturity range varying from group 2 to group 4.

Two groups of soybean lines were assembled for each analysis based on their phenotypic extremes in tolerance to CRDC, where the plants were sorted into either highly susceptible or highly tolerant varieties. The classifications of tolerant and susceptible were based solely on observations of fortuitous, naturally occurring disease incidence in field tests over several years and greenhouse observations. The degree of plant tolerance to Charcoal Rot infection varied widely, as measured using a scale from one (highly susceptible) to nine (highly tolerant). Generally, a score of two (2) or three (3) indicated the most susceptible strains, and a score of seven (7) or eight (8) was assigned to the most tolerant lines. A score of one (1) was generally not used, as soybean strains with such extremely high susceptibility were not typically propagated. Tolerance scores of nine (9) were reserved for tolerance levels that are very rare and generally not observed in existing germplasm. If no disease was present in a field, no tolerance scoring was done. However, if a disease did occur in a specific field location, all of the lines in that location were scored. Scores for test strains accumulated over multiple locations and multiple years, and an averaged (e.g., consensus) score was ultimately assigned to each line.

Individual fields showing Charcoal Rot were monitored for disease symptoms during the vegetative stages but typically appear in the early to late reproductive stages. Data collection was typically done in three or four successive scorings about seven days apart. Scorings continued until worsening symptoms can no longer be quantified or until the symptoms are confounded by other factors such as other diseases, insect pressure, severe weather, or advancing maturity.

In assessing association of markers to tolerance, a qualitative "intergroup allele frequency distribution" comparison approach was used. Using this approach, those soybean lines that were considered to be representative of either the tolerant or susceptible classes were used for assessing association. A list of tolerant lines was constructed, where strains having a tolerance score of 7 or greater were considered "tolerant." Similarly, soybean lines with scores of three or less were collectively considered susceptible. Only lines that could be reliably placed into the two groups were used. Once a line is included in the "tolerant" or "susceptible" group, it was treated as an equal in that group, i.e., the actual quantitative ratings were not used.

In the study, 29 soybean lines were identified that were considered tolerant in the phenotypic spectrum; these plants formed the "TOLERANT" group. Also, 38 soybean lines were identified that were judged to be susceptible to Charcoal Rot; these strains formed the "SUSCEPTIBLE" group.

Soybean Genotyping

Each of the tolerant and susceptible lines was genotyped with SSR and SNP markers that span the soybean genome using techniques well known in the art. The genotyping protocol consisted of collecting young leaf tissue from eight individuals from each tolerant and resistant soybean strain, pooling (i.e., bulking) the leaf tissue from the eight individuals, and isolating genomic DNA from the pooled tissue. The soybean genomic DNA was extracted by the CTAB method, as described in Maroof, et al., (1984) *Proc. Natl. Acad. Sci. (USA)* 81:8014-8018.

The isolated genomic DNA was then used in PCR reactions using amplification primers specific for a large number of markers that covered all chromosomes in the soybean genome. The length of the PCR amplicon or amplicons from each PCR reaction were characterized. The length of the amplicons generated in the PCR reactions were compared to known allele definitions for the various markers (see, e.g., FIG. 4), and allele designations were assigned. SNP-type markers were genotyped using an ASH protocol.

Intergroup Allele Frequency Analysis

An "Intergroup Allele Frequency Distribution" analysis was conducted using GeneFlow™ version 7.0 software. An intergroup allele frequency distribution analysis provides a method for finding non-random distributions of alleles between two phenotypic groups.

During processing, a contingency table of allele frequencies is constructed and from this a G-statistic and probability are calculated (the G statistic is adjusted by using the William's correction factor). The probability value is adjusted to take into account the fact that multiple tests are being done (thus, there is some expected rate of false positives). The adjusted probability is proportional to the probability that the observed allele distribution differences between the two classes would occur by chance alone. The lower that probability value, the greater the likelihood that the Charcoal Rot infection phenotype and the marker will co-segregate. A more complete discussion of the derivation of the probability values can be found in the GeneFlow™ version 7.0 software documentation. See, also, Sokal and Rolf, (1981), *Biometry: The Principles and Practices of Statistics in Biological Research*, 2nd ed., San Francisco, W. H. Freeman and Co.

The underlying logic is that markers with significantly different allele distributions between the tolerant and susceptible groups (i.e., non random distributions) might be associated with the trait and can be used to separate them for purposes of marker assisted selection of soybean lines with previously uncharacterized tolerance or susceptibility to Charcoal Rot. The present analysis examined one marker locus at a time and determined if the allele distribution within the tolerant group is significantly different from the allele distribution within the susceptible group. A statistically different allele distribution is an indication that the marker is linked to a locus that is associated with reaction to Charcoal Rot. In this analysis, unadjusted probabilities less than one are considered significant (the marker and the phenotype show linkage disequilibrium), and adjusted probabilities less than approximately 0.05 are considered highly significant. Allele classes represented by less than 5 observations across both groups were not included in the statistical analysis. In this analysis, 444 marker loci had enough observations for analysis.

This analysis compares the plants' phenotypic score with the genotypes at the various loci. This type of intergroup analysis neither generates nor requires any map data. Subsequently, map data (for example, a composite soybean genetic map) is relevant in that multiple significant markers that are also genetically linked can be considered as collaborating evidence that a given chromosomal region is associated with the trait of interest.

Results

FIG. 1 provides a table listing the soybean markers that demonstrated linkage disequilibrium with the Charcoal Rot tolerance/susceptibility phenotype. Also indicated in that figure are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the adjusted probability values.

FIG. 2 provides the PCR primer sequences that were used to genotype these marker loci. FIG. 2 also provides the pigtail sequence used on the 5' end of the right SSR-marker primers and the number of nucleotides in the repeating element in the SSR. The observed alleles that are known to occur for these marker loci are provided in the allele dictionary in FIG. 4.

Out of 444 loci studied, simple sequence repeat (SSR) or single nucleotide polymorphism (SNP) loci having adjusted probability values for independent assortment with Charcoal Rot tolerance of less than approximately 0.05 were identified (see, FIG. 1). The statistical probabilities that the marker allele and tolerance phenotype are segregating independently are reflected in the Adjusted Probability values.

Discussion

There are a number of ways to use the information provided in this analysis for the development of improved soybean varieties. One application is to use the associated markers (or more based on a higher probability cutoff value) as candidates for mapping QTL in specific populations that are segregating for plants having tolerance to Charcoal Rot infection. In this application, one proceeds with conventional QTL mapping in a segregating population, but focusing on the markers that are associated with Charcoal Rot infection tolerance, instead of using markers that span the entire genome. This makes mapping efforts more cost-effective by dramatically reducing lab resources committed to the project. For example, instead of screening segregating populations with a large set of markers that spans the entire genome, one would screen with only those few markers that met some statistical cutoff in the intergroup allele association study. This will not only reduce the cost of mapping but will also eliminate false leads that will undoubtedly occur with a large set of markers. In any given cross, it is likely that only a small subset of the associated markers will actually be correlated with tolerance to Charcoal Rot infection. Once the few relevant markers are identified in any tolerant parent, future marker assisted selection (MAS) efforts can focus on only those markers that are important for that source of tolerance. By pre-selecting lines that have the allele associated with tolerance via MAS, one can eliminate the undesirable susceptible lines and concentrate the expensive field testing resources on lines that have a higher probability of being tolerant to Charcoal Rot infection.

Example 2

Trait Allele Correlation Analysis

One trait allele correlation analysis was conducted using GeneFlow v. 7.0 to identify soybean genetic marker loci associated with tolerance to CRDC. By identifying such genetic markers, marker assisted selection (MAS) can be used to improve the efficiency of breeding for improved tolerance of soybean to CRDC.

Soybean Lines and Tolerance Scoring

One hundred and sixty seven lines were characterized for their Charcoal Rot Drought Tolerance score. The plant varieties used in the analysis were from diverse sources, including elite germplasm, commercially released cultivars and other public lines representing a broad range of germplasm. The lines used in the study had a broad maturity range varying from group 2 to group 4.

The classifications of the lines for CRDC reaction were in a continuous range from 1 (susceptible) up to 8 (highly tolerant) and scores were based solely on observations of fortuitous, naturally occurring disease incidence in field tests over several years and greenhouse observations. Generally, a score of two (2) or three (3) indicated the most susceptible strains, and a score of seven (7) or eight (8) was assigned to the most tolerant lines. Tolerance scores of nine (9) were reserved for tolerance levels that are very rare and generally not observed in existing germplasm. If no disease was present in a field, no tolerance scoring was done. However, if a disease did occur in a specific field location, all of the lines in that location were scored. Scores for test strains accumulated over multiple locations and multiple years, and an averaged (e.g., consensus) score was ultimately assigned to each line.

Individual fields showing Charcoal Rot were monitored for disease symptoms during the vegetative stages but typically appear in the early to late reproductive stages. Data collection was typically done in three or four successive scorings about seven days apart. Scorings continued until worsening symptoms can no longer be quantified or until the symptoms are confounded by other factors such as other diseases, insect pressure, severe weather, or advancing maturity.

Soybean Genotyping

Each of the tolerant and susceptible lines was genotyped with SSR and SNP markers that span the soybean genome using techniques well known in the art. The genotyping protocol consisted of collecting young leaf tissue from eight individuals from each tolerant and resistant soybean strain, pooling (i.e., bulking) the leaf tissue from the eight individuals, and isolating genomic DNA from the pooled tissue. The soybean genomic DNA was extracted by the CTAB method, as described in Maroof, et al., (1984) *Proc. Natl. Acad. Sci.* (*USA*) 81:8014-8018.

The isolated genomic DNA was then used in PCR reactions using amplification primers specific for a large number of markers that covered all chromosomes in the soybean genome. The length of the PCR amplicon or amplicons from each PCR reaction were characterized. The length of the amplicons generated in the PCR reactions were compared to known allele definitions for the various markers (see, e.g., FIG. 4), and allele designations were assigned. SNP-type markers were genotyped using an ASH protocol.

Trait Allele Correlation Analysis

For the Trait Allele Correlation report you must select accessions, markers and a single trait. For each allele at each selected marker, the report will show you the effect of having 0, 1 or 2 doses of that allele on the trait of interest. For each dosage comparison it calculates a t-statistic, probability and adjusted probability by comparing the means of two different dosage classes. The adjusted probability gives you a better idea of the experiment-wise significance given the number of alleles being tested, and is calculated as $P\_adj=(1-((1-Prob)**n))$ where n is the number of tests being done in this analysis (see, Experimental Design: Procedures for the Behavioral Sciences). A more complete discussion of the derivation of the probability values can be found in the GeneFlow version 7.0 software documentation. See also, Sokal and Rolf, (1995) Biometry 3rd ed., San Francisco, W.H. Freeman and Co.

Results

FIG. 1 provides a table listing the soybean markers that demonstrated linkage disequilibrium with the CRDC trait scores of 167 lines. Also indicated in that figure are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the adjusted probability values.

FIG. 2 provides the PCR primer sequences that were used to genotype these marker loci. FIG. 2 also provides the pigtail sequence used on the 5' end of the right SSR-marker primers and the number of nucleotides in the repeating element in the SSR. The observed alleles that are known to occur for these marker loci are provided in the allele dictionary in FIG. 4.

Out of 444 loci studied, simple sequence repeat (SSR) or single nucleotide polymorphism (SNP) loci having adjusted probability values for independent assortment with Charcoal Rot tolerance of less than approximately 0.05 were identified (see, FIG. 1). The statistical probabilities that the marker allele and tolerance phenotype are segregating independently are reflected in the Adjusted Probability values.

Discussion

There are a number of ways to use the information provided in this analysis for the development of improved soybean varieties. One application is to use the associated markers (or more based on a higher probability cutoff value) as candidates for mapping QTL in specific populations that are segregating for plants having tolerance to Charcoal Rot infection. In this application, one proceeds with conventional QTL mapping in a segregating population, but focusing on the markers that are associated with Charcoal Rot infection tolerance, instead of using markers that span the entire genome. This makes mapping efforts more cost-effective by dramatically reducing lab resources committed to the project. For example, instead of screening segregating populations with a large set of markers that spans the entire genome, one would screen with only those few markers that met some statistical cutoff in the intergroup allele association study. This will not only reduce the cost of mapping but will also eliminate false leads that will undoubtedly occur with a large set of markers. In any given cross, it is likely that only a small subset of the associated markers will actually be correlated with tolerance to Charcoal Rot infection. Once the few relevant markers are identified in any tolerant parent, future marker assisted selection (MAS) efforts can focus on only those markers that are important for that source of tolerance. By pre-selecting lines that have the allele associated with tolerance via MAS, one can eliminate the undesirable susceptible lines and concentrate the expensive field testing resources on lines that have a higher probability of being tolerant to Charcoal Rot infection.

Example 3

Charcoal Rot Drought Complex Tolerance Phenotypic Assay

A field nursery was established in a region of Southwestern Missouri that was known for severe Charcoal rot symptoms caused by the fungus *Macrophomina phaseolina*. Management practices that promote severe Charcoal Rot Drought Complex symptoms were followed including: early planting date, high seeding rate, reduced tillage, and low soil fertility. Genotypes were blocked together by similar maturity and replicated three times. Each genotype was grown in a two row plot measuring 5 ft. wide×15 ft. long. Ratings were taken during the seed-filling stages when the plant's demand for water is the greatest. The first rating was taken during the R4-R5 stage and the final rating was taken during the R5-R6 growth stage.

Cultivar scores are based on a 1 to 9 system where a score of 9=no disease symptoms with normal plant growth; 8=very slight symptoms including up to a 10% reduction in leaflet and overall canopy size with no wilting; 7=wilting beginning to appear at the uppermost two nodes; 6=wilting at the uppermost three nodes and leaflet yellowing beginning appear; 5=Up to 5% plant death with wilting and yellowing of leaflets occurring at the uppermost four nodes; 4=Up to 10% plant death with wilting and yellowing of leaflets occurring at the uppermost four nodes; 3=Up to 25% plant death with wilting and yellowing of leaflets occurring at the uppermost four nodes; 2=up to 50% plant death; 1=50-100% plant death.

FIG. 8 gives a representative example of cultivars with vastly different Charcoal Rot Drought Complex tolerance using this scoring system.

Example 4

Genotyping the Mapping Population

For genotypic data, DNA was isolated from the collected leaves from 368 progeny. Leaf tissue was punched and the tissue was genotyped using SSR markers. A total of 333 SNP-based markers were screened against the mapping population to identify polymorphic markers potentially associated with the CRDC phenotype.

MapManager-QTX was used for both genetic mapping and QTL analysis. The 2000 permutation tests were used to establish the threshold for statistical significance (LOD ratio statistic—LRS). The mean score were used for QTL mapping. The LRS threshold at P=0.05 is 9.1 and at P=0.01 is 17.9.

The 333 SNP-based markers were screened for the population. The 333 SNP markers coalesced into 32 linkage groups, with 6 markers being unlinked. The number of markers for each linkage group ranged from 2 to 27.

One major QTL was identified on linkage group G (Table 1) with the closely linked marker of S01954-1-A. Several public markers in this region, Satt472, Satt191, Sat_117, and Sct_187, all are recognized to be associated with CRDC tolerance. This QTL has an LRS score of 32.5 and explains, on average, approximately 10% of the observed phenotypic variation.

TABLE 1

Interval mapping output for linkage group G

| Marker | Map | Stat | % | Add |
|---|---|---|---|---|
| S01954-1-A | 0.16 | 33.8 | 10 | 0.29 |
| | 0.17 | 34.9 | 10 | 0.30 |
| | 0.18 | 29.2 | 9 | 0.26 |

One major QTL was identified on linkage group C1 (Table 2) with the closely linked marker of S00415-1-A. Several public markers in this region, Satt607, Satt190, Satt139, Satt136, Sat_416, and Sat_085, all are recognized to be associated with CRDC tolerance. This QTL has an LRS score of 35.4 and explains, on average, approximately 10% of the observed phenotypic variation.

TABLE 2

Interval mapping output for linkage group C1

| Marker | Map | Stat | % | Add |
|---|---|---|---|---|
| S00415-1-A | 0.02 | 37.0 | 10 | 0.29 |
| | 0.03 | 36.8 | 10 | 0.29 |
| | 0.04 | 34.0 | 10 | 0.28 |

An interaction analysis was run on the loci from linkage group G and linkage group C1. No evidence of direct epistatic interaction between G and C1 was found.

One minor QTL was identified on linkage group D1b (Table 3) with the closely linked marker of S00705-1-A. Several public markers in this region, Satt428, Sat_169, Satt644, Satt041, and Satt546, all are recognized to be associated with CRDC tolerance. This QTL has an LRS score of 11.5 and explains, on average, approximately 4% of the variation.

TABLE 3

Interval mapping output for linkage group D1b

| Marker | Map | Stat | % | Add |
|---|---|---|---|---|
| S00705-1-A | 0.11 | 11.5 | 3 | 0.16 |
| | 0.12 | 12.3 | 4 | 0.17 |
| | 0.13 | 12.6 | 4 | 0.18 |

One minor QTL was identified on linkage group N (Table 4) with the closely linked marker of S02118-1-A. Several public markers in this region, Satt022, Sat_125, A363_3 all are recognized to be associated with CRDC tolerance. This QTL has an LRS score of 9.4 and explains, on average, approximately 3% of the variation.

TABLE 4

Interval mapping output for linkage group N

| Marker | Map | Stat | % | Add |
|---|---|---|---|---|
| S02118-1-A | 0.01 | 7.0 | 2 | 0.13 |
| | 0.02 | 8.5 | 2 | 0.14 |
| | 0.02 | 10.1 | 3 | 0.16 |

There were notable environmental difference between 2005 and 2006. The 2006 environment had much greater drought conditions versus 2005, resulting in added charcoal rot and physiological stress on the plant. The environments did effect the phenotypic distribution of the population. The 2005 environment resulted in a much broader charcoal rot phenotypic distribution, with the parents having a much greater phenotypic separation compared to the 2006 environment as show in the statistics below:

| | 2005 Statistics | 2006 Statistics |
|---|---|---|
| Mean | 6.408108 | 4.601333 |
| Standard Error | 0.053813 | 0.051677 |
| Median | 6.5 | 4.666667 |
| Mode | 7 | 4.333333 |
| Standard Deviation | 1.035123 | 1.000719 |
| Sample Variance | 1.071479 | 1.001439 |
| Kurtosis | 0.524948 | −0.09353 |
| Skewness | −0.55391 | −0.19395 |
| Range | 6.5 | 5 |
| Minimum | 2 | 2 |
| Maximum | 8.5 | 7 |

FIG. 1 provides a table listing the soybean markers that demonstrated linkage disequilibrium with the CRDC trait scores from pools or populations as noted. Also indicated in that figure are the chromosomes on which the markers are located and their approximate map position relative to other known markers, given in cM, with position zero being the first (most distal) marker known at the beginning of the chromosome. These map positions are not absolute, and represent an estimate of map position. The statistical probabilities that the marker allele and tolerance phenotype are segregating independently are reflected in the adjusted probability values.

What is claimed is:

1. A method of selecting a first soybean plant or germplasm that displays tolerance or improved tolerance to Charcoal Rot Drought Complex (CRDC), the method comprising:
   (a) isolating nucleic acids from a genome of the first soybean plant or germplasm;
   (b) detecting in the first soybean plant or germplasm at least one allele of a quantitative trait locus that is associated with the tolerance or improved tolerance, wherein said quantitative trait locus is localized to a chromosomal interval selected from the group consisting of (i) a chromosomal interval flanked by and including markers Satt467 and Satt416 on linkage group B2, and (ii) a chromosomal interval flanked by and including markers A605__1 and A519__2 on linkage group D1b wherein the at least one allele is detected using a composition comprising a detectable label; and,
   (c) selecting said first soybean plant or germplasm, or selecting a progeny of said first soybean plant or germplasm, comprising at least one allele associated with tolerance or improved tolerance to CRDC.

2. The method of claim 1, wherein said quantitative trait locus is localized to a chromosomal interval flanked by and including Satt467 and Satt416 on linkage group B2.

3. The method of claim 1, wherein said quantitative trait locus is localized to a chromosomal interval flanked by and including Sat__287 and OP_T02 on linkage group B2.

4. The method of claim 1, wherein said quantitative trait locus is S60211-TB.

5. The method of claim 1, wherein the at least one allele of the quantitative trait locus comprises S60211-TB:allele-1.

6. The method of claim 1, wherein said quantitative trait locus is localized to a chromosomal interval flanked by and including A605__1 and A519__2 on linkage group D1b.

7. The method of claim 1, wherein said quantitative trait locus is localized to a chromosomal interval flanked by and including Satt428 and B194__2 on linkage group D1b.

8. The method of claim 1, wherein said quantitative trait locus is S00705-1-A.

9. The method of claim 1, further comprising crossing said selected first soybean plant or germplasm with a second soybean plant or germplasm to introgress said quantitative trait locus into progeny soybean germplasm.

10. The method of claim 9, wherein the second soybean plant or germplasm displays less tolerance to CRDC as compared to the first soybean plant or germplasm, and wherein the introgressed soybean plant or germplasm displays an increased tolerance to CRDC as compared to the second plant or germplasm.

11. The method of claim 9, further comprising
   a) analyzing progeny soybean germplasm to determine the presence of tolerance to CRDC; and
   b) selecting progeny soybean germplasm that tests positive for the presence of tolerance to CRDC as being soybean germplasm into which germplasm having said quantitative trait locus has been introgressed.

12. A method of selecting a first soybean plant or germplasm that displays tolerance or improved tolerance to Charcoal Rot Drought Complex (CRDC), the method comprising:
   (a) isolating nucleic acids from a genome of the first soybean plant or germplasm;
   (b) detecting in the first soybean plant or germplasm at least one allele of a quantitative trait locus that is associated with the tolerance or improved tolerance, wherein said quantitative trait locus is separated by no more than 20 cM from a locus selected from the group consisting of S60211-TB on LG B2 and S00705-1 on LG D1b, wherein the at least one allele is detected using a composition comprising a detectable label; and, (c) selecting said first soybean plant or germplasm, or selecting a progeny of said first soybean plant or germplasm, comprising at least one allele associated with tolerance or improved tolerance to CRDC.

13. The method of claim 12, wherein said quantitative trait locus is separated by no more than 10 cM from a locus selected from the group consisting of S60211-TB on LG B2 and S00705-1 on LG D1b.

* * * * *